(12) United States Patent
Curtis et al.

(10) Patent No.: US 8,404,649 B2
(45) Date of Patent: Mar. 26, 2013

(54) ISOXAZOLINE OXIMES AS ANTIPARASITIC AGENTS

(75) Inventors: Michael Curtis, Portage, MI (US); Edmund L. Ellsworth, Portage, MI (US)

(73) Assignee: AH USA 42 LLC, New York, NY (US)

( * ) Notice: Subject to any disclaimer, the term of this patent is extended or adjusted under 35 U.S.C. 154(b) by 74 days.

(21) Appl. No.: 13/233,459

(22) Filed: Sep. 15, 2011

(65) Prior Publication Data

US 2012/0077765 A1    Mar. 29, 2012

Related U.S. Application Data

(60) Provisional application No. 61/386,003, filed on Sep. 24, 2010.

(51) Int. Cl.
  *A61K 31/42* (2006.01)
  *A61K 31/4402* (2006.01)
  *A61K 31/5395* (2006.01)
  *A61P 33/00* (2006.01)
  *C07D 261/04* (2006.01)

(52) U.S. Cl. ......... 514/30; 514/66; 514/229.2; 514/345; 514/378; 548/240

(58) Field of Classification Search .................. None
See application file for complete search history.

(56) References Cited

U.S. PATENT DOCUMENTS

| | | | |
|---|---|---|---|
| 7,662,972 B2 | 2/2010 | Mita et al. | |
| 7,964,204 B2 | 6/2011 | Lahm et al. | |
| 8,022,089 B2 | 9/2011 | Mita et al. | |
| 2007/0066617 A1 | 3/2007 | Mita et al. | |
| 2009/0312330 A1 | 12/2009 | Mita et al. | |
| 2010/0179195 A1 | 7/2010 | Lahm et al. | |
| 2010/0234219 A1 | 9/2010 | Lahm et al. | |
| 2010/0249424 A1 | 9/2010 | Annis et al. | |
| 2010/0254959 A1 | 10/2010 | Lahm et al. | |
| 2011/0124858 A1 | 5/2011 | Iwata et al. | |
| 2011/0251398 A1 | 10/2011 | Mita et al. | |

FOREIGN PATENT DOCUMENTS

| | | |
|---|---|---|
| EP | 1 731 512 | 12/2006 |
| WO | 2009/051956 | 4/2009 |
| WO | 2010/003923 | 1/2010 |

OTHER PUBLICATIONS

PCT International Search Report, PCT/IB2011/053929, mailed Dec. 27, 2011.

*Primary Examiner* — Kamal Saeed
(74) *Attorney, Agent, or Firm* — Paul M. Misiak

(57) ABSTRACT

This invention recites naphthyl isoxazoline oxime derivatives of Formula (1)

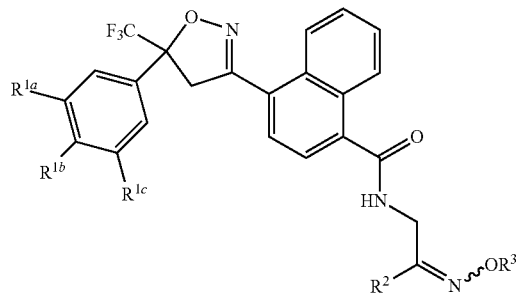

geometric isomers, stereoisomers thereof, pharmaceutically or veterinarily acceptable salts thereof, compositions thereof, and their use as a parasiticide in animals. The variables, $R^{1a}$, $R^{1b}$, $R^{1c}$, $R^2$, $R^3$, and ⁓ are as described herein.

19 Claims, No Drawings

ISOXAZOLINE OXIMES AS ANTIPARASITIC AGENTS

CROSS-REFERENCE TO RELATED APPLICATIONS

This application claims benefit of priority from U.S. Provisional Application Ser. No. 61/386,003 filed Sep. 24, 2010.

FIELD OF THE INVENTION

This invention relates to isoxazoline oxime derivatives having parasiticidal activity. The compounds of interest are substituted naphthyl isoxazoline oxime derivatives. The invention also relates to compositions and methods of use thereof.

BACKGROUND

There is a need for improved antiparasitic agents for use with animals, and in particular there is a need for improved insecticides and acaricides. Furthermore there is a need for improved topical and oral products with convenient administration and which contain one or more of such antiparasitic agents which can be used to effectively treat ectoparasites, such as insects (e.g., fleas, lice, and flies), acarids (e.g., mites and ticks), and crustaceans (e.g., copepods-sea lice). Such products would be particularly useful for the treatment of companion animals, such as cats, dogs, llamas, and horses; livestock, such as cattle, bison, swine, sheep, and goats; birds, such as chickens, ducks, and geese; and fish.

The compounds currently available for insecticidal and acaricidal treatment of companion animals and livestock do not always demonstrate good activity, good speed of action, or a long duration of action. Most treatments contain hazardous chemicals that can have serious consequences, including lethality from accidental ingestion. Persons applying these agents are generally advised to limit personal exposure. Pet collars and tags have been utilized to overcome some problems, but these are susceptible to chewing, ingestion, and subsequent toxicological affects to the animal. Thus, current treatments achieve varying degrees of success which depend partly on toxicity, method of administration, and efficacy. Currently, some agents are actually becoming ineffective due to parasitic resistance.

Naphthalene isoxazolines have been disclosed in the art as having insecticidal and acaricidal activity, for example WO2007/079162, WO2008/154528, and WO2009/002809. These publications disclose naphthyl carboxamides and other amide derivatives. Isoxazoline phenyl-oxime derivatives have been disclosed in publication WO2005/085216. A US equivalent patent, U.S. Pat. No. 7,662,972, discloses examples of these phenyl oximes. These phenyl oximes were shown to have an insecticidal rate of 80% or more at concentrations of 100 ppm and 500 ppm. WO2009/025983 provides methods of preparing isoxazoline substituted 1-naphthalenyl compounds, specifically with bromine, carboxylate, and carboxamide substituents. Despite the availability of effective, broad spectrum antiparasitic and insecticidal agents, there remains a need for a safer, convenient, and environmentally friendly product that will overcome the ever-present threat of resistance development.

These citations do not exemplify nor disclose any isoxazoline naphthyl oximes derivatives, nor does the prior art indicate that such compounds would be useful against a spectrum of parasitic species relevant to companion animals, livestock, birds, or fish, or against the range of parasitic morphological lifecycle stages.

The present invention overcomes one or more of the various disadvantages of, or improves upon, the properties of existing compounds. In particular the present invention provides new isoxazoline substituted naphthyl oximes which demonstrate such properties.

SUMMARY

The present invention provides Formula (1) compounds, geometric isomers, stereoisomers thereof, which act as parasiticides, in particular, ectoparasiticides; therefore may be used to prevent, treat, repel, and control acarids and insect infection and infestation in animals. In addition, the invention contemplates the control and prevention of tick borne diseases, for example, Lyme disease, canine and bovine anaplasmosis, canine ehrlichiosis, canine rickettsiosis, canine and bovine babesiosis, epizootic bovine abortion, and theileriosis. Thus, according to the invention, there is provided a compound of Formula (1)

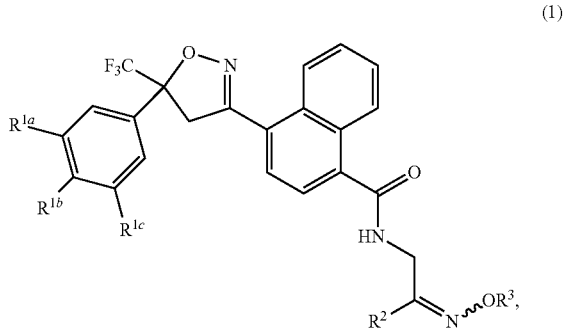

(1)

wherein $R^{1a}$, $R^{1b}$, and $R^{1c}$ are each independently selected from hydrogen, halo, cyano, $C_1$-$C_6$alkyl, $C_1$-$C_6$haloalkyl, $C_1$-$C_6$alkoxy, $C_0$-$C_6$alkyl $C_3$-$C_6$cycloalkyl, and $C_1$-$C_6$haloalkoxy;

$R^2$ is hydrogen, $C_1$-$C_6$alkyl, $C_0$-$C_6$alkyl phenyl, $C_0$-$C_6$alkyl heteroaryl, $C_0$-$C_6$alkyl $C_3$-$C_6$cycloalkyl, or $C_0$-$C_6$alkyl heterocycle;

$R^3$ is hydrogen, $C_1$-$C_6$alkyl, $C_0$-$C_6$alkyl $C_3$-$C_6$cycloalkyl, $C_2$-$C_6$alkenyl, $C_0$-$C_6$alkyl phenyl, $C_1$-$C_4$alkyl-O-phenyl, $C_0$-$C_6$alkyl heterocycle, or $C_0$-$C_6$alkyl heteroaryl;

each of $R^2$ and $R^3 C_1$-$C_6$alkyl or $C_0$-$C_6$alkyl$C_3$-$C_6$cycloalkyl can be optionally and independently substituted by at least one substituent selected from cyano, halo, hydroxyl, oxo, $C_1$-$C_6$alkoxy, $C_1$-$C_6$haloalkoxy, $C_1$-$C_6$haloalkyl, —S(O)$_p$R$^c$, —SH, —S(O)$_p$NR$^a$R$^b$, —NR$^a$R$^b$, —NR$^a$C(O)R$^b$, —SC(O)R$^c$, —SCN, or —C(O)NR$^a$R$^b$; and wherein $R^2$ and $R^3 C_0$-$C_6$alkyl phenyl, $C_0$-$C_6$alkyl heteroaryl, or $C_0$-$C_6$alkyl heterocycle moiety can be further optionally substituted with at least one substituent selected from cyano, halo, oxo, =S, =NR$^d$, hydroxyl, $C_1$-$C_6$alkoxy, $C_1$-$C_6$alkyl, $C_1$-$C_6$haloalkyl, —SH, —S(O)$_p$R, $C_1$-$C_6$haloalkoxy, Het, and phenyl;

R is $C_1$-$C_6$alkyl or $C_3$-$C_6$cycloalkyl each optionally substituted by at least one halo;

$R^a$ is hydrogen, $C_1$-$C_6$alkyl, or $C_0$-$C_3$alkyl$C_3$-$C_6$cycloalkyl; wherein the alkyl and alkylcycloalkyl is optionally substituted by cyano or at least one halo substituent;

$R^b$ is hydrogen, $C_1$–$C_6$alkyl, $C_3$–$C_6$cycloalkyl, $C_0$–$C_3$alkylphenyl, $C_0$–$C_3$alkylheteroaryl, or $C_0$–$C_3$alkylheterocycle, each optionally substituted, where chemically possible, with at least one substituent selected from hydroxyl, cyano, halo, or —S(O)$_p$R;

or wherein $R^a$ and $R^b$, with the N atom to which they are attached can form a 4-7 membered ring which may optionally include at least one additional heteroatom selected from N, O, and S;

$R^c$ is $C_1$–$C_6$alkyl, $C_1$–$C_6$haloalkyl, $C_1$–$C_6$haloalkyl$C_3$–$C_6$cycloalkyl, $C_0$–$C_3$alkyl$C_3$–$C_6$cycloalkyl, $C_0$–$C_3$alkylphenyl, $C_0$–$C_3$alkylheteroaryl, or $C_0$–$C_3$alkylheterocycle each optionally substituted with at least one substituent selected from cyano, halo, hydroxyl, oxo, $C_1$–$C_6$alkoxy, $C_1$–$C_6$haloalkoxy, $C_1$–$C_6$haloalkyl, —S(O)$_p$R, —SH, —S(O)$_p$NR$^a$R$^b$, —NR$^a$R$^b$, —NR$^a$C(O)R$^b$, —SC(O)R$^b$, —SCN, or —C(O)NR$^a$R$^b$;

$R^d$ is hydrogen, $C_1$–$C_6$alkyl, hydroxyl, cyano, nitro, —S(O)$_p$R$^c$, or $C_1$–$C_6$alkoxy;

p is the integer 0, 1, or 2; and

~~~ is a bond that represents E and Z geometric isomers, stereoisomers thereof, and pharmaceutically or veterinarily acceptable salts thereof.

In another aspect of the invention, $R^{1a}$, $R^{1b}$, and $R^{1c}$ are each independently selected from hydrogen, halo, cyano, $C_1$–$C_6$alkyl, $C_1$–$C_6$haloalkyl, $C_1$–$C_6$alkoxy, and $C_0$–$C_6$alkyl $C_3$–$C_6$cycloalkyl. In yet another aspect of the invention, $R^{1a}$, $R^{1b}$, and $R^{1c}$ are each independently selected from hydrogen, halo, cyano, $C_1$–$C_6$haloalkyl, and $C_0$–$C_6$alkyl $C_3$–$C_6$cycloalkyl. In yet another aspect of the invention, $R^{1a}$, $R^{1b}$, and $R^{1c}$ are each independently selected from hydrogen, halo, cyano, $C_1$–$C_6$haloalkyl, and $C_0$–$C_6$alkyl $C_3$–$C_6$cycloalkyl. In yet another aspect of the invention, $R^{1a}$, $R^{1b}$, and $R^{1c}$ are each independently selected from hydrogen, halo, cyano, and $C_1$–$C_6$haloalkyl. In yet another aspect of the invention, $R^{1a}$, $R^{1b}$, and $R^{1c}$ are each independently selected from hydrogen, halo, and $C_1$–$C_6$haloalkyl. In yet another aspect of the invention, $R^{1a}$, $R^{1b}$, and $R^{1c}$ are each independently selected from hydrogen, fluoro, chloro, and $C_1$–$C_6$haloalkyl. In yet another aspect of the invention, $R^{1a}$, $R^{1b}$, and $R^{1c}$ are each independently selected from hydrogen, fluoro, chloro, and CF$_3$.

In another aspect of the invention, $R^2$ is H, $C_1$–$C_6$alkyl, $C_0$–$C_6$alkyl phenyl, or $C_0$–$C_6$alkyl $C_3$–$C_6$cycloalkyl. In yet another aspect of the invention, $R^2$ is H, $C_1$–$C_6$alkyl or $C_0$–$C_6$alkyl $C_3$–$C_6$cycloalkyl. In yet another aspect of the invention, $R^2$ is H, methyl, ethyl, propyl, or $C_0$–$C_6$alkyl $C_3$–$C_6$cycloalkyl. In yet another aspect of the invention, $R^2$ is H, methyl, ethyl, —CH$_2$cyclopropyl, cyclopropyl, —CH$_2$cyclobutyl, or cyclobutyl. In yet another aspect of the invention, $R^2$ is H, methyl, ethyl, cyclopropyl, or cyclobutyl. In yet another aspect of the invention, $R^2$ is H, methyl, or cyclopropyl. In yet another aspect of the invention, $R^2$ is H. In yet another aspect of the invention, $R^2$ is methyl. In yet another aspect of the invention, $R^2$ is cyclopropyl.

In yet another aspect of the invention, $R^2$ is $C_1$–$C_6$alkyl or $C_0$–$C_6$alkyl $C_3$–$C_6$cycloalkyl optionally substituted as described herein. In yet another aspect of the invention, $R^2$ is $C_1$–$C_6$alkyl or $C_0$–$C_6$alkyl $C_3$–$C_6$cycloalkyl optionally substituted with halo. In yet another aspect of the invention, $R^2$ is $C_1$–$C_6$alkyl or $C_0$–$C_6$alkyl $C_3$–$C_6$cycloalkyl optionally substituted with fluoro or chloro. In yet another aspect of the invention, $R^2$ is —CF$_3$, —CH$_2$CF$_3$, —CHF$_2$, or —CH$_2$F. In yet another aspect of the invention, $R^2$ is —CF$_3$.

In yet another aspect of the invention $R^2$ is $C_0$–$C_6$alkyl phenyl, $C_0$–$C_6$alkyl heteroaryl, or $C_0$–$C_6$alkyl heterocycle optionally substituted as described herein.

In another aspect of the invention, $R^3$ is hydrogen, $C_1$–$C_6$alkyl, $C_0$–$C_6$alkyl $C_3$–$C_6$cycloalkyl, $C_0$–$C_6$alkyl phenyl, $C_0$–$C_6$alkyl heterocycle, or $C_0$–$C_6$alkyl heteroaryl. In yet another aspect of the invention, $R^3$ is H, $C_1$–$C_6$alkyl, $C_0$–$C_6$alkyl $C_3$–$C_6$cycloalkyl, or $C_0$–$C_6$alkyl heterocycle. In yet another aspect of the invention, $R^3$ is hydrogen, $C_1$–$C_6$alkyl, or $C_0$–$C_6$alkyl $C_3$–$C_6$cycloalkyl. In yet another aspect of the invention, $R^3$ is hydrogen, methyl, ethyl, propyl, isopropyl, butyl, t-butyl, n-butyl, or $C_0$–$C_6$alkyl $C_3$–$C_6$cycloalkyl. In yet another aspect of the invention, $R^3$ is hydrogen, methyl, ethyl, propyl, isopropyl, butyl, t-butyl, n-butyl, —CH$_2$cyclopropyl, —CH$_2$cyclobutyl, or —CH$_2$cyclopentyl. In yet another aspect of the invention, $R^3$ is hydrogen, methyl, ethyl, isopropyl, t-butyl, —CH$_2$cyclopropyl, or —CH$_2$cyclobutyl. In yet another aspect of the invention, $R^3$ is hydrogen, methyl, ethyl, isopropyl, t-butyl, —CH$_2$cyclopropyl, or —CH$_2$cyclobutyl. In yet another aspect of the invention, $R^3$ is hydrogen, methyl, ethyl, isopropyl, t-butyl, or —CH$_2$cyclopropyl.

In yet another aspect of the invention, $R^3$ is $C_1$–$C_6$alkyl or $C_0$–$C_6$alkyl $C_3$–$C_6$cycloalkyl optionally substituted as described herein. In yet another aspect of the invention, $R^2$ is $C_1$–$C_6$alkyl or $C_0$–$C_6$alkyl $C_3$–$C_6$cycloalkyl optionally substituted with halo. In yet another aspect of the invention, $R^3$ is —CF$_3$, —CH$_2$CF$_3$, —CH$_2$CH$_2$F, —CH$_2$CHF$_2$, CH$_2$F, or —CHF$_2$. In yet another aspect of the invention, $R^3$ is —CF$_3$ or —CH$_2$CH$_2$F.

In yet another aspect of the invention $R^3$ is $C_0$–$C_6$alkyl phenyl, $C_0$–$C_6$alkyl heteroaryl, or $C_0$–$C_6$alkyl heterocycle optionally substituted as described herein.

In another aspect of the invention are Formula (1) compounds selected from:

(E/Z)-4-(5-(3,5-dichloro-4-fluorophenyl)-5-(trifluoromethyl)-4,5-dihydroisoxazol-3-yl)-N-(2-(isopropoxyimino)ethyl)-1-naphthamide;

(E/Z)-4-(5-(3,5-dichloro-4-fluorophenyl)-5-(trifluoromethyl)-4,5-dihydroisoxazol-3-yl)-N-(2-(methoxyimino)ethyl)-1-naphthamide;

(E/Z)—N-(2-(tert-butoxyimino)ethyl)-4-(5-(3,5-dichloro-4-fluorophenyl)-5-(trifluoromethyl)-4,5-dihydroisoxazol-3-yl)-1-naphthamide;

(E/Z)-4-(5-(3,5-dichloro-4-fluorophenyl)-5-(trifluoromethyl)-4,5-dihydroisoxazol-3-yl)-N-(2-(hydroxyimino)ethyl)-1-naphthamide;

(E)-4-(5-(3,5-dichloro-4-fluorophenyl)-5-(trifluoromethyl)-4,5-dihydroisoxazol-3-yl)-N-(3,3,3-trifluoro-2-(hydroxyimino)propyl)-1-naphthamide;

(E)-4-(5-(3,5-dichloro-4-fluorophenyl)-5-(trifluoromethyl)-4,5-dihydroisoxazol-3-yl)-N-(3,3,3-trifluoro-2-(methoxyimino)propyl)-1-naphthamide;

(E)-4-(5-(3,5-dichloro-4-fluorophenyl)-5-(trifluoromethyl)-4,5-dihydroisoxazol-3-yl)-N-(2-(ethoxyimino)-3,3,3-trifluoropropyl)-1-naphthamide;

(E)-4-(5-(3,5-dichloro-4-fluorophenyl)-5-(trifluoromethyl)-4,5-dihydroisoxazol-3-yl)-N-(3,3,3-trifluoro-2-(isopropoxyimino)propyl)-1-naphthamide;

(E/Z)-4-(5-(3,5-dichlorophenyl)-5-(trifluoromethyl)-4,5-dihydroisoxazol-3-yl)-N-(2-(methoxyimino)ethyl)-1-naphthamide;

(E/Z)-4-(5-(3,5-dichlorophenyl)-5-(trifluoromethyl)-4,5-dihydroisoxazol-3-yl)-N-(2-(hydroxyimino)ethyl)-1-naphthamide;

(Z)-4-(5-(3,5-dichloro-4-fluorophenyl)-5-(trifluoromethyl)-4,5-dihydroisoxazol-3-yl)-N-(2-(methoxyimino)propyl)-1-naphthamide;

(E/Z)—N-(2-(ethoxyimino)ethyl)-4-(5-(3,4,5-trichlorophenyl)-5-(trifluoromethyl)-4,5-dihydroisoxazol-3-yl)-1-naphthamide;
(E/Z)—N-(2-(2-fluoroethoxyimino)ethyl)-4-(5-(3,4,5-trichlorophenyl)-5-(trifluoromethyl)-4,5-dihydroisoxazol-3-yl)-1-naphthamide;
(E/Z)—N-(2-(methoxyimino)ethyl)-4-(5-(3,4,5-trichlorophenyl)-5-(trifluoromethyl)-4,5-dihydroisoxazol-3-yl)-1-naphthamide;
(E/Z)-4-(5-(3,4-dichloro-5-(trifluoromethyl)phenyl)-5-(trifluoromethyl)-4,5-dihydroisoxazol-3-yl)-N-(2-(methoxyimino)ethyl)-1-naphthamide;
(E/Z)-4-(5-(3,5-bis(trifluoromethyl)phenyl)-5-(trifluoromethyl)-4,5-dihydroisoxazol-3-yl)-N-(2-(methoxyimino)ethyl)-1-naphthamide;
(E/Z)-4-(5-(3,4-difluoro-5-(trifluoromethyl)phenyl)-5-(trifluoromethyl)-4,5-dihydroisoxazol-3-yl)-N-(2-(methoxyimino)ethyl)-1-naphthamide;
(E/Z)-4-(5-(3-chloro-5-fluorophenyl)-5-(trifluoromethyl)-4,5-dihydroisoxazol-3-yl)-N-(2-(methoxyimino)ethyl)-1-naphthamide;
(E/Z)-4-(5-(3,5-dichloro-4-fluorophenyl)-5-(trifluoromethyl)-4,5-dihydroisoxazol-3-yl)-N-(2-(ethoxyimino)ethyl)-1-naphthamide;
(E/Z)-4-(5-(3,5-dichloro-4-fluorophenyl)-5-(trifluoromethyl)-4,5-dihydroisoxazol-3-yl)-N-(2-((2-fluoroethoxy)imino)ethyl)-1-naphthamide;
(E/Z)—N-(2-((cyclopropylmethoxy)imino)ethyl)-4-(5-(3,5-dichloro-4-fluorophenyl)-5-(trifluoromethyl)-4,5-dihydroisoxazol-3-yl)-1-naphthamide;
(E/Z)-4-(5-(3-fluoro-5-(trifluoromethyl)phenyl)-5-(trifluoromethyl)-4,5-dihydroisoxazol-3-yl)-N-(2-(methoxyimino)ethyl)-1-naphthamide;
(E/Z)-4-(5-(3-chloro-4-fluorophenyl)-5-(trifluoromethyl)-4,5-dihydroisoxazol-3-yl)-N-(2-(methoxyimino)ethyl)-1-naphthamide; and
(E/Z)-4-(5-(4-fluoro-3-(trifluoromethyl)phenyl)-5-(trifluoromethyl)-4,5-dihydroisoxazol-3-yl)-N-(2-(methoxyimino)ethyl)-1-naphthamide; stereoisomers thereof, and pharmaceutically or veterinarily acceptable salts thereof.

In yet another aspect of the invention are Formula (1) compounds selected from:
(E/Z)-4-(5-(3,5-dichloro-4-fluorophenyl)-5-(trifluoromethyl)-4,5-dihydroisoxazol-3-yl)-N-(2-(isopropoxyimino)ethyl)-1-naphthamide;
(E/Z)-4-(5-(3,5-dichloro-4-fluorophenyl)-5-(trifluoromethyl)-4,5-dihydroisoxazol-3-yl)-N-(2-(methoxyimino)ethyl)-1-naphthamide;
(E/Z)-4-(5-(3,5-dichloro-4-fluorophenyl)-5-(trifluoromethyl)-4,5-dihydroisoxazol-3-yl)-N-(2-(hydroxyimino)ethyl)-1-naphthamide;
(E)-4-(5-(3,5-dichloro-4-fluorophenyl)-5-(trifluoromethyl)-4,5-dihydroisoxazol-3-yl)-N-(3,3,3-trifluoro-2-(hydroxyimino)propyl)-1-naphthamide;
(Z)-4-(5-(3,5-dichloro-4-fluorophenyl)-5-(trifluoromethyl)-4,5-dihydroisoxazol-3-yl)-N-(2-(methoxyimino)propyl)-1-naphthamide;
(E/Z)—N-(2-(methoxyimino)ethyl)-4-(5-(3,4,5-trichlorophenyl)-5-(trifluoromethyl)-4,5-dihydroisoxazol-3-yl)-1-naphthamide;
(E/Z)-4-(5-(3,5-dichloro-4-fluorophenyl)-5-(trifluoromethyl)-4,5-dihydroisoxazol-3-yl)-N-(2-(ethoxyimino)ethyl)-1-naphthamide;
(E/Z)-4-(5-(3,5-dichloro-4-fluorophenyl)-5-(trifluoromethyl)-4,5-dihydroisoxazol-3-yl)-N-(2-((2-fluoroethoxy)imino)ethyl)-1-naphthamide;
(E/Z)-4-(5-(3-fluoro-5-(trifluoromethyl)phenyl)-5-(trifluoromethyl)-4,5-dihydroisoxazol-3-yl)-N-(2-(methoxyimino)ethyl)-1-naphthamide;
(E/Z)-4-(5-(3-chloro-4-fluorophenyl)-5-(trifluoromethyl)-4,5-dihydroisoxazol-3-yl)-N-(2-(methoxyimino)ethyl)-1-naphthamide; and
(E/Z)-4-(5-(4-fluoro-3-(trifluoromethyl)phenyl)-5-(trifluoromethyl)-4,5-dihydroisoxazol-3-yl)-N-(2-(methoxyimino)ethyl)-1-naphthamide; stereoisomers thereof, and pharmaceutically or veterinarily acceptable salts thereof.

In yet another aspect of the invention are Formula (1) compounds selected from:
(E)-4-(5-(3,5-dichlorophenyl)-5-(trifluoromethyl)-4,5-dihydroisoxazol-3-yl)-N-(3,3,3-trifluoro-2-(hydroxyimino)propyl)-1-naphthamide;
(E)-4-(5-(3,5-dichloro-4-fluorophenyl)-5-(trifluoromethyl)-4,5-dihydroisoxazol-3-yl)-N-(3,3,3-trifluoro-2-(methoxyimino)propyl)-1-naphthamide;
(E/Z)-4-{5-[3-fluoro-4-(trifluoromethyl)phenyl]-5-(trifluoromethyl)-4,5-dihydroisoxazol-3-yl}-N-2-(methoxyimino)ethyl-1-naphthamide;
(E/Z)-4-(5-(4-fluoro-3-(trifluoromethyl)phenyl)-5-(trifluoromethyl)-4,5-dihydroisoxazol-3-yl)-N-(2-(methoxyimino)ethyl)-1-naphthamide;
(E/Z)-4-(5-(3-chloro-4-(trifluoromethyl)phenyl)-5-(trifluoromethyl)-4,5-dihydroisoxazol-3-yl)-N-(2-(methoxyimino)ethyl)-1-naphthamide;
(E/Z)-4-(5-(3,4-dichlorophenyl)-5-(trifluoromethyl)-4,5-dihydroisoxazol-3-yl)-N-(2-(methoxyimino)ethyl)-1-naphthamide;
(E/Z)-4-(5-(3-chloro-4,5-difluorophenyl)-5-(trifluoromethyl)-4,5-dihydroisoxazol-3-yl)-N-(2-(methoxyimino)ethyl)-1-naphthamide;
(E/Z)-4-(5-(3-chloro-4-fluorophenyl)-5-(trifluoromethyl)-4,5-dihydroisoxazol-3-yl)-N-(2-(methoxyimino)ethyl)-1-naphthamide;
(E/Z)-4-(5-(3,5-difluorophenyl)-5-(trifluoromethyl)-4,5-dihydroisoxazol-3-yl)-N-(2-(methoxyimino)ethyl)-1-naphthamide;
(E/Z)-4-(5-(3-fluorophenyl)-5-(trifluoromethyl)-4,5-dihydroisoxazol-3-yl)-N-(2-(methoxyimino)ethyl)-1-naphthamide;
(E/Z)-4-(5-(3,5-dichloro-4-fluorophenyl)-5-(trifluoromethyl)-4,5-dihydroisoxazol-3-yl)-N-(2-(methoxyimino)ethyl)-N-methyl-1-naphthamide;
(E/Z)—N-(2-cyclopropyl-2-(methoxyimino)ethyl)-4-(5-(3,5-dichloro-4-fluorophenyl)-5-(trifluoromethyl)-4,5-dihydroisoxazol-3-yl)-1-naphthamide;
(E/Z)—N-(2-(isobutoxyimino)ethyl)-4-(5-(3,4,5-trichlorophenyl)-5-(trifluoromethyl)-4,5-dihydroisoxazol-3-yl)-1-naphthamide;
(E/Z)—N-(2-(tert-butoxyimino)ethyl)-4-(5-(3,4,5-trichlorophenyl)-5-(trifluoromethyl)-4,5-dihydroisoxazol-3-yl)-1-naphthamide;
(E/Z)—N-(2-((allyloxy)imino)ethyl)-4-(5-(3,4,5-trichlorophenyl)-5-(trifluoromethyl)-4,5-dihydroisoxazol-3-yl)-1-naphthamide;
(E/Z)—N-(2-((benzyloxy)imino)ethyl)-4-(5-(3,4,5-trichlorophenyl)-5-(trifluoromethyl)-4,5-dihydroisoxazol-3-yl)-1-naphthamide;
(E/Z)—N-(2-(isopropoxyimino)ethyl)-4-(5-(3,4,5-trichlorophenyl)-5-(trifluoromethyl)-4,5-dihydroisoxazol-3-yl)-1-naphthamide;
(E/Z)—N-(2-((cyclopentyloxy)imino)ethyl)-4-(5-(3,5-dichloro-4-fluorophenyl)-5-(trifluoromethyl)-4,5-dihydroisoxazol-3-yl)-1-naphthamide;

(E/Z)-4-(5-(3-chlorophenyl)-5-(trifluoromethyl)-4,5-dihydroisoxazol-3-yl)-N-(2-(methoxyimino)ethyl)-1-naphthamide;

(E/Z)-4-(5-(4-chloro-3-(trifluoromethyl)phenyl)-5-(trifluoromethyl)-4,5-dihydroisoxazol-3-yl)-N-(2-(methoxyimino)ethyl)-1-naphthamide;

(E/Z)-4-(5-(4-chloro-3-fluorophenyl)-5-(trifluoromethyl)-4,5-dihydroisoxazol-3-yl)-N-(2-(methoxyimino)ethyl)-1-naphthamide;

(E/Z)—N-(2-(methoxyimino)ethyl)-4-(5-(trifluoromethyl)-5-(3,4,5-trifluorophenyl)-4,5-dihydroisoxazol-3-yl)-1-naphthamide;

(E/Z)-4-(5-(3-fluoro-5-(trifluoromethyl)phenyl)-5-(trifluoromethyl)-4,5-dihydroisoxazol-3-yl)-N-(2-(methoxyimino)ethyl)-1-naphthamide;

(E/Z)—N-(2-(methoxyimino)ethyl)-4-(5-(trifluoromethyl)-5-(3-(trifluoromethyl)phenyl)-4,5-dihydroisoxazol-3-yl)-1-naphthamide;

(E/Z)-4-(5-(3,4-difluorophenyl)-5-(trifluoromethyl)-4,5-dihydroisoxazol-3-yl)-N-(2-(methoxyimino)ethyl)-1-naphthamide;

(E/Z)—N-(2-((cyclohex-2-en-1-yloxy)imino)ethyl)-4-(5-(3,5-dichloro-4-fluorophenyl)-5-(trifluoromethyl)-4,5-dihydroisoxazol-3-yl)-1-naphthamide;

(E/Z)-4-(5-(3-chloro-5-(trifluoromethyl)phenyl)-5-(trifluoromethyl)-4,5-dihydroisoxazol-3-yl)-N-(2-(methoxyimino)ethyl)-1-naphthamide;

(E/Z)—N-(2-((cyanomethoxy)imino)ethyl)-4-(5-(3,5-dichloro-4-fluorophenyl)-5-(trifluoromethyl)-4,5-dihydroisoxazol-3-yl)-1-naphthamide;

(E/Z)-4-(5-(3,5-dichloro-4-fluorophenyl)-5-(trifluoromethyl)-4,5-dihydroisoxazol-3-yl)-N-(2-((2-(piperidin-1-yl)ethoxy)imino)ethyl)-1-naphthamide;

(E/Z)-4-(5-(3,5-dichloro-4-fluorophenyl)-5-(trifluoromethyl)-4,5-dihydroisoxazol-3-yl)-N-(2-((2-morpholinoethoxy)imino)ethyl)-1-naphthamide;

(E/Z)—N-(2-((2-cyanoethoxy)imino)ethyl)-4-(5-(3,5-dichloro-4-fluorophenyl)-5-(trifluoromethyl)-4,5-dihydroisoxazol-3-yl)-1-naphthamide;

(E/Z)-4-(5-(3,5-dichloro-4-fluorophenyl)-5-(trifluoromethyl)-4,5-dihydroisoxazol-3-yl)-N-(2-((2-(methylamino)ethoxy)imino)ethyl)-1-naphthamide;

(E/Z)-4-(5-(3,5-dichloro-4-fluorophenyl)-5-(trifluoromethyl)-4,5-dihydroisoxazol-3-yl)-N-(2-((2-(pyrrolidin-1-yl)ethoxy)imino)ethyl)-1-naphthamide;

(E/Z)-4-(5-(3,5-dichloro-4-fluorophenyl)-5-(trifluoromethyl)-4,5-dihydroisoxazol-3-yl)-N-(2-((2-hydroxybutoxy)imino)ethyl)-1-naphthamide;

(E/Z)-4-(5-(3,5-dichloro-4-fluorophenyl)-5-(trifluoromethyl)-4,5-dihydroisoxazol-3-yl)-N-(2-((2-(diethylamino)ethoxy)imino)ethyl)-1-naphthamide;

(E/Z)-2-(((2-(4-(5-(3,5-dichloro-4-fluorophenyl)-5-(trifluoromethyl)-4,5-dihydroisoxazol-3-yl)-1-naphthamido)ethylidene)amino)oxy)acetic acid;

(E/Z)-3-(((2-(4-(5-(3,5-dichloro-4-fluorophenyl)-5-(trifluoromethyl)-4,5-dihydroisoxazol-3-yl)-1-naphthamido)ethylidene)amino)oxy)propanoic acid;

(E/Z)-4-(5-(3,5-dichloro-4-fluorophenyl)-5-(trifluoromethyl)-4,5-dihydroisoxazol-3-yl)-N-(2-((2-(dimethylamino)ethoxy)imino)ethyl)-1-naphthamide;

(E/Z)—N-(2-(methoxyimino)ethyl)-4-(5-(3,4,5-trichlorophenyl)-5-(trifluoromethyl)-4,5-dihydroisoxazol-3-yl)-1-naphthamide;

(E/Z)—N-(2-(((4-chlorobenzyl)oxy)imino)ethyl)-4-(5-(3,5-dichloro-4-fluorophenyl)-5-(trifluoromethyl)-4,5-dihydroisoxazol-3-yl)-1-naphthamide;

(E)-4-(5-(3,5-dichloro-4-fluorophenyl)-5-(trifluoromethyl)-4,5-dihydroisoxazol-3-yl)-N-(2-(((2-fluorobenzyl)oxy)imino)ethyl)-1-naphthamide;

(E/Z)-4-(5-(3,5-dichloro-4-fluorophenyl)-5-(trifluoromethyl)-4,5-dihydroisoxazol-3-yl)-N-(2-(((4-methoxybenzyl)oxy)imino)ethyl)-1-naphthamide;

(E/Z)-4-(5-(3,5-dichloro-4-fluorophenyl)-5-(trifluoromethyl)-4,5-dihydroisoxazol-3-yl)-N-(2-(((2,3-difluorobenzyl)oxy)imino)ethyl)-1-naphthamide;

(E/Z)-4-(5-(3,5-dichloro-4-fluorophenyl)-5-(trifluoromethyl)-4,5-dihydroisoxazol-3-yl)-N-(2-(((2-methoxybenzyl)oxy)imino)ethyl)-1-naphthamide;

(E/Z)-4-(5-(3,5-dichloro-4-fluorophenyl)-5-(trifluoromethyl)-4,5-dihydroisoxazol-3-yl)-N-(2-(isobutoxyimino)ethyl)-1-naphthamide;

(E/Z)-4-(5-(3,5-dichloro-4-fluorophenyl)-5-(trifluoromethyl)-4,5-dihydroisoxazol-3-yl)-N-(2-(((3-fluorobenzyl)oxy)imino)ethyl)-1-naphthamide;

(E/Z)-4-(5-(3,5-dichloro-4-fluorophenyl)-5-(trifluoromethyl)-4,5-dihydroisoxazol-3-yl)-N-(2-(((3-(pyridin-3-yl)isoxazol-5-yl)methoxy)imino)ethyl)-1-naphthamide;

(E/Z)-4-(5-(3,5-dichloro-4-fluorophenyl)-5-(trifluoromethyl)-4,5-dihydroisoxazol-3-yl)-N-(2-(propoxyimino)ethyl)-1-naphthamide;

(E/Z)-4-(5-(3,5-dichloro-4-fluorophenyl)-5-(trifluoromethyl)-4,5-dihydroisoxazol-3-yl)-N-(2-(((2-hydroxybenzyl)oxy)imino)ethyl)-1-naphthamide;

(E/Z)-4-(5-(3,5-dichloro-4-fluorophenyl)-5-(trifluoromethyl)-4,5-dihydroisoxazol-3-yl)-N-(2-(((4-methylbenzyl)oxy)imino)ethyl)-1-naphthamide;

(E/Z)-4-(5-(3,5-dichloro-4-fluorophenyl)-5-(trifluoromethyl)-4,5-dihydroisoxazol-3-yl)-N-(2-(((2,6-dimethylbenzyl)oxy)imino)ethyl)-1-naphthamide;

(E/Z)-4-(5-(3,5-dichloro-4-fluorophenyl)-5-(trifluoromethyl)-4,5-dihydroisoxazol-3-yl)-N-(2-((pyridin-4-ylmethoxy)imino)ethyl)-1-naphthamide;

(E/Z)—N-(2-(butoxyimino)ethyl)-4-(5-(3,5-dichloro-4-fluorophenyl)-5-(trifluoromethyl)-4,5-dihydroisoxazol-3-yl)-1-naphthamide;

(E/Z)-4-(5-(3,5-dichloro-4-fluorophenyl)-5-(trifluoromethyl)-4,5-dihydroisoxazol-3-yl)-N-(2-(phenoxyimino)ethyl)-1-naphthamide;

(E/Z)-4-(5-(3,5-dichloro-4-fluorophenyl)-5-(trifluoromethyl)-4,5-dihydroisoxazol-3-yl)-N-(2-(((2,6-difluorobenzyl)oxy)imino)ethyl)-1-naphthamide;

(E/Z)-4-(5-(3,5-dichloro-4-fluorophenyl)-5-(trifluoromethyl)-4,5-dihydroisoxazol-3-yl)-N-(2-(((3-methoxybenzyl)oxy)imino)ethyl)-1-naphthamide;

(E/Z)-4-(5-(3,5-dichloro-4-fluorophenyl)-5-(trifluoromethyl)-4,5-dihydroisoxazol-3-yl)-N-(2-(((4-fluorobenzyl)oxy)imino)ethyl)-1-naphthamide;

(E/Z)-4-(5-(3,5-dichloro-4-fluorophenyl)-5-(trifluoromethyl)-4,5-dihydroisoxazol-3-yl)-N-(2-(((2,4-dimethoxybenzyl)oxy)imino)ethyl)-1-naphthamide;

(E/Z)—N-(2-(((3-chloro-4-fluorobenzyl)oxy)imino)ethyl)-4-(5-(3,5-dichloro-4-fluorophenyl)-5-(trifluoromethyl)-4,5-dihydroisoxazol-3-yl)-1-naphthamide;

(E/Z)—N-(2-(((3-chlorobenzyl)oxy)imino)ethyl)-4-(5-(3,5-dichloro-4-fluorophenyl)-5-(trifluoromethyl)-4,5-dihydroisoxazol-3-yl)-1-naphthamide;

(E/Z)-4-(5-(3,5-dichloro-4-fluorophenyl)-5-(trifluoromethyl)-4,5-dihydroisoxazol-3-yl)-N-(2-(((2,4-difluorobenzyl)oxy)imino)ethyl)-1-naphthamide;

(E/Z)-4-(5-(3,5-dichloro-4-fluorophenyl)-5-(trifluoromethyl)-4,5-dihydroisoxazol-3-yl)-N-(2-((2-hydroxyethoxy)imino)ethyl)-1-naphthamide;

(E/Z)—N-(2-((cyclohexylmethoxy)imino)ethyl)-4-(5-(3,5-dichloro-4-fluorophenyl)-5-(trifluoromethyl)-4,5-dihydroisoxazol-3-yl)-1-naphthamide;

(E/Z)-4-(5-(3,5-dichloro-4-fluorophenyl)-5-(trifluoromethyl)-4,5-dihydroisoxazol-3-yl)-N-(2-(((3-phenylisoxazol-5-yl)methoxy)imino)ethyl)-1-naphthamide;

(E/Z)-4-(5-(3,5-dichloro-4-fluorophenyl)-5-(trifluoromethyl)-4,5-dihydroisoxazol-3-yl)-N-(2-(((3,4-dichlorobenzyl)oxy)imino)ethyl)-1-naphthamide;

(E/Z)-4-(5-(3,5-dichloro-4-fluorophenyl)-5-(trifluoromethyl)-4,5-dihydroisoxazol-3-yl)-N-(2-(((2-methylbenzyl)oxy)imino)ethyl)-1-naphthamide;

(E/Z)—N-(2-((cyclobutylmethoxy)imino)ethyl)-4-(5-(3,5-dichloro-4-fluorophenyl)-5-(trifluoromethyl)-4,5-dihydroisoxazol-3-yl)-1-naphthamide;

(E/Z)-4-(5-(3,5-dichloro-4-fluorophenyl)-5-(trifluoromethyl)-4,5-dihydroisoxazol-3-yl)-N-(2-(((4-hydroxybenzyl)oxy)imino)ethyl)-1-naphthamide;

(E/Z)-4-(5-(3,5-dichloro-4-fluorophenyl)-5-(trifluoromethyl)-4,5-dihydroisoxazol-3-yl)-N-(2-((pyridin-3-ylmethoxy)imino)ethyl)-1-naphthamide;

(E/Z)—N-(2-((cyclopentylmethoxy)imino)ethyl)-4-(5-(3,5-dichloro-4-fluorophenyl)-5-(trifluoromethyl)-4,5-dihydroisoxazol-3-yl)-1-naphthamide;

(E/Z)-4-(5-(3,5-dichloro-4-fluorophenyl)-5-(trifluoromethyl)-4,5-dihydroisoxazol-3-yl)-N-(2-(phenethoxyimino)ethyl)-1-naphthamide;

(E/Z)—N-(2-(((4-chloro-3-fluorobenzyl)oxy)imino)ethyl)-4-(5-(3,5-dichloro-4-fluorophenyl)-5-(trifluoromethyl)-4,5-dihydroisoxazol-3-yl)-1-naphthamide;

(E/Z)-4-(5-(3,5-dichloro-4-fluorophenyl)-5-(trifluoromethyl)-4,5-dihydroisoxazol-3-yl)-N-(2-(((3,5-dichlorobenzyl)oxy)imino)ethyl)-1-naphthamide;

(E/Z)—N-(2-((benzyloxy)imino)ethyl)-4-(5-(3,5-dichloro-4-fluorophenyl)-5-(trifluoromethyl)-4,5-dihydroisoxazol-3-yl)-1-naphthamide;

(E/Z)-4-(5-(3,5-dichloro-4-fluorophenyl)-5-(trifluoromethyl)-4,5-dihydroisoxazol-3-yl)-N-(2-((2-phenoxyethoxy)imino)ethyl)-1-naphthamide;

(E/Z)—N-(2-((3-(1H-1,2,4-triazol-1-yl)propoxy)imino)ethyl)-4-(5-(3,5-dichloro-4-fluorophenyl)-5-(trifluoromethyl)-4,5-dihydroisoxazol-3-yl)-1-naphthamide;

(E/Z)-4-(5-(3,5-dichloro-4-fluorophenyl)-5-(trifluoromethyl)-4,5-dihydroisoxazol-3-yl)-N-(2-(((3,4-difluorobenzyl)oxy)imino)ethyl)-1-naphthamide;

(E/Z)-4-(5-(3,5-dichloro-4-fluorophenyl)-5-(trifluoromethyl)-4,5-dihydroisoxazol-3-yl)-N-(2-((4-hydroxybutoxy)imino)ethyl)-1-naphthamide;

(E/Z)-4-(5-(3,5-dichloro-4-fluorophenyl)-5-(trifluoromethyl)-4,5-dihydroisoxazol-3-yl)-N-(2-(methoxyimino)ethyl)-1-naphthamide;

(E/Z)-4-(5-(3,5-dichloro-4-fluorophenyl)-5-(trifluoromethyl)-4,5-dihydroisoxazol-3-yl)-N-(2-(methoxyimino)ethyl)-1-naphthamide;

(E/Z)—N-(2-(tert-butoxyimino)ethyl)-4-(5-(3,5-dichlorophenyl)-5-(trifluoromethyl)-4,5-dihydroisoxazol-3-yl)-1-naphthamide;

(E)-4-(5-(3,5-dichloro-4-fluorophenyl)-5-(trifluoromethyl)-4,5-dihydroisoxazol-3-yl)-N-(2-(ethoxyimino)-3,3,3-trifluoropropyl)-1-naphthamide;

(E)-4-(5-(3,5-dichloro-4-fluorophenyl)-5-(trifluoromethyl)-4,5-dihydroisoxazol-3-yl)-N-(3,3,3-trifluoro-2-(isopropoxyimino)propyl)-1-naphthamide;

(E/Z)—N-(2-(tert-butoxyimino)ethyl)-4-(5-(3,5-dichloro-4-fluorophenyl)-5-(trifluoromethyl)-4,5-dihydroisoxazol-3-yl)-1-naphthamide;

(E/Z)-4-(5-(3,5-dichloro-4-fluorophenyl)-5-(trifluoromethyl)-4,5-dihydroisoxazol-3-yl)-N-(2-(methoxyimino)ethyl)-1-naphthamide;

(E/Z)-4-(5-(3,5-dichlorophenyl)-5-(trifluoromethyl)-4,5-dihydroisoxazol-3-yl)-N-(2-(isopropoxyimino)ethyl)-1-naphthamide;

(E)-4-(5-(3,5-dichlorophenyl)-5-(trifluoromethyl)-4,5-dihydroisoxazol-3-yl)-N-(3,3,3-trifluoro-2-(methoxyimino)propyl)-1-naphthamide;

(E)-4-(5-(3,5-dichlorophenyl)-5-(trifluoromethyl)-4,5-dihydroisoxazol-3-yl)-N-(3,3,3-trifluoro-2-(isopropoxyimino)propyl)-1-naphthamide; and (E)-4-(5-(3,4,5-trichlorophenyl)-5-(trifluoromethyl)-4,5-dihydroisoxazol-3-yl)-N-(3,3,3-trifluoro-2-(hydroxyimino)propyl)-1-naphthamide, stereoisomers thereof, and pharmaceutically or veterinarily acceptable salts thereof.

In another aspect of the invention, is a veterinary composition that comprises a) a Formula (1) compound, geometric isomers, stereoisomers thereof, or a pharmaceutically or veterinarily acceptable salt thereof, and (b) a pharmaceutically or veterinarily acceptable excipient, diluent, or carrier.

In another aspect of the invention, the composition comprises a therapeutically effective amount of a Formula (1) compound, geometric isomer, stereoisomer thereof, or pharmaceutically or veterinarily acceptable salt thereof, and a pharmaceutically or veterinarily acceptable excipient, diluent, or carrier.

The composition may comprise at least one additional veterinary agent. Preferred additional veterinary agents include endoparasiticides, ectoparasiticides, insecticides, and anthelmintics.

In yet another aspect of the invention is the use of a Formula (1) compound for the manufacture of a medicament.

In yet another aspect of the invention is a method for treating a parasitic infection or infestation in an animal that includes the step of administering to said animal, in need of such treatment, a therapeutically effective amount of a Formula (1) compound, geometric isomer, stereoisomer thereof, or pharmaceutically or veterinarily acceptable salt thereof. Formula (1) compounds, geometric isomers, stereoisomers thereof, pharmaceutically or veterinarily acceptable salts thereof, or compositions thereof, may be administered orally, topically, intramuscularly, and subcutaneously. In yet another aspect of the invention, the compositions can be administered orally or topically. In yet another aspect of the invention the composition can be administered topically. In yet another aspect of the invention, the composition can be administered orally. In yet another aspect of the invention, the composition can be administered subcutaneously. In yet another aspect of the invention, the composition can be administered intramuscularly.

In yet another aspect of the invention is a method for treating a parasitic infection or infestation in an animal that includes the step of administering to said animal, in need of such treatment, a therapeutically effective amount of a compound of the present invention, geometric isomer, stereoisomer thereof, or pharmaceutically or veterinarily acceptable salt thereof, in combination with at least one additional veterinary agent. Formula (1) compounds, geometric isomers, stereoisomers thereof, pharmaceutically or veterinarily acceptable salts thereof, alone, or with at least one additional veterinary agent, or compositions thereof, may be administered orally, topically, intramuscularly, and subcutaneously.

Preferably, the animal is a non-human and human mammal. More preferably, the non-human animal is a companion animal or livestock. Preferably, the companion animal is a dog, cat, or horse. More preferred, the companion animal is dog. Preferably, livestock is bovine, swine, or ovine. More preferred livestock is bovine. Preferred bovine is cattle. In another aspect of the invention, the animal is a bird. Preferably, the bird is fowl (i.e., chicken, turkey, goose, or duck). In another aspect of the invention, the animal is a fish.

Compounds of the present invention alone, or in combination with an additional veterinary agent may be administered as (a) a single veterinary composition which comprises a compound of the present invention, stereoisomer thereof, pharmaceutically or veterinarily acceptable salt thereof, and optionally, at least one additional veterinary agent as described herein and a pharmaceutically or veterinarily acceptable excipient, diluent, or carrier; or (b) two separate pharmaceutical or veterinary compositions comprising (i) a first composition comprising a compound of the present invention, stereoisomer thereof, pharmaceutically or veterinarily acceptable salt thereof, and a pharmaceutically or veterinarily acceptable excipient, diluent, or carrier, and (ii) a second composition comprising at least one additional veterinary agent, as described herein and a pharmaceutically or veterinarily acceptable excipient, diluent, or carrier. The veterinary compositions may be administered simultaneously or sequentially and in any order.

All of the recited WO patent publications and US patents described herein are incorporated by reference in their entirety.

DEFINITIONS

For purposes of the present invention, as described and claimed herein, the following terms and phrases are defined as follows:

"Additional veterinary agent(s)" as used herein, unless otherwise indicated, refers to other veterinary or pharmaceutical compounds or products that provide a therapeutically effective amount of said agents that are useful for the treatment of a parasitic infection in an animal, as described herein.

"Alkoxy", as used herein, unless otherwise indicated, refers to an oxygen moiety having a further alkyl substituent. The alkyl portion (i.e., alkyl moiety) of an alkoxy group has the same definition as below. Non-limiting examples include: —OCH$_3$, —OCH$_2$CH$_3$, and the like.

"Alkyl", as used herein, unless otherwise indicated, refers to saturated monovalent hydrocarbon alkane radicals of the general formula $C_nH_{2n+1}$. The alkane radical may be straight or branched and may be unsubstituted or substituted. For example, the term "($C_1$-$C_6$) alkyl" refers to a monovalent, straight or branched aliphatic group containing 1 to 6 carbon atoms. Non-exclusive examples of ($C_1$-$C_6$) alkyl groups include, but are not limited to methyl, ethyl, propyl, isopropyl, sec-butyl, t-butyl, n-propyl, n-butyl, i-butyl, s-butyl, n-pentyl, 1-methylbutyl, 2-methylbutyl, 3-methylbutyl, neopentyl, 3,3-dimethylpropyl, 2-methylpentyl, hexyl, and the like. The term "$C_0$-$C_6$ alkyl" is defined analogously to the term "alkyl" whereas the $C_0$ represents no carbon atoms. For example, $C_0$-alkylphenyl is analogous to phenyl, $C_1$-phenyl is analogous to benzyl, and the like. Examples of "haloalkoxy" include CF$_3$O—, CCl$_3$CH$_2$O—, HCF$_2$CH$_2$CH$_2$O—, CF$_3$CH$_2$O—, and the like. Alkyl groups are optionally substituted as described herein.

"Alkenyl" as used herein, unless otherwise indicated, refers to a straight or branched aliphatic hydrocarbon chain having 2- to 6-carbon atoms and containing at least one carbon-carbon double bond (for example —C═C—, or —C═CH$_2$). Non-exclusive examples of alkenyl include: ethenyl, 1-propenyl, 2-propenyl, isopropenyl, 1-butenyl, 2-butenyl, 3-butenyl, 2-pentenyl, and the like.

"Animal(s)", as used herein, unless otherwise indicated, refers to an individual animal that is a mammal, bird, or fish. Specifically, mammal refers to a vertebrate animal that is human and non-human, which are members of the taxonomic class Mammalia. Non-exclusive examples of non-human mammals include companion animals and livestock. Non-exclusive examples of a companion animal include: dog, cat, llama, and horse. Preferred companion animals are dog, cat, and horse. More preferred is dog. Non-exclusive examples of livestock include: swine, camel, rabbits, goat, sheep, deer, elk, bovine (cattle), and bison. Preferred livestock is cattle and swine. Specifically, bird refers to a vertebrate animal of the taxonomic class Aves. Birds are feathered, winged, bipedal, endothermic, and egg-laying. Non-exclusive examples of bird include, poultry (e.g., chicken, turkey, duck, and geese), all of which are also referred to herein as fowl. Specifically, fish refers to the taxonomic class Chondrichthyes (cartilaginous fishes, e.g., sharks and rays) and Osteichthyes (bony fishes) which live in water, have gills or mucus-covered skin for respiration, fins, and may have scales. Non-exclusive examples of fish include shark, salmon, trout, whitefish, catfish, tilapia, sea bass, tuna, halibut, turbot, flounder, sole, striped bass, eel, yellowtail, grouper, and the like.

"Compounds of the present invention", as used herein, unless otherwise indicated, refers to compounds of Formula (1), geometric isomers, stereoisomers thereof, and veterinarily or pharmaceutically acceptable salts thereof.

"Cycloalkyl", as used herein, unless otherwise indicated, includes fully saturated or partially saturated 3- to 6-membered carbocyclic rings. Non-limiting examples of partially saturated cycloalkyls include: cyclopropene, cyclobutene, cyclopentene, cycloheptene, cyclohepta-1,3-diene, and the like. Non-limiting examples of saturated cycloalkyls include cyclopropyl, cyclobutyl, cyclopentyl, and cyclohexyl. The cycloalkyl group may be attached to the chemical moiety by any one of the carbon atoms within the carbocyclic ring. Further when used in compound words such as alkylcycloalkyl, said alkyl and cycloalkyl moiety has the same meaning as herein defined and may be attached to the chemical moiety by any one of the carbon atoms of the aliphatic chain. Examples of "alkylcycloalkyl" include, methylcyclopropane (—CH$_2$-cyclopropane), ethylcyclopropane (—CH$_2$CH$_2$-cyclopropane), methylcyclobutane (—CH$_2$-cyclobutane), ethylcyclobutane (—CH$_2$CH$_2$-cyclobutane), methylcyclohexane (—CH$_2$-cyclohexane), and the like. The term "$C_0$-$C_6$alkylC$_3$-$C_6$cycloalkyl" is defined analogously to the term "alkyl" and "cycloalkyl. For example, C$_1$alkylC$_3$cycloalkyl is analogous to —CH$_2$cyclopropyl and C$_0$alkylC$_4$cycloalkyl is analogous to cyclobutyl, and the like. Cycloalkyl and alkylcycloalkyl moieties are optionally substituted as described herein.

"E/Z Notation" or "E and Z geometric isomer(s)", as used herein, unless otherwise indicated, refers to the International Union of Pure and Applied Chemistry (IUPAC) preferred method of describing the stereochemistry of double bonds in organic chemistry. It is an extension of cis/trans notation that can be used to describe double bonds having three or four substituents. Following a set of defined rules (Cahn-lngold-Prelog priority rules), each substituent on a double-bond is assigned a priority. If the two groups of higher priority are on opposite sides of the double bond, the bond is assigned the configuration E (from entgegen, the German word for "opposite"). If the two groups of higher priority are on the same side of the double bond, the bond is assigned the configuration Z (from zusammen, the German word for "together").

"Halogen" or "halo", as used herein, unless otherwise indicated, refers to fluorine, chlorine, bromine and iodine. Further, when used in compound words such as "haloalkyl", "haloalkoxy", "haloalkenyl", and "haloalkynyl", said alkyl, alkoxy, alkenyl, and alkynyl may be partially or fully substituted with halogen atoms which may be the same or different and said alkyl, alkoxy, alkenyl, and alkynyl moiety has the same meaning as above and may be attached to the chemical moiety by any one of the carbon atoms of the aliphatic chain. Examples of "haloalkyl" include $F_3C—$, $ClCH_2—$, $CF_3CH_2—$ and $CF_3CCl_2—$, and the like. The term "haloalkoxy" is defined analogously to the term "haloalkyl". Examples of "haloalkoxy" include $CF_3O—$, $CCl_3CH_2O—$, $HCF_2CH_2CH_2O—$ and $CF_3CH_2O—$, and the like. The term "haloalkenyl is defined analogously to the term "haloalkyl" except that the aliphatic chain contains at least one carbon-carbon double bond. Examples of "haloalkenyl" include $CF_3C=C—$, $Cl_3CHC=C—$, $HF_2CHC=C—$ and $F_3CHC=C—$, and the like. The term "haloalkynyl" is defined analogously to the term "haloalkyl" except that the aliphatic chain contains at least one carbon-carbon triple bond. Examples of "haloalkynyl" include $F_3CC≡C—$, $Cl_3CC≡C—$, $F_2HCC≡C—$, and the like.

"Heterocycle", as used herein, unless otherwise indicated, refers to a partially saturated or saturated 3- to 6-membered monocyclic ring containing one or more heteroatoms each independently selected from N, O, and S, preferably from one to three heteroatoms. Non-exclusive examples of heterocycle include oxiranyl, thiaranyl, aziridinyl, oxetanyl, thiatanyl, azetidinyl, tetrahydrofuran, tetrahydrothiophene, pyrrolidinyl, tetrahydropyranyl, piperidinyl, piperazinyl, morpholinyl, tetrahydropyridinyl, 2H-azirine, 2,3-dihydro-azete, 3,4-dihydro-2H-pyrrole, and the like. The term "$C_0$-$C_6$ alkylheterocycle" is defined analogously to the term "alkyl" and "heterocycle" wherein the heterocycle is linked to an aliphatic carbon chain containing 1 to 6 carbon atoms. $C_0$alkylheterocycle is analogous to heterocycle. The heterocycle group may be attached to the chemical moiety by any one of the carbon atoms or heteroatoms (e.g., N, O, and S) within the monocyclic ring. Heterocycles are optionally substituted as described herein.

"Heteroaryl" or "Het", as used herein, unless otherwise indicated, refers to a 5- to 6-membered aromatic monocyclic ring or an 8- to 10-membered fused aromatic ring where said monocyclic- and fused-ring moiety contains one or more heteroatoms each independently selected from N, O, and S, preferably from one to four heteroatoms. Non-exclusive examples of monocyclic heteroaryls include pyrrolyl, furanyl, thiophenyl, pyrazolyl, imidazolyl, triazolyl, tetrazolyl, thiazolyl, isoxazolyl, oxazolyl, oxadiazolyl, thiadiazolyl, pyridinyl, pyridazinyl, pyrimidinyl, pyrazinyl, and the like. Non-exclusive examples of fused heteroaryls include: benzofuranyl, benzothiophenyl, indolyl, benzimidazolyl, indazolyl, benzotriazolyl, thieno[2,3-c]pyridine, thieno[3,2-b]pyridine, benzo[1,2,5]thiadiazole, and the like. The term "$C_0$-$C_6$ alkylheteroaryl" is defined analogously to the term "alkyl" and "heteroaryl" wherein the heteroaryl is linked to an aliphatic carbon chain containing 1 to 6 carbon atoms. $C_0$alkylheteroaryl is analogous to heteroaryl. The heteroaryl group may be attached to the chemical moiety by any one of the carbon atoms or heteroatoms (e.g., N, O, and S) within the monocyclic or fused ring. Heteroaryls are optionally substituted as described herein.

"Optionally substituted", is used herein interchangeably with the phrase substituted or unsubstituted. Unless otherwise indicated, an optionally substituted group may have a substituent at each substitutable position of the group, and each substitution is independent of the other. An optionally substituted group also may have no substituents. Therefore, the phrase "optionally substituted with at least one substituent" means that the number of substituents may vary from zero up to a number of available positions for substitution.

"Parasite(s)", as used herein, unless otherwise indicated, refers to endoparasites and ectoparasites. Endoparasites are parasites that live within the body of its host and include helminths (e.g., trematodes, cestodes, and nematodes) and protozoa. Ectoparasites are organisms of the Arthropoda phylum (e.g., arachnids, insects, and crustaceans (e.g., copepods-sea lice) which feed through or upon the skin of its host. Preferred arachnids are of the order Acarina, e.g., ticks and mites. Preferred insects are midges, fleas, mosquitos, biting flies (stable fly, horn fly, blow fly, horse fly, and the like) and lice. Preferred compounds of the present invention can be used for the treatment of parasites, i.e., treatment of a parasitic infection or infestation.

"Therapeutically effective amount", as used herein, unless otherwise indicated, refers to an amount of the compounds of the present invention that (i) treat the particular parasitic infection or infestation, (ii) attenuates, ameliorates, or eliminates one or more symptoms of the particular parasitic infection or infestation, or (iii) prevents or delays the onset of one or more symptoms of the particular parasitic infection or infestation described herein.

"Treatment", "treating", and the like, as used herein, unless otherwise indicated, refers to reversing, alleviating, or inhibiting the parasitic infection, infestation, or condition. As used herein, these terms also encompass, depending on the condition of the animal, preventing the onset of a disorder or condition, or of symptoms associated with a disorder or condition, including reducing the severity of a disorder or condition or symptoms associated therewith prior to affliction with said infection or infestation. Thus, treatment can refer to administration of the compounds of the present invention to an animal that is not at the time of administration afflicted with the infection or infestation. Treating also encompasses preventing the recurrence of an infection or infestation or of symptoms associated therewith as well as references to "control" (e.g., kill, repel, expel, incapacitate, deter, eliminate, alleviate, minimize, and eradicate).

"Veterinary acceptable" as used herein, unless otherwise indicated, indicates that the substance or composition must be compatible chemically and/or toxicologically, with the other ingredients comprising a formulation, composition, and/or the animal being treated therewith. The term "pharmaceutically" acceptable has the same meaning as that recited for "veterinarily" acceptable.

DETAILED DESCRIPTION

The present invention provides Formula (1) compounds, geometric isomers, stereoisomers thereof, as well as veterinary compositions that are useful as antiparasitic agents for animals, in particular, compounds that act as ectoparasiticides.

Compounds of the present invention may be synthesized by synthetic routes that include processes analogous to those well known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, "Reagents for Organic Synthesis", 1; 19, Wiley, New York (1967, 1999 ed.), or *Beilsteins Handbuch der organis-* chen Chemie, 4, Aufl. ed. Springer-Verlag, Berlin, including supplements (also available via the Beilstein online database)).

Compounds of this invention can exist as one or more stereoisomers. The various stereoisomers include enantiomers, diastereomers and atropisomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereo isomers or as an optically active form. For example, two possible enantiomers of Formula 1 are depicted as Formula 1a and Formula 1b involving the isoxazoline chiral center identified with an asterisk (*). Molecular depictions drawn herein follow standard conventions for depicting stereochemistry. The compounds of Formula (1) also contain the oxime double bond which gives rise to the E/Z geometric isomers.

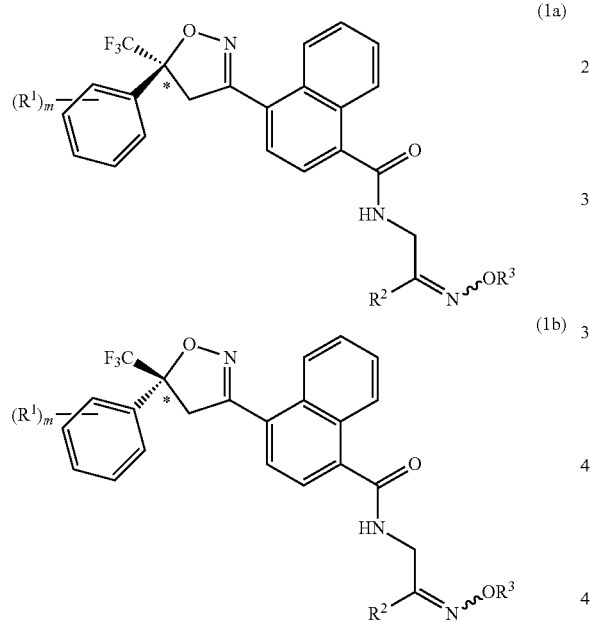

For illustrative purposes, the reaction schemes depicted below demonstrate potential routes for synthesizing key intermediates and Formula (1) compounds. For a more detailed description of the individual reaction steps, see the Examples section below. Those skilled in the art will appreciate that other suitable starting materials, reagents, and synthetic routes may be used to synthesize the intermediates and compounds of the present invention and a variety of derivatives thereof. Further, many of the compounds prepared by the methods described below can be further modified in light of this disclosure using conventional chemistry. Schemes 1-3 outline the general procedures useful for the preparation of compounds of the present invention. It is to be understood, however, that the invention, as fully described herein and as recited in the claims, is not intended to be limited by the details of the following schemes or modes of preparation.

In the Schemes, Procedures, and Examples below, the following catalysts/reactants include: N,N-dimethyl formamide (DMF); trifluoroacetic acid (TFA); N—N-dimethylsulfoxide (DMSO); N-chloro-succinimide (NCS); ethanol (EtOH); N-methylpyrrolidone (NMP), methanol (MeOH), tetrahydrofuran (THF); N-bromosuccinimide (NBS); sodium hydroxide (NaOH); lithium hydroxide (LiOH); potassium bicarbonate ($KHCO_3$); toluene ($PhCH_3$); sodium bicarbonate ($NaHCO_3$); sodium carbonate ($Na_2CO_3$); sodium sulfate ($Na_2SO_4$); sulfuric acid ($H_2SO_4$); 4,4'-di-tert-butyl-2,2'-bipyridine-hexafluorobenzene (dtbpy); 2-2'-azobis(2-methylpropionitrile) (AIBN); dichloromethane ($CH_2Cl_2$); ammonium hydroxide ($NH_2OH$); hydrochloric acid (HCl); potassium acetate (KOAc); deuterated chloroform ($CDCl_3$); triethylamine ($Et_3N$); ethyl acetate (EtOAc); bis(triphenylphosphine) palladium II chloride ($PdCl_2(PPh_3)_2$) from Strem; 1,1'-bis(diphenylphosphino)-ferrocene-palladium(II)dichloride ($Pd(dppf)_2Cl_2$); N,N,N',N'-tetramethyl-O-(7-azabenzotriazol-1-yl)uronium hexafluorophosphate (HATU); 1-hydroxybenzotriazole hydrate (HOBt); ozone ($O_3$); room temperature (rt), bis(pinacolato)diboron ($B_2pin_2$); Dess Martin (periodinane, DMP, 1,1,1-triacetoxy-1,1-dihydro-1,2-benziodoxol-3(1H)-one); and methoxy(cyclooctadiene)iridium(1) dimer ([IRCOD]$_2$) from Alfa Aesar (Ward Hill, Mass.).

The desired aryl oximes can be prepared as shown in Schemes 1-3.

Scheme 1: Preparation of naphthoic acid

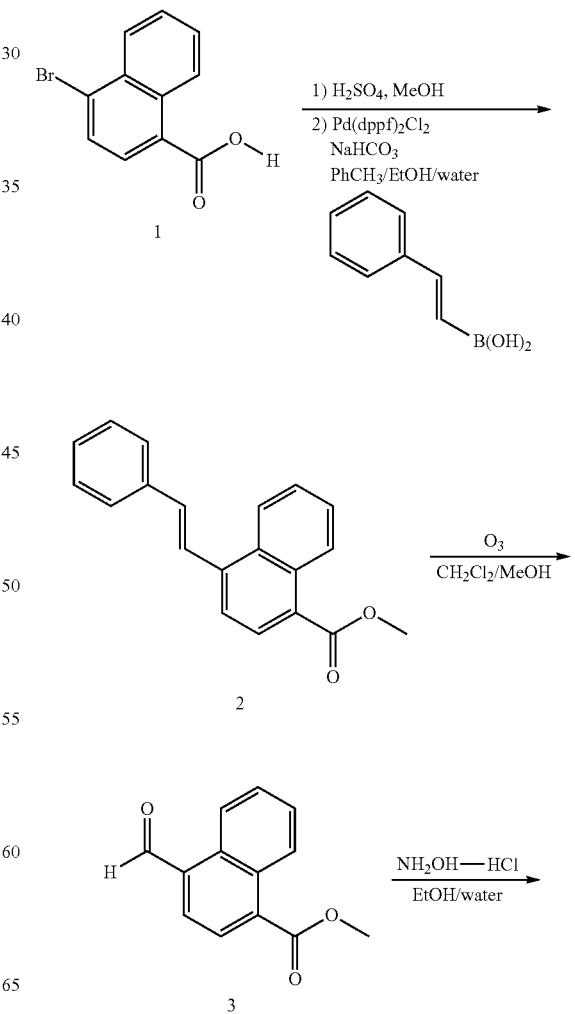

-continued

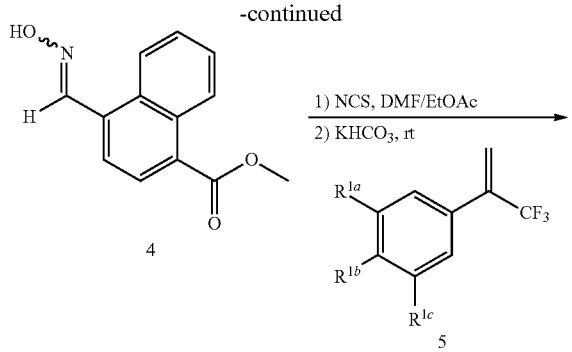

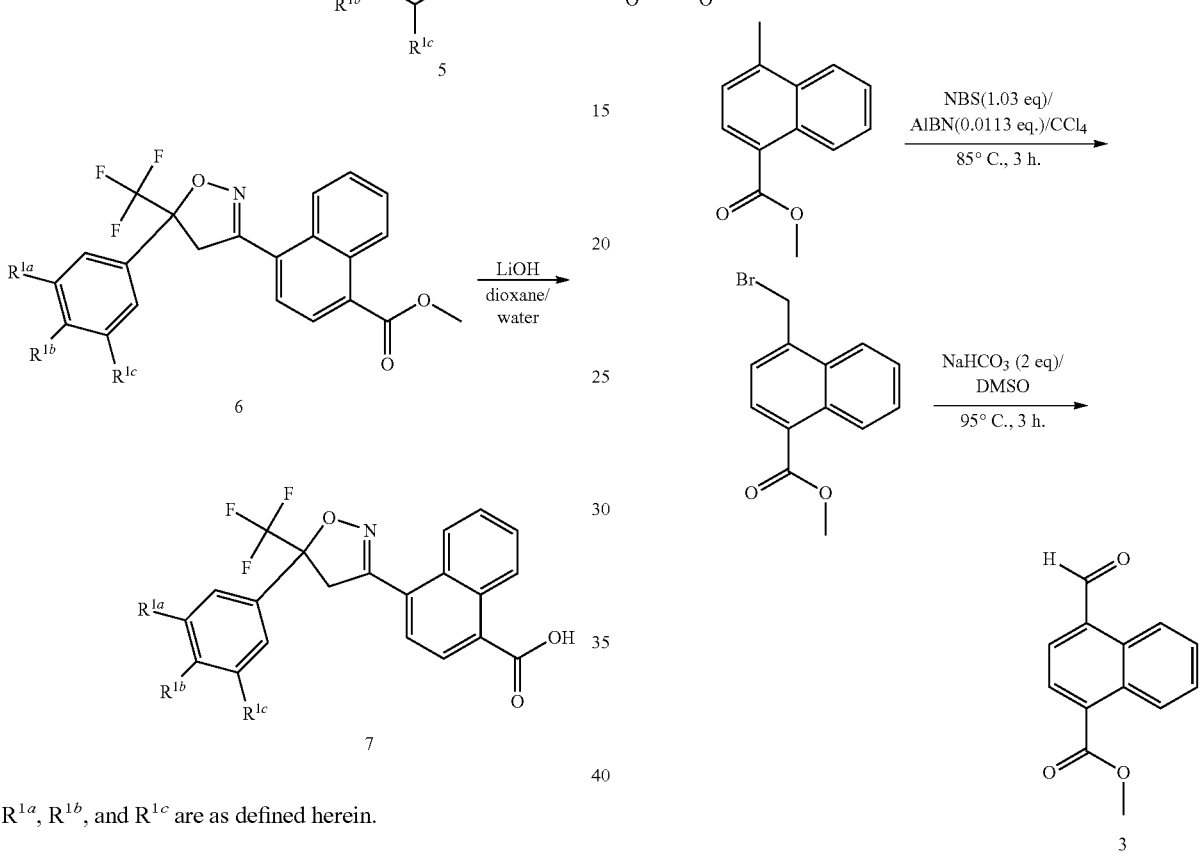

R[1a], R[1b], and R[1c] are as defined herein.

In Scheme 1, intermediate (2), (E)-methyl 4-styryl-1-naphthoate can be prepared by reacting commercially available 4-bromo naphthoic acid (1, Combi Blocks, San Diego, Calif.) with methanol in the presence of catalytic sulfuric acid followed by coupling with trans-2-phenylvinyl-boronic acid in EtOH/toluene with a palladium source (e.g., Pd(dppf$_2$)Cl$_2$) and an inorganic base such as NaHCO$_3$. Ozonolysis can be performed on intermediate 2 in a solvent system such as dichloromethane/MeOH to provide the aldehyde 3, methyl 4-formyl-1-naphthoate. The oxime, (E/Z)-methyl 4-((hydroxyimino)methyl)-1-naphthoate (4) can be synthesized by reacting hydroxylamine hydrochloric acid with the precursor aldehyde (3) in a protic solvent such as ethanol (EtOH). The oxime is converted to the isoxazoline in a two step, one reaction pot procedure. Conversion of the oxime to the chloro-oxime with N-chlorosuccinamide in DMF and subsequent cyclization with the aryl olefin 5 (as shown below in Scheme 3A/3B) affords the desired isoxazoline intermediate 6 compounds. Saponification of the intermediate 6 compounds using a base such as LiOH or NaOH in a solvent system such as dioxane/water can be used to afford the naphthoic acid compounds (7) after acidic work-up.

Treatment of commercially available 4-methylnaphthoic acid with methyl iodide and potassium carbonate provides the methyl ester. Allylic bromination of the methyl group can be accomplished by treatment with N-bromosuccinimide (NBS) in the presence of catalytic AIBN (2-2'-azobis(2-methylpropionitrile). Oxidation of the allylic bromide with sodium bicarbonate and DMSO provides the aldehyde 3.

Scheme 2: Preparation of oximes from naphthoic acid

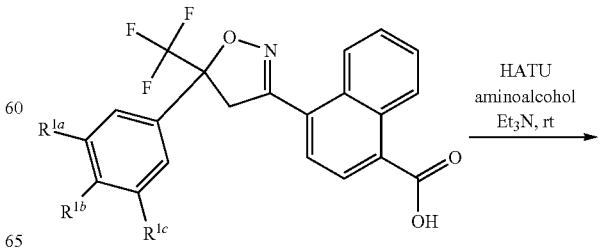

19

-continued

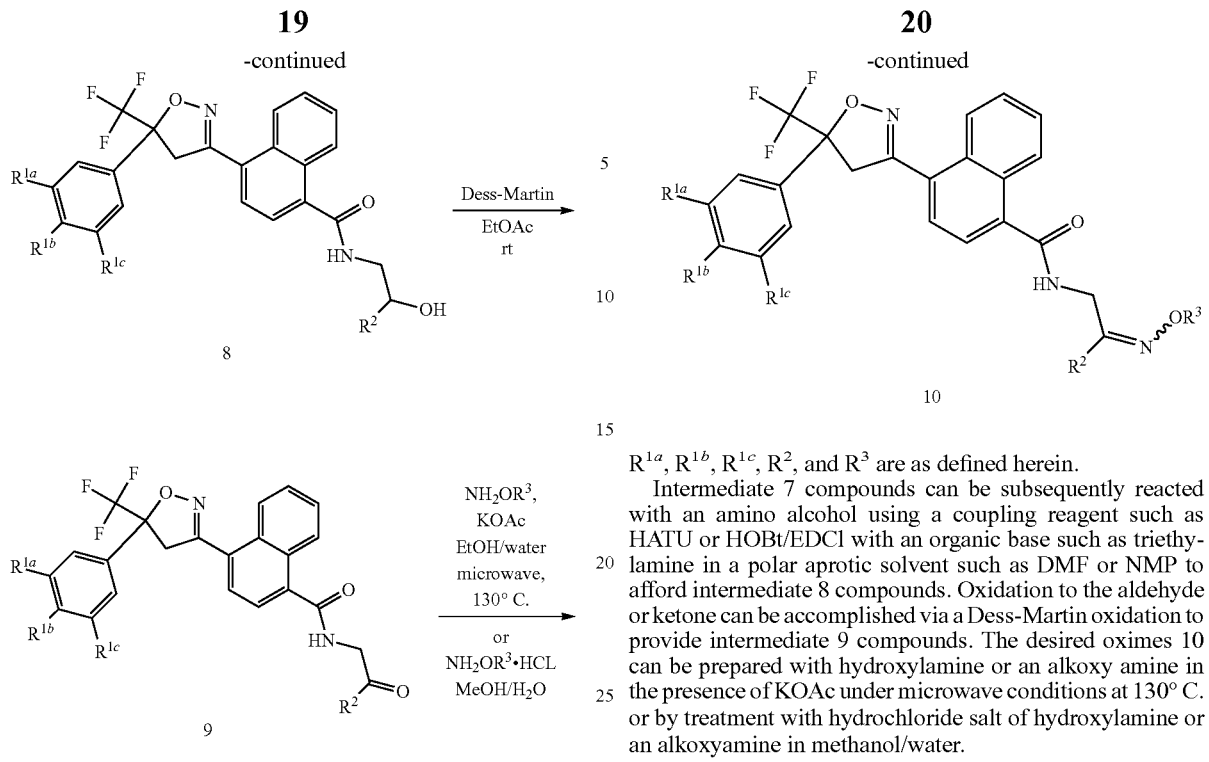

$R^{1a}$, $R^{1b}$, $R^{1c}$, $R^2$, and $R^3$ are as defined herein.

Intermediate 7 compounds can be subsequently reacted with an amino alcohol using a coupling reagent such as HATU or HOBt/EDCl with an organic base such as triethylamine in a polar aprotic solvent such as DMF or NMP to afford intermediate 8 compounds. Oxidation to the aldehyde or ketone can be accomplished via a Dess-Martin oxidation to provide intermediate 9 compounds. The desired oximes 10 can be prepared with hydroxylamine or an alkoxy amine in the presence of KOAc under microwave conditions at 130° C. or by treatment with hydrochloride salt of hydroxylamine or an alkoxyamine in methanol/water.

Scheme 3A/3B: Preparation of aryl olefin (Intermediate 5) compounds

3A

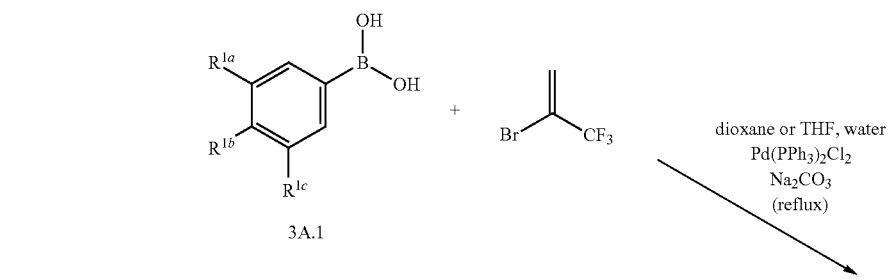

or

3B

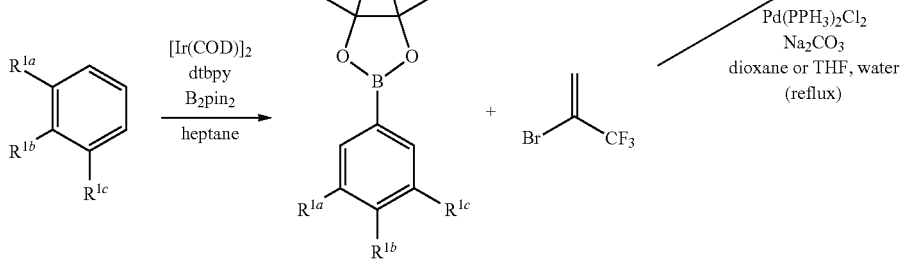

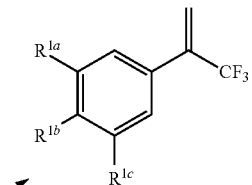

$R^{1a}$, $R^{1b}$, and $R^{1c}$ are as defined herein.

Scheme 3A/3B describes the synthesis of intermediate 5 compounds. The requisite organoborates can be prepared as boronate ester intermediates (3B.2) from literature methods (Org. Lett. 2007, 9, 761-764) or purchased as boronic acids (3A.1) such as 3,5-dichloroboronic acid from Aldrich. Intermediate 3A.1 or 3B.2 compounds can be added to dioxane or THF and water, followed by 2-bromo-3,3,3-trifluoropropene, potassium carbonate, and bis(triphenylphosphine) palladium II chloride to afford intermediate (5) compounds.

One skilled in the art will also recognize that Formula (1) compounds and the intermediates described herein can be subjected to various electrophilic, nucleophilic, radical, organometallic, oxidation, and reduction reactions to add substituents or modify existing substituents.

The present invention includes all pharmaceutically or veterinarily acceptable isotopically-labelled Formula (1) compounds wherein one or more atoms are replaced by atoms having the same atomic number, but an atomic mass or mass number different from the atomic mass or mass number usually found in nature.

Examples of isotopes suitable for inclusion in the compounds of the present invention include isotopes of hydrogen, such as $^{2}H$ and $^{3}H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, and sulphur, such as $^{35}S$.

The skilled person will appreciate that the compounds of the present invention could be made by methods other than those herein described as incorporated herein by reference, by adaptation of the methods herein described and/or adaptation of methods known in the art, for example the art described herein, or using standard textbooks such as "Comprehensive Organic Transformations—A Guide to Functional Group Transformations", RC Larock, Wiley-VCH (1999 or later editions).

The Formula (1) compounds are useful as ectoparasitic and endoparasitic agents, therefore, another embodiment of the present invention is a veterinary or pharmacueitcal composition comprising a therapeutically effective amount of a Formula (1) compound, geometric isomer, stereoisomer thereof, and a veterinarily or pharmaceutically acceptable excipient, diluent or carrier. The compounds of the present invention (including the compositions and processes used therein) may also be used in the manufacture of a medicament for the therapeutic applications described herein.

A typical formulation is prepared by mixing a Formula (1) compound with a pharmaceutically or veterinarily acceptable carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe to be administered to an animal. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a Formula (1) compound or pharmaceutical or veterinary composition thereof) or aid in the manufacturing of the veterinary or pharmaceutical product (i.e., medicament).

The formulations can be prepared using conventional dissolution and mixing procedures. Such compositions and methods for their preparation may be found, for example, in 'Remington's Veterinary Sciences', 19th Edition (Mack Publishing Company, 1995; and "Veterinary Dosage Forms: Tablets, Vol. 1", by H. Lieberman and L. Lachman, Marcel Dekker, N.Y., 1980 (ISBN 0-8247-6918-X). For example, the bulk drug substance (i.e., compound of the present invention or stabilized form of the compound (e.g., complex with a cyclodextrin derivative or other known complexation agent)) is dissolved in a suitable solvent in the presence of one or more other excipients. The compounds of the present invention are typically formulated into veterinary or pharmaceutical dosage forms to provide an easily controllable dosage form for administration. Compounds of the present invention can also be admixed with feed.

The compounds may be administered alone or in a formulation appropriate to the specific use envisaged, the particular species of host animal being treated and the parasite involved. Generally, they will be administered as a formulation in association with one or more veterinarily or pharmaceutically acceptable salts, excipients, diluents, or carriers. The term "excipient", "diluent" or "carrier" is used herein to describe any ingredient other than the Formula (1) compounds or any additional antiparasitic agent. The choice of excipient, diluent, or carrier will to a large extent depend on factors such as the particular mode of administration, the effect of the excipient, carrier, or diluent on solubility and stability, nature of the dosage form, and animal specie.

The methods by which the compounds of the present invention may be administered include oral, topical, and injectable (subcutaneous, intraperitoneal, and intramuscular) administration. The preferred method for injection is either subcutaneous or intramuscular. The most preferred method for injection is subcutaneous injection.

The Formula (1) compounds can be administered orally by capsule, bolus, tablet, powders, lozenges, chews, multi and nanoparticulates, gels, solid solution, films, sprays, liquid form, or admixed with food. Oral administration is a preferred method of administration and as such it is desirable to develop active Formula (1) compounds that are particularly suited to such formulations. Such formulations may be employed as fillers in soft or hard capsules, tablets, or chews, and typically comprise a carrier, for example, water, ethanol, polyethylene glycol, N-methylpyrrolidone, propylene glycol, methylcellulose, or a suitable oil, and one or more emulsifying agents and/or suspending agents. Liquid forms include suspensions, solutions, syrups, drenches and elixirs. Liquid formulations may also be prepared by the reconstitution of a solid, for example, from a sachet. Oral drenches are commonly prepared by dissolving or suspending the active ingredient in a suitable medium. Feed admixtures can be prepared for livestock and fish. Oral formulations can comprise from about 0.5 mg/kg to 50 mg/kg of a Formula (1) compound, and preferably about 1 mg/kg to 30 mg/kg of a Formula (1) compound. Depending upon the host specie treated and the parasite being treated, dose adjustments can be made.

The compounds may be administered topically to the skin or mucosa, that is dermal or transdermal application. This is a preferred method of administration and as such it is desirable to develop active Formula (1) compounds that are particularly suited to such formulations, for example liquid forms. Typical formulations for this purpose include pour-on, spot-on, multi-spot-on, stripe-on, comb-on, roll-on, dip, spray, mousse, shampoo, powder formulation, gels, hydrogels, lotions, solutions, creams, ointments, dusting powders, dressings, foams, films, skin patches, wafers, implants, sponges, fibers, bandages and micro emulsions. Liposomes may also be used. Typical carriers include alcohol, water, mineral oil, liquid petrolatum, white petrolatum, glycerin, N-methyl formamide, glycol monomethyl ethers, polyethylene glycol, propylene glycol, and the like. Penetration enhancers may be incorporated—see, for example, J Pharm Sci, 88 (10), 955-958 by Finnin and Morgan (October 1999). Pour-on or spot-on formulations may be prepared by dissolving the active ingredients in an acceptable liquid carrier vehicle such as butyl digol, liquid paraffin or a non-volatile ester, optionally with the addition of a volatile component such as propan-2-ol or a glycol ether. Alternatively, pour-on, spot-on or spray formulations can be prepared by encapsulation, to leave a residue of active agent on the surface of the animal, this effect may ensure that the Formula (1) compounds have increased persistence of action and are more durable, for example they may be more water fast. Topical formulations of the combination contemplated herein can comprise from about 0.5 mg/kg to 50 mg/kg of a Formula (1) compound, and preferably about 1 mg/kg to 10 mg/kg of a Formula (1) compound. The compositions suitable for spot-on application according to the invention can be prepared by conventional mixing means. The volume of the applied composition can be from about 0.5 mL/kg to 5 mL/kg and preferably from about 1 mL/kg to 3 mL/kg. Similarly, dose can be adjusted.

The compounds of the present invention can also be administered topically via a support matrix for example, a synthetic or natural resin, plastic, cloth, leather, or other such polymeric system in the shape of a collar or ear tag. Said collar or ear tag may be coated, impregnated, layered, by any means so as to provide a veterinarily or pharmaceutically acceptable amount of a compound of the present invention alone, or with a veterinarily or pharmaceutically acceptable excipient, diluent, or carrier, and optionally an additional veterinary agent, or veterinarily or pharmaceutically acceptable salt thereof.

Agents may be added to the formulations of the present invention to improve the persistence of such formulations on the surface of the animal to which they are applied, for example to improve their persistence on the coat of the animal. It is particularly preferred to include such agents in a formulation which is to be applied as a pour-on or spot-on formulation. Examples of such agents include acrylic copolymers and in particular fluorinated acrylic copolymers. A particular suitable reagent is the trademark reagent "Foraperle" (Redline Products Inc, Texas, USA). Certain topical formulations may include unpalatable additives to minimize oral exposure.

Injectable formulations may be prepared in the form of a sterile solution, which may contain other substances, for example enough salts or glucose to make the solution isotonic with blood. Acceptable liquid carriers include vegetable oils such as sesame oil, glycerides such as triacetin, esters such as benzyl benzoate, isopropyl myristate and fatty acid derivatives of propylene glycol, as well as organic solvents such as pyrrolidin-2-one and glycerol formal. The formulations are prepared by dissolving or suspending compounds of the present invention alone or with an additional veterinary agent in the liquid carrier such that the final formulation contains from about 0.01 to 50% by weight of the active ingredients, preferably from about 0.01% to about 10% by weight of the active ingredients.

Suitable devices for injection include needle (including micro needle) injectors, needle-free injectors and infusion techniques. Subcutaneous formulations are typically aqueous solutions which may contain excipients such as salts, carbohydrates and buffering agents (preferably to a pH of from 3 to 9), but, for some applications, they may be more suitably formulated as a sterile non-aqueous solution or as a dry powder form to be used in conjunction with a suitable vehicle such as sterile, pyrogen-free water. The preparation of subcutaneous formulations under sterile conditions, for example, by lyophilisation, may readily be accomplished using standard veterinary techniques well known to those skilled in the art. The solubility of compounds of Formula (1) used in the preparation of subcutaneous solutions may be increased by the use of appropriate formulation techniques, such as the incorporation of solubility-enhancing agents.

Such formulations are prepared in a conventional manner in accordance with standard medicinal or veterinary practice. Further, these formulations will vary with regard to the weight of active compound contained therein, depending on the species of host animal to be treated, the severity and type of infection or infestation, and the body weight of the animal.

For fish, compounds of the present invention can be formulated for oral administration by way of feed admixture. For example, the compounds of the present invention can be formulated in a food product (e.g., pellets) that can be easily dispersed to fish as a feeding agent. Further, a compound of the present invention can be administered topically by immersing the fish into an aqueous environment containing at least one of the compounds of the present invention. For example, fish may be transferred into a tank for treatment or caused to pass from one holding tank or zone into another. The compounds of the present invention may also be administered directly to the water containing the fish. The compound of the present invention can be in any dispersible formulation such that upon introduction to water the compound dissolves into the solution. Alternatively, the compounds of the present invention can be administered by injection. Preferable injection routes for treatment of fish are intraparitoneal or intramuscular. The injectable formulations include any liquid suspension, such as oils, aqueous solutions, or oil and water emersions. The compounds of the present invention can also be co-administered with additional agents, antigens, adjuvants, carriers, diluents or nutrients.

The Formula (1) compounds are also active against all or individual developmental stages of animal pests showing normal sensitivity, as well as those showing resistance to widely used parasiticides.

As described herein, compounds of the present invention may be administered alone or in combination with at least one additional veterinary agent including insecticides, acaricides, anthelmintics, fungicides, nematocides, antiprotozoals, bactericides, and growth regulators to form a multi-component agent giving an even broader spectrum of veterinary utility. Thus, the present invention also pertains to a composition comprising an effective amount of a Formula (1) compound, geometric isomer, a stereoisomer thereof, and an effective amount of at least one additional veterinary agent and can further comprise one or more of a veterinarily or pharmaceutically acceptable excipient, diluent, or carrier.

The following list of additional veterinary agents together with which the compounds of the present invention can be used is intended to illustrate the possible combinations, but not to impose any limitation. Non-limiting examples of additional veterinary agents include: amitraz, arylpyrazoles as recited in publications WO1998/24767 and WO2005/060749, bis-organosulfur compounds of WO2011/069143, 4-amino-thieno[2,3-D]pyrimidines of WO2011/014660, amidoacetonitriles, anthelmintics (e.g., albendazole, cambendazole, fenbendazole, flubendazole, mebendazole, octadepsipeptides, oxfendazole, oxibendazole, paraherquamide (2-desoxoparaherquamide, derquantel), parbendazole, piperazines, praziquantel, thiabendazole, tetramisole, triclabendazole, levamisole, pyrantel pamoate, oxantel, morantel, and the like), indoxacarb and derivatives or metabolites thereof, avermectins (e.g., avermectin, abamectin, doramectin, emamectin, eprinomectin, ivermectin, moxidectin, selamectin, and the like), milbemycin, milbemycin oxime, DEET, demiditraz, diethylcarbamazine, fipronil, insect growth regulators (e.g., hydroprene, kinoprene, S-methoprene, pyriproxyfen, and the like), metaflumizone, niclosamide, permethrin, pyrethrins, spinosad, and formamidines (e.g., demiditraz, amitraz, and the like). In certain instances, combinations of a Formula (1) compound with an additional veterinary agent(s) can result in a greater-than-additive effect. Reducing the quantity of active ingredients released in the environment while ensuring effective pest control is always desirable.

It may be desirable to administer a compound of the present invention, stereoisomers thereof, alone or in a composition comprising a veterinarily acceptable excipient, diluent, or carrier, for example, for the purpose of treating a particular parasitic infection or infestation or condition associated therewith. It is within the scope of the present invention that two or more veterinary compositions, at least one of which contains a Formula (1) compound in accordance with the invention, and the other, an additional veterinary agent, may conveniently be combined in the form of a kit suitable for coadministration of the compositions.

The compounds of the present invention (including the compositions and processes used therein) may also be used in the manufacture of a medicament for the therapeutic applications described herein.

The compounds of the present invention, geometric isomers, stereoisomers thereof, and compositions comprising a therapeutically effective amount of a Formula (1) compound and a veterinarily acceptable excipient, diluent, or carrier are useful as parasiticides (endo- and ecto-parasites) for the control and treatment of infections or infestations manifested by said parasite in an animal. The compounds of the present invention have utility as an ectoparasiticide, in particular, as an acaricide and insecticide. They may, in particular, be used in the fields of veterinary medicine, livestock husbandry, fish farming, and the maintenance of public health: against acarids and insects which are parasitic upon vertebrates, particularly warm-blooded vertebrates, including companion animals, livestock, and birds. The compounds of the present invention are also parasiticides for cold-blooded fish. Some non-limiting examples of acaride and insect parasites include: ticks (e.g., *Ixodes* spp., *Rhipicephalus* spp., *Boophilus* spp., *Amblyomma* spp., *Hyalomma* spp., *Haemaphysalis* spp., *Dermacentor* spp., *Ornithodorus* spp., and the like); mites (e.g., *Dermanyssus* spp., *Sarcoptes* spp., *Psoroptes* spp., *Chorioptes* spp., *Demodex* spp., and the like); chewing and sucking lice (e.g., *Damalinia* spp., *Linognathus* spp., and the like); fleas (e.g., *Siphonaptera* spp., *Ctenocephalides* spp., and the like); and biting flies and midges (e.g., *Tabanidae* spp., *Haematobia* spp., *Stomoxys* spp., *Dermatobia* spp., *Simuliidae* spp., *Ceratopogonidae* spp., *Psychodidae* spp., and the like). In another example, ectoparasites of the crustacean order copepod, more particularly of the genera *Lepeophtheirus* (especially the salmon louse, *Lepeoptheirus salmonis*) and/or *Caligus* (e.g., *C. elongates, C. rogercreysii, C. teres, C. flexispina*, and the like), particularly sea lice, can be treated with a compound of the present invention. The compounds of the invention can also be used for the treatment of endoparasites, for example, heartworms, roundworms, hookworms, whipworms, and tapeworms.

The compounds of the present invention and compositions comprising compounds of the present invention in conjunction with at least one other veterinary agent are of particular value in the control of ectoparasites, endoparasites, and insects which are injurious to, or spread or act as vectors of diseases in animals. The ectoparasites, insects, and endoparasites which can be treated with a combination of a Formula (1) compound and an additional veterinary agent include those as herein before described and including helminthes of the phylum platyhelminthes (e.g., trematodes, eucestoda, and cestoda), and nemathelminthes (e.g., nematodes).

Any of the compounds of the present invention, or a suitable combination of a compound of the present invention and optionally, with at least one additional veterinary agent may be administered directly to the animal and/or indirectly by applying it to the local environment in which the animal dwells. Direct administration includes contacting the skin, fur, or feathers of a subject animal or bird with the compound(s), or by feeding or injecting the compounds into the animal or bird.

The Formula (1) compounds, geometric isomers, stereoisomers thereof, and combinations with at least one additional veterinary agent, as described herein, are of value for the treatment and control of the various lifecycle stages of insects and parasites including egg, nymph, larvae, juvenile and adult stages.

The present invention also relates to a method of administering a compound of the present invention alone or in combination with at least one additional veterinary agent, and optionally a veterinarily or pharmaceutically acceptable excipient, diluent, or carrier, to animals in good health comprising the application to said animal to reduce or eliminate the potential for human parasitic infection or infestation from parasites carried by the animal and to improve the environment in which the animal and human inhabit.

The reactions set forth below were done generally under a positive pressure of argon or nitrogen or with a drying tube, at ambient temperature (unless otherwise stated), in anhydrous solvents, and the reaction flasks were fitted with rubber septa for the introduction of substrates and reagents via syringe. Glassware was oven dried and/or heat dried. Analytical thin layer chromatography (TLC) was performed using glass-backed silica gel 60 F 254 precoated plates and eluted with appropriate solvent ratios (v/v). Reactions were assayed by TLC or LCMS and terminated as judged by the consumption of starting material. Visualization of the TLC plates was done with UV light (254 nM wavelength) or with an appropriate TLC visualizing solvent and activated with heat. Flash column chromatography (Still et al., *J. Org. Chem.* 43, 2923, (1978) was performed using silica gel (RediSep Rf) or various MPLC systems, such as Biotage or ISCO purification system.

Conventional methods and/or techniques of separation and purification known to one of ordinary skill in the art can be used to isolate the compounds of the present invention, as well as the various intermediates related thereto. Such techniques will be well-known to one of ordinary skill in the art and may include, for example, all types of chromatography (high pressure liquid chromatography (HPLC), column chromatography using common adsorbents such as silica gel, and thin-layer chromatography (TLC), recrystallization, and differential (i.e., liquid-liquid) extraction techniques.

The compound structures in the examples below were confirmed by one or more of the following methods: proton magnetic resonance spectroscopy, and mass spectroscopy. Proton magnetic resonance ($^1$H NMR) spectra were determined using a Bruker spectrometer operating at a field strength of 400 megahertz (MHz). Chemical shifts are reported in parts per million (PPM, δ) downfield from an internal tetramethylsilane standard. Mass spectra (MS) data were obtained using Agilent mass spectrometer with atmospheric pressure chemical ionization. Method: Acquity HPLC with chromatography performed on a Waters BEH C18 column (2.1×50 mm, 1.7 µm) at 50° C. The mobile phase was a binary gradient of acetonitrile (containing 0.1% trifluoroacetic acid) and water (5-100%).

Embodiments of the present invention are illustrated by the following Examples. It is to be understood, however, that the embodiments of the invention are not limited to the specific details of these Examples, as other variations thereof will be known, or apparent in light of the instant disclosure, to one of ordinary skill in the art.

EXAMPLES

One skilled in the art will also recognize that Formula (1) compounds and the intermediates described herein can be subjected to various electrophilic, nucleophilic, radical, organometallic, oxidation, and reduction reactions to add substituents or modify existing substituents.

The following examples provide a more detailed description of the process conditions. It is to be understood, however, that the invention, as fully described herein and as recited in the claims, is not intended to be limited by the details of the following schemes or modes of preparation.

Preparation 1: methyl 4-bromo-1-naphthoate

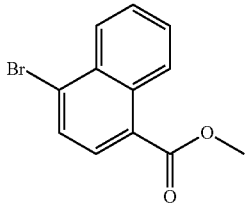

To a solution of 4-bromo naphthoic acid (4.0 g, 15.9 mmol) in MeOH (75 mL) was added sulfuric acid (0.5 mL) and the reaction was heated to reflux for 18 hours. TLC 50:50 EtOAc:heptane showed consumption of starting material. The reaction was cooled and concentrated under vacuum to remove MeOH. The residue was diluted with EtOAc (150 mL), washed with water (100 mL), diluted with saturated NaHCO$_3$ (100 mL), dried over Na$_2$SO$_4$ and concentrated under vacuum to afford a solid (3.85 g, 91%). $^1$H NMR (CDCl$_3$) δ ppm: 8.96 (1H), 8.36 (1H), 8.02 (1H), 7.85 (1H), 7.70-7.66 (2H), 4.03 (3H).

Preparation 2: (E)-methyl 4-styryl-1-naphthoate

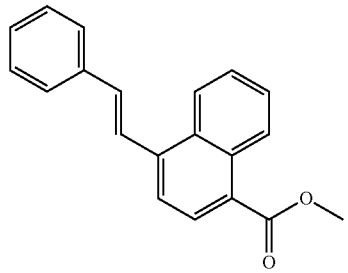 [SMILES: COC(=O)c1ccc(/C=C/c2ccccc2)c2ccccc12]

To a solution of methyl 4-bromo-1-naphthoate, (Preparation 1, 5.4 g, 20.4 mmol) in ethanol (50 mL) and toluene (50 mL) was added Pd(dppf)$_2$Cl$_2$ (760 mg, 1.0 mmol), trans-2-phenylvinylboronic acid (3.3 g, 22.4 mmol) and sodium bicarbonate aqueous solution (40 mL of 2M solution). The mixture was heated to reflux for 3 hours. The mixture was cooled to room temperature and diluted with EtOAc (150 mL) and water (75 mL). The organic phase was separated, washed with brine (50 mL), dried over sodium sulfate, and concentrated. The residue was purified by chromatography on silica gel eluting from 10:90 EtOAc:heptane to 50:50 EtOAc:heptane to afford an oil which solidified upon standing (5.3 g, 90%).

$^1$H NMR (CDCl$_3$) δ ppm: 9.02 (1H), 8.30 (1H), 8.22 (1H), 7.91 (1H), 7.77 (1H), 7.67-7.60 (4H), 7.45 (2H), 7.36 (1H), 7.24 (1H), 4.04 (3H).

Preparation 3: methyl 4-formyl-1-naphthoate

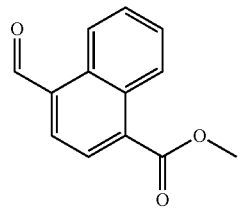 [SMILES: COC(=O)c1ccc(C=O)c2ccccc12]

A solution of (E)-methyl 4-styryl-1-naphthoate (Preparation 2, 1.31 g, 2.0 mmol) in 3:1 CH$_2$Cl$_2$/MeOH (40 mL) was cooled to −78° C. Sample was subjected to ozonylysis for 10 minutes until blue color was noted. Reaction was quenched with dimethyl sulfide (400 µL) and allowed to warm to room temperature. The residue was purified by chromatography on silica gel eluting from 100% heptane to 50:50 EtOAc:heptane to afford a solid (0.78 g, 80%). $^1$H NMR (CDCl$_3$) δ ppm: 10.52 (1H), 9.28 (1H), 8.83 (1H), 8.22 (1H), 8.04 (1H), 7.79-7.70 (2H), 4.08 (3H).

Preparation 4: (E/Z)-methyl 4-((hydroxyimino)methyl)-1-naphthoate

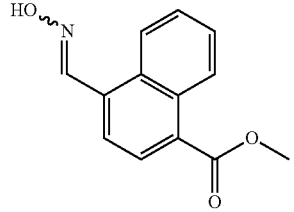 [SMILES: COC(=O)c1ccc(C=NO)c2ccccc12]

To a solution of methyl 4-formyl-1-naphthoate (Preparation 3, 3.1 g, 14.5 mmol) in ethanol (125 mL) was added NH$_2$OH.HCl (2.05 g, 29 mmol) and water (20 mL). The solution was heated to 45° C. for 18 hours. The reaction was cooled and concentrated under vacuum to remove ethanol. Water (100 mL) was added to the residue and extracted with CH$_2$Cl$_2$ (2×125 mL). The combined organic phases were dried (Na$_2$SO$_4$) and concentrated under vacuum. The crude intermediate was purified by chromatography on silica gel eluting from 100% heptane to 50:50 EtOAc:heptane to afford a solid (1.82 g, 55%). MS m/z (CI) 230 [M+H]$^+$.

Preparation 5: (E/Z)-methyl 4-(chloro(hydroxyimino)methyl)-1-naphthoate

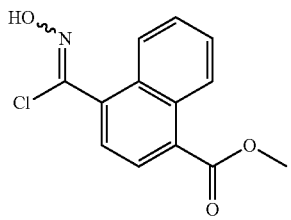 [SMILES: COC(=O)c1ccc(C(Cl)=NO)c2ccccc12]

To a DMF (30 mL) solution of (E/Z)-methyl 4-((hydroxyimino)methyl)-1-naphthoate (Preparation 4, 1.8 g, 7.8 mmol) was added N-chlorosuccinimide (1.05 g, 7.8 mmol) in portions over 10 minutes. The reactants were stirred at room temperature for 3 hours. The reaction mixture was diluted with EtOAc (150 mL) and washed with water (3×75 mL). The organic phase was dried ($Na_2SO_4$) and concentrated under vacuum to afford a solid. $^1$H NMR ($CDCl_3$) δ ppm: 8.92 (1H), 8.40 (1H), 8.26 (1H), 8.17 (1H), 7.73-7.64 (3H), 4.06 (3H).

Preparation 6: methyl 4-(5-(3,5-dichloro-4-fluorophenyl)-5-(trifluoromethyl)-4,5-dihydroisoxazol-3-yl)-1-naphthoate

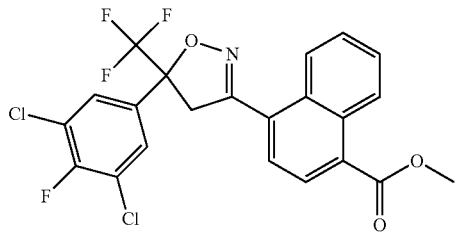 [SMILES: COC(=O)c1ccc(C2=NOC(c3cc(Cl)c(F)c(Cl)c3)(C(F)(F)F)C2)c2ccccc12]

To an EtOAc (25 mL) solution containing (E/Z)-methyl 4-(chloro(hydroxyl-imino)methyl)-1-naphthoate (Preparation 5, 1.95 g, 7.4 mmol) and 1,3-dichloro-2-fluoro-5-(1,1,1-trifluoroprop-2-en-2-yl)benzene (1.92 g, 7.4 mmol) was added potassium bicarbonate (750 mg, 7.4 mmol). The reaction mixture was allowed to stir at room temperature for 18 hours. Next, the reaction mixture was filtered and concentrated under vacuum. The residue was purified by chromatography on silica gel eluting from 10:90 EtOAc:heptane to 50:50 EtOAc:heptane to afford a solid (2.95 g, 82%). $^1$H NMR ($CDCl_3$) δ ppm: 8.91 (1H), 8.81 (1H), 8.12 (1H), 7.72-7.65 (4H), 7.56 (1H), 4.30 (1H), 4.06 (3H), 3.92 (1H).

Preparation 7: 4-(5-(3,5-dichloro-4-fluorophenyl)-5-(trifluoromethyl)-4,5-dihydroisoxazol-3-yl)-1-naphthoic acid

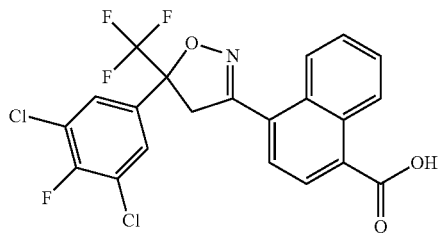 [SMILES: O=C(O)c1ccc(C2=NOC(c3cc(Cl)c(F)c(Cl)c3)(C(F)(F)F)C2)c2ccccc12]

To a 7:1 dioxane:water mixture (80 mL) containing methyl 4-(5-(3,5-dichloro-4-fluorophenyl)-5-(trifluoromethyl)-4,5-dihydroisoxazol-3-yl)-1-naphthoate (Preparation 6, 2.9 g, 5.9 mmol) was added lithium hydroixide (430 mg, 18.0 mmol). The reaction mixture was allowed to stir at room temperature for 3 hours. Thin layer chromatography (TLC) 25:75 EtOAc:heptane showed consumption of starting material. 1N HCl (25 mL) was added. The reaction was partitioned between water (25 mL) and ethyl acetate (150 mL). The organic phase was collected, dried over $Na_2SO_4$, and concentrated under vacuum to give a solid (2.77 g, 98%). $^1$H NMR ($CDCl_3$) δ ppm: 9.10 (1H), 8.82 (1H), 8.34 (1H), 7.76-7.66 (4H), 7.60 (1H), 4.32 (1H), 3.93 (1H).

Preparation 8: 4-(5-(3,5-dichloro-4-fluorophenyl)-5-(trifluoromethyl)-4,5-dihydroisoxazol-3-yl)-N-(2-hydroxyethyl)-1-naphthamide

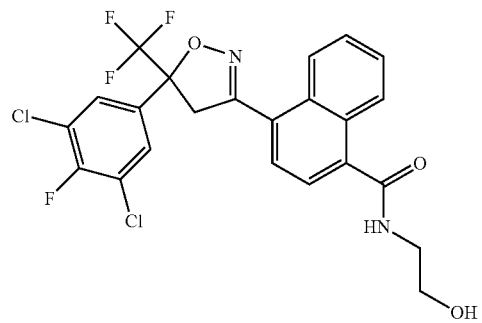 [SMILES: O=C(NCCO)c1ccc(C2=NOC(c3cc(Cl)c(F)c(Cl)c3)(C(F)(F)F)C2)c2ccccc12]

To a solution of 4-(5-(3,5-dichloro-4-fluorophenyl)-5-(trifluoromethyl)-4,5-dihydroisoxazol-3-yl)-1-naphthoic acid (Preparation 7, 1 g, 2.1 mmol) in DMF (35 mL) was added HATU (970 mg, 2.5 mmol) and triethylamine (1.0 mL, 7.0 mmol). The reaction was stirred at room temperature for 15 minutes then treated with 2-amino-ethanol (145 mg, 2.4 mmol). The reaction was stirred at room temperature for 2 hours. Next, the reaction was diluted with 0.1N NaOH and extracted with EtOAc (2×150 mL). The combined organic phase was dried ($Na_2SO_4$) and concentrated under vacuum. The crude material was chromatographed (80 g Redi-Sep column) eluting from 100% heptane to 40:60 EtOAc:heptane to afford the intermediate (734 mg, 67%) as a solid. $^1$HNMR ($CDCl_3$) δ ppm: 8.82 (1H), 8.33 (1H), 7.76-7.60 (5H), 7.50 (1H), 6.51 (1H) 4.28 (1H), 3.94-3.83 (3H), 3.76 (2H), 2.35 (1H); m/z (CI) 515 [M+H]$^+$.

Preparation 9: 4-(5-(3,5-dichloro-4-fluorophenyl)-5-(trifluoromethyl)-4,5-dihydroisoxazol-3-yl)-N-(2-oxoethyl)-1-naphthamide

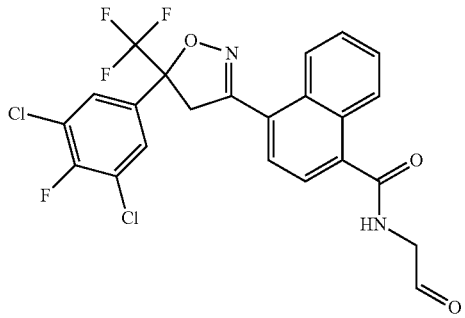 [SMILES: O=CCNC(=O)c1ccc(C2=NOC(c3cc(Cl)c(F)c(Cl)c3)(C(F)(F)F)C2)c2ccccc12]

To a solution of 4-(5-(3,5-dichloro-4-fluorophenyl)-5-(trifluoromethyl)-4,5-dihydroisoxazol-3-yl)-N-(2-hydroxyethyl)-1-naphthamide (Preparation 8, 730 mg, 1.4 mmol) in EtOAc (100 mL) was added Dess-Martin reagent (725 mg, 1.7 mmol). The reaction was stirred at room temperature for 2 hours. TLC 65:35 EtOAc:heptane shows complete conversion to less polar spot. 50 mL $NaHCO_3$ was added to reaction mixture and stirred for 15 minutes. Contents were diluted with water, extracted with EtOAc (2×75 mL), dried (Na₂SO₄), and concentrated under vacuum to afford the intermediate (713 mg, 98%) as a solid. m/z (Cl) 513 [M+H]⁺.

Examples 1 and 2

(E/Z)-4-(5-(3,5-dichloro-4-fluorophenyl)-5-(trifluoromethyl)-4,5-dihydroisoxazol-3-yl)-N-(2-(isopropoxyimino)ethyl)-1-naphthamide

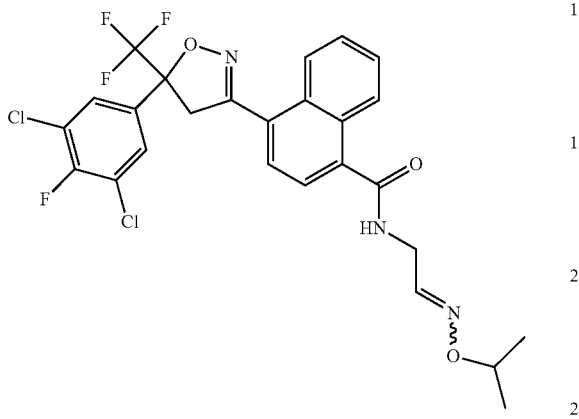

To a solution of 4-(5-(3,5-dichloro-4-fluorophenyl)-5-(trifluoromethyl)-4,5-dihydroisoxazol-3-yl)-N-(2-oxoethyl)-1-naphthamide (Preparation 9, 400 mg, 0.8 mmol) in EtOH (12 mL) was added isopropylhydroxylamine.HCl (200 mg, 1.7 mmol), water (3 mL), and KOAc (185 mg, 1.7 mmol). Reaction was heated to 130° C. for 25 minutes in a microwave. Water was added to the crude reaction and a whitish precipitate formed. The precipitate was filtered and washed with additional water. The crude precipitate was chromatographed (40 g Silia-Sep column) eluting from 100% heptane to 30:70 EtOAc:heptane collecting first eluting isomer (120 mg, 27%) and second eluting isomer (133 mg, 30%) as solids. First eluting isomer (Example 1) ¹HNMR (CDCl₃) δ ppm: 8.83 (1H), 8.31 (1H), 7.75-7.60 (4H), 7.52 (1H), 6.93 (1H), 6.49 (1H), 4.47-4.37 (3H) 4.29 (1H), 3.91 (1H), 1.27 (6H); m/z (Cl) 570 [M+H]⁺. Second eluting isomer (Example 2) ¹HNMR (CDCl₃) δ ppm: 8.84 (1H), 8.38 (1H), 7.72-7.55 (7H), 6.53 (1H) 4.37-4.27 (4H), 3.92 (1H), 1.25 (6H); m/z (Cl) 570 [M+H]⁺.

Example 3

(E/Z)-4-(5-(3,5-dichloro-4-fluorophenyl)-5-(trifluoromethyl)-4,5-dihydroisoxazol-3-yl)-N-(2-(methoxyimino)ethyl)-1-naphthamide

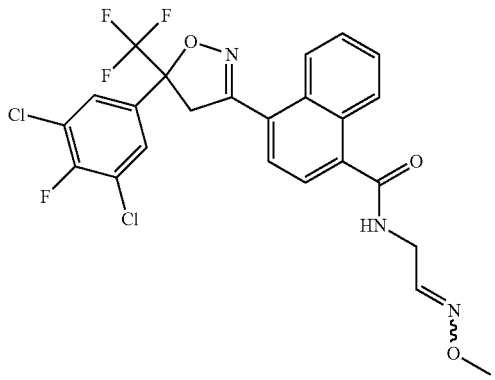 [SMILES: CON=CCNC(=O)c1ccc(C2=NOC(c3cc(Cl)c(F)c(Cl)c3)(C(F)(F)F)C2)c2ccccc12]

To a solution of 4-(5-(3,5-dichloro-4-fluorophenyl)-5-(trifluoromethyl)-4,5-dihydroisoxazol-3-yl)-N-(2-oxoethyl)-1-naphthamide (Preparation 9, 100 mg, 0.20 mol) in EtOH (5 mL) was added methoxyamine.HCl (42.3 mg, 0.52 mmol), water (1 mL), and KOAc (55 mg, 0.53 mmol). Reaction mixture was heated to 130° C. for 20 minutes in a microwave. The solvent was removed under reduced pressure and the residue was purified by preparative SFC purification (Thar MS100, column: 2-Ethyl Pyridine 5 um 30×250 mm 5 um, MP A=CO₂ MP B=MeOH, Gradient 10% B to 45B % in 10 min, 100 bar Backpressure, 100 mL/min) to afford (E/Z)-4-(5-(3,5-dichloro-4-fluorophenyl)-5-(trifluoromethyl)-4,5-dihydroisoxazol-3-yl)-N-(2-(methoxyimino)ethyl)-1-naphthamide (62 mg, 59%) as a mixture of isomers. ¹HNMR (CDCl₃) δ ppm: 8.83 (2H), 8.38-8.29 (2H), 7.72-7.52 (13H), 6.94 (1H), 6.53 (1H), 6.48 (1H), 4.41-4.27 (6H), 3.96-3.88 (8H); m/z (Cl) 542 [M+H]⁺.

Example 4

(E/Z)—N-(2-(tert-butoxyimino)ethyl)-4-(5-(3,5-dichloro-4-fluorophenyl)-5-(trifluoromethyl)-4,5-dihydroisoxazol-3-yl)-1-naphthamide

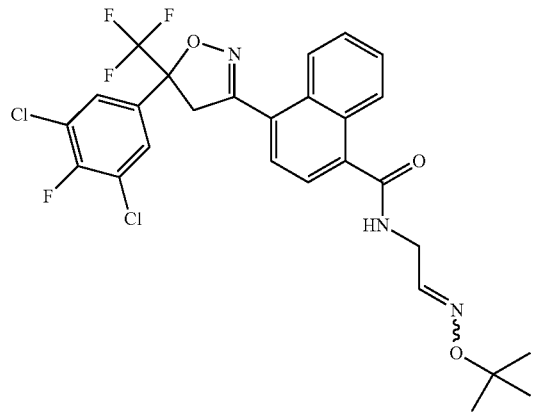 [SMILES: CC(C)(C)ON=CCNC(=O)c1ccc(C2=NOC(c3cc(Cl)c(F)c(Cl)c3)(C(F)(F)F)C2)c2ccccc12]

Example 4 was prepared using a procedure similar to that of Example 2 using t-butoxyamine.HCl in place of methoxyamine.HCl. ¹HNMR (CDCl₃) δ ppm: 8.84 (2H), 8.40-8.31 (2H), 7.71-7.53 (13H), 6.93 (1H), 6.56-6.46 (2H), 4.42-4.27 (6H), 3.92 (2H), 1.31-1.29 (18H); m/z (ESI) 584 ([M+H]⁺.

Example 5

(E/Z)-4-(5-(3,5-dichloro-4-fluorophenyl)-5-(trifluoromethyl)-4,5-dihydroisoxazol-3-yl)-N-(2-(hydroxyimino)ethyl)-1-naphthamide

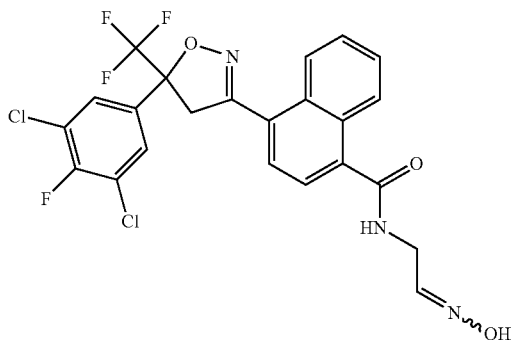 [SMILES: O=C(NCC=NO)c1ccc(C2=NOC(c3cc(Cl)c(F)c(Cl)c3)(C(F)(F)F)C2)c2ccccc12]

Example 5 was prepared using a procedure similar to that of Example 3 using hydroxylamine.HCl in place of methoxyamine.HCl. ¹HNMR (CDCl₃) δ ppm: 8.83 (2H), 8.35-8.29 (2H), 7.71-7.62 (11H), 7.52 (2H), 7.02 (1H), 6.55 (2H), 4.46-4.35 (4H), 4.28 (2H), 3.91 (2H); m/z (ESI) 528 [M+H]⁺.

Preparation 10: 4-(5-(3,5-dichloro-4-fluorophenyl)-5-(trifluoromethyl)-4,5-dihydroisoxazol-3-yl)-N-(3,3,3-trifluoro-2-hydroxypropyl)-1-naphthamide

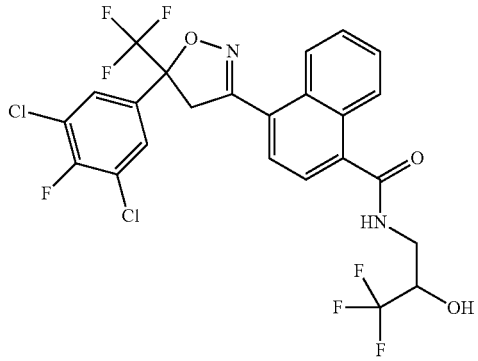 [SMILES: O=C(NCC(O)C(F)(F)F)c1ccc(C2=NOC(c3cc(Cl)c(F)c(Cl)c3)(C(F)(F)F)C2)c2ccccc12]

To a solution of 4-(5-(3,5-dichloro-4-fluorophenyl)-5-(trifluoromethyl)-4,5-dihydroisoxazol-3-yl)-1-naphthoic acid (Preparation 7, 1 g, 2.1 mmol) in DMF (25 mL) was added HATU (970 mg, 2.5 mmol) and triethylamine (1.0 mL, 7.0 mmol).

The reaction was stirred at room temperature for 15 minutes then treated with 3-amino-1,1,1-trifluoro-2-propanol (275 mg, 2.1 mmol). The reaction was stirred at room temperature for 18 hours. Next, the reaction was diluted with 0.1N NaOH and extracted with EtOAc (2×150 mL). The combined organic phase was dried (Na₂SO₄) and concentrated under vacuum. The crude material was chromatographed (80 g Redi-Sep column) eluting from 100% heptane to 40:60 EtOAc:heptane to afford the intermediate (1.06 g, 85%) as a solid. ¹HNMR (CDCl₃) δ ppm: 8.81 (1H), 8.28 (1H), 7.71-7.57 (5H), 7.49 (1H), 6.55 (1H) 4.32-4.25 (3H), 4.08-3.91 (1H), 3.85 (1H), 3.79-3.74 (1H); m/z (Cl) 583 [M+H]⁺.

Preparation 11: 4-(5-(3,5-dichloro-4-fluorophenyl)-5-(trifluoromethyl)-4,5-dihydroisoxazol-3-yl)-N-(3,3,3-trifluoro-2-oxopropyl)-1-naphthamide

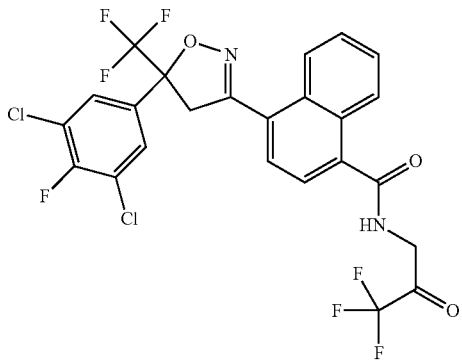 [SMILES: O=C(NCC(=O)C(F)(F)F)c1ccc(C2=NOC(c3cc(Cl)c(F)c(Cl)c3)(C(F)(F)F)C2)c2ccccc12]

Preparation 11 was prepared from the compound of Preparation 10 according to the method of Preparation 9. m/z (Cl) 581 ([M+H]⁺.

Example 6

(E)-4-(5-(3,5-dichloro-4-fluorophenyl)-5-(trifluoromethyl)-4,5-dihydroisoxazol-3-yl)-N-(3,3,3-trifluoro-2-(hydroxyimino)propyl)-1-naphthamide

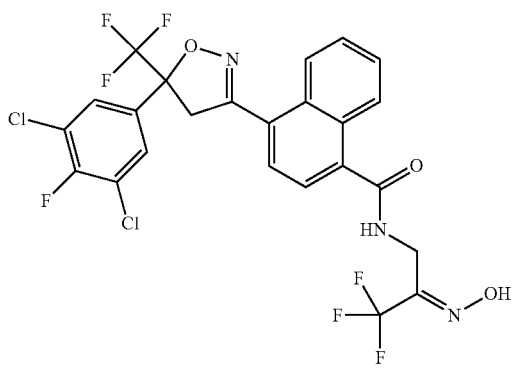 [SMILES: O=C(NC/C(=N\O)C(F)(F)F)c1ccc(C2=NOC(c3cc(Cl)c(F)c(Cl)c3)(C(F)(F)F)C2)c2ccccc12]

To a solution of 4-(5-(3,5-dichloro-4-fluorophenyl)-5-(trifluoromethyl)-4,5-dihydroisoxazol-3-yl)-N-(3,3,3-trifluoro-2-oxopropyl)-1-naphthamide (Preparation 11, 100 mg, 0.2 mmol) in EtOH (5 mL) was added hydroxylamine.HCl (30 mg, 0.4 mmol), water (1 mL), and KOAc (40 mg, 0.4 mmol). Reaction was heated to 130° C. for 40 minutes in a microwave. Water was added to the crude reaction and extracted with EtOAc (2×75 mL). The combined organics were dried (Na₂SO₄) and concentrated under vacuum. The crude material was chromatographed (24 g Redi-Sep column) eluting from 100% EtOAc to 50:50 EtOAc:heptane to afford (E)-4-(5-(3,5-dichloro-4-fluorophenyl)-5-(trifluoromethyl)-4,5-dihydroisoxazol-3-yl)-N-(3,3,3-trifluoro-2-(hydroxyimino)-propyl)-1-naphthamide (52 mg, 51%) as a solid. ¹HNMR (CDCl₃) δ ppm: 9.06 (1H), 8.81 (1H), 8.26 (1H), 7.71-7.57 (4H), 7.51 (1H), 6.48 (1H), 4.64 (2H) 4.28 (1H), 3.89 (1H); m/z (Cl) 596 [M+H]⁺.

Example 7

(E)-4-(5-(3,5-dichloro-4-fluorophenyl)-5-(trifluoromethyl)-4,5-dihydroisoxazol-3-yl)-N-(3,3,3-trifluoro-2-(methoxyimino)propyl)-1-naphthamide

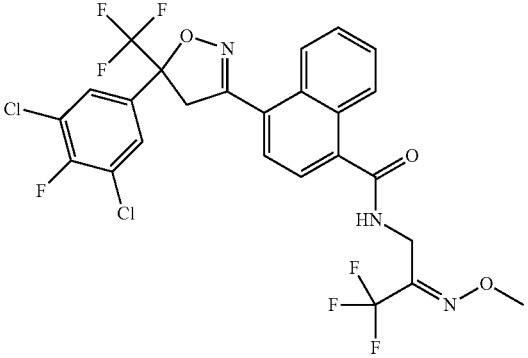 [SMILES: CO/N=C(\CNC(=O)c1ccc(C2=NOC(c3cc(Cl)c(F)c(Cl)c3)(C(F)(F)F)C2)c2ccccc12)C(F)(F)F]

Example 7 was prepared using a procedure similar to that of Example 6 using methoxyamine.HCl in place of hydroxylamine.HCl. The compound was purified by supercritical fluid chromatography (SFC) (Thar MS100, column: 2-ethyl pyridine 5 um 30×250 mm 5 μm, mobile phase: A is $CO_2$, B is MeOH, Gradient 10% B to 45 B % in 10 minutes, 100 bar backpressure, 100 mL/minute), retention time of 7.44 minutes. m/z (Cl) 610 [M+H]$^+$.

Example 8

(E)-4-(5-(3,5-dichloro-4-fluorophenyl)-5-(trifluoromethyl)-4,5-dihydroisoxazol-3-yl)-N-(2-(ethoxyimino)-3,3,3-trifluoropropyl)-1-naphthamide

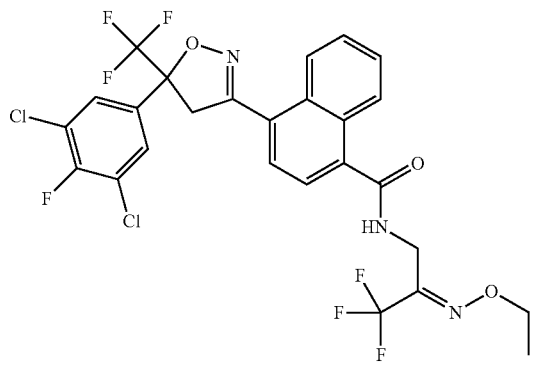 [SMILES: CCO/N=C(\CNC(=O)c1ccc(C2=NOC(c3cc(Cl)c(F)c(Cl)c3)(C(F)(F)F)C2)c2ccccc12)C(F)(F)F]

Example 8 was prepared using a procedure similar to that of Example 6 using ethoxyamine.HCl in place of hydroxylamine.HCl. Compound was purified according to method described in Example 7, retention time of 8.50 minutes. m/z (Cl) 624 [M+H]$^+$.

Example 9

(E)-4-(5-(3,5-dichloro-4-fluorophenyl)-5-(trifluoromethyl)-4,5-dihydroisoxazol-3-yl)-N-(3,3,3-trifluoro-2-(isopropoxyimino)propyl)-1-naphthamide

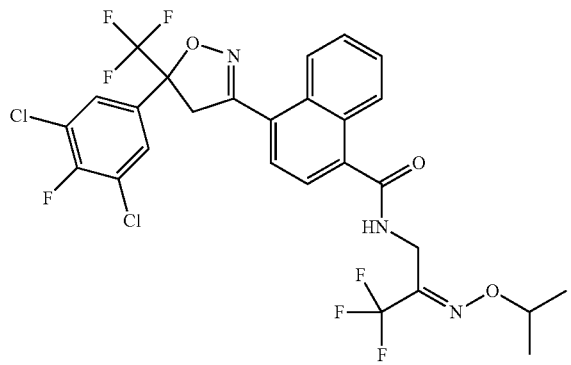 [SMILES: CC(C)O/N=C(\CNC(=O)c1ccc(C2=NOC(c3cc(Cl)c(F)c(Cl)c3)(C(F)(F)F)C2)c2ccccc12)C(F)(F)F]

Example 9 was prepared using a procedure similar to that of Example 6 using isopropylhydroxylamine.HCl in place of hydroxylamine.HCl. Compound was purified according to the method described in Example 7, retention time of 5.50 minutes. m/z (Cl) 638 [M+H]$^+$.

Preparation 12: methyl 4-(5-(3,5-dichlorophenyl)-5-(trifluoromethyl)-4,5-dihydroisoxazol-3-yl)-1-naphthoate

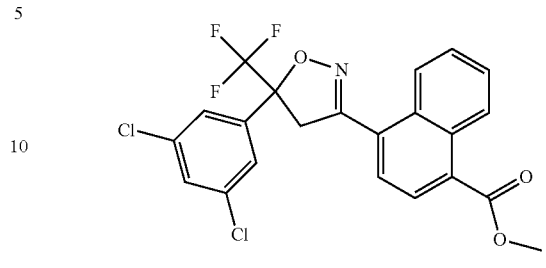

Prepared according to Preparation 6 substituting 1,3-dichloro-5-(1,1,1-trifluoroprop-2-en-2-yl)benzene for 1,3-dichloro-2-fluoro-5-(1,1,1-trifluoroprop-2-en-2-yl)benzene. $^1$H NMR (CDCl$_3$) δ ppm: 8.91 (1H), 8.81 (1H), 8.12 (1H), 7.72-7.68 (2H), 7.58 (3H), 7.48 (1H), 4.30 (1H), 4.05 (3H), 3.93 (1H).

Preparation 13: 4-(5-(3,5-dichlorophenyl)-5-(trifluoromethyl)-4,5-dihydroisoxazol-3-yl)-1-naphthoic acid

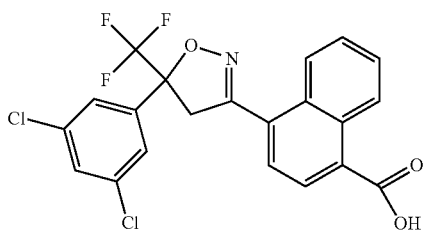 [SMILES: O=C(O)c1ccc(C2=NOC(c3cc(Cl)cc(Cl)c3)(C(F)(F)F)C2)c2ccccc12]

Prepared from the compound of Preparation 12, according to the method of Preparation 7. $^1$H NMR (DMSO-d$_6$) δ ppm: 8.83 (1H), 8.78 (1H), 8.13 (1H), 7.93 (1H), 7.83 (1H), 7.72-7.70 (4H), 4.55 (2H).

Preparation 14: 4-(5-(3,5-dichlorophenyl)-5-(trifluoromethyl)-4,5-dihydroisoxazol-3-yl)-N-(2-hydroxyethyl)-1-naphthamide

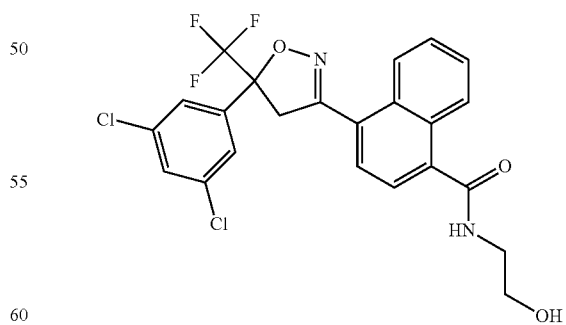

Preparation 14 was prepared from the compound of Preparation 13 according to the method of Preparation 8. $^1$H NMR (CDCl$_3$) δ ppm: 8.84 (1H), 8.32 (1H), 7.71-7.58 (5H), 7.51-7.48 (2H), 6.53 (1H) 4.28 (1H), 3.95-3.88 (3H), 3.75 (2H), 2.39 (1H); m/z (Cl) 497 [M+H]$^+$.

Preparation 15: 4-(5-(3,5-dichlorophenyl)-5-(trifluoromethyl)-4,5-dihydroisoxazol-3-yl)-N-(2-hydroxyethyl)-1-naphthamide

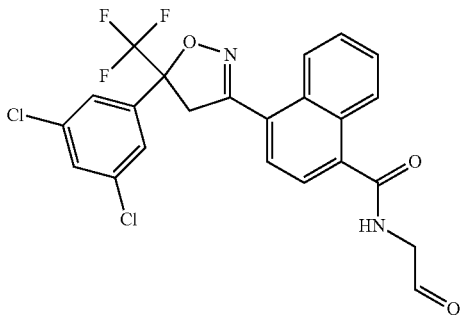 [SMILES: O=CCNC(=O)c1ccc(C2=NOC(c3cc(Cl)cc(Cl)c3)(C(F)(F)F)C2)c2ccccc12]

Preparation 15 was prepared from the compound of Preparation 14 according to the method of Preparation 9. m/z (CI) 495 [M+H]+.

Example 10

(E/Z)-4-(5-(3,5-dichlorophenyl)-5-(trifluoromethyl)-4,5-dihydroisoxazol-3-yl)-N-(2-(methoxyimino)ethyl)-1-naphthamide

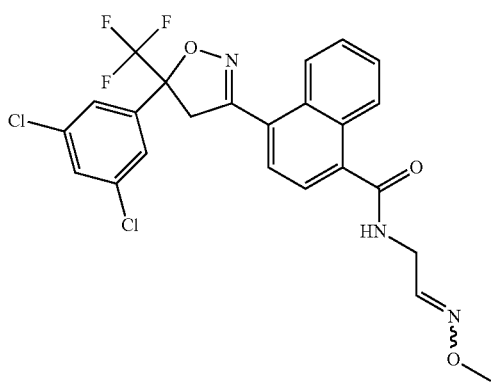 [SMILES: CON=CCNC(=O)c1ccc(C2=NOC(c3cc(Cl)cc(Cl)c3)(C(F)(F)F)C2)c2ccccc12]

Example 10 was prepared from compound of Preparation 15 according to the method of Example 3. $^1$HNMR (CDCl$_3$) δ ppm: 8.75 (2H), 8.28-8.19 (2H), 7.62-7.38 (15H), 6.84 (1H), 6.44 (1H), 6.35 (1H), 4.31-4.17 (6H), 3.86-3.78 (8H); m/z (CI) 524 [M+H]+.

Example 11

(E/Z)-4-(5-(3,5-dichlorophenyl)-5-(trifluoromethyl)-4,5-dihydroisoxazol-3-yl)-N-(2-(hydroxyimino)ethyl)-1-naphthamide

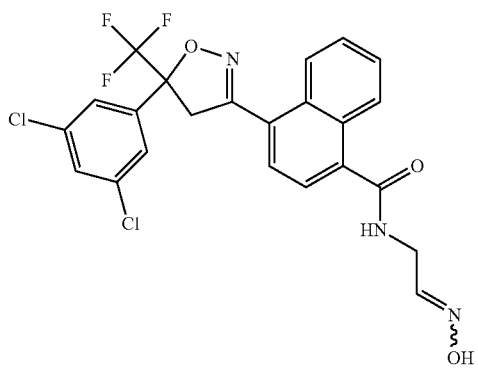 [SMILES: O=C(NCC=NO)c1ccc(C2=NOC(c3cc(Cl)cc(Cl)c3)(C(F)(F)F)C2)c2ccccc12]

Example 11 was prepared from compound of Preparation 15 according to the method of Example 3 using hydroxylamine.HCl in place of methoxyamine.HCl.
$^1$HNMR (CDCl$_3$) δ ppm: 8.84 (2H), 8.35-8.30 (2H), 7.71-7.58 (11H), 7.53-7.48 (4H), 7.04 (1H), 6.53 (2H), 4.47-4.36 (4H), 4.28 (2H), 3.91 (2H); m/z (ESI) 510 [M+H]+.

Preparation 16: 4-(5-(3,5-dichloro-4-fluorophenyl)-5-(trifluoromethyl)-4,5-dihydroisoxazol-3-yl)-N-(2-hydroxypropyl)-1-naphthamide

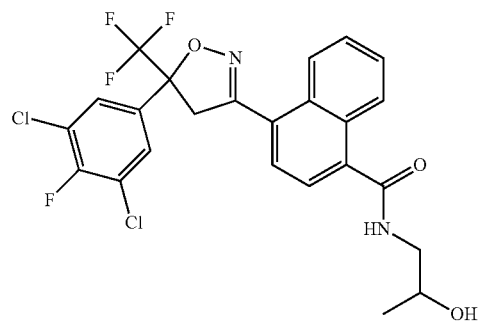 [SMILES: CC(O)CNC(=O)c1ccc(C2=NOC(c3cc(Cl)c(F)c(Cl)c3)(C(F)(F)F)C2)c2ccccc12]

Preparation 16 was prepared from the compound of Preparation 7 according to the method of Preparation 8 using 1-amino-2-propanol in place of 2-amino-ethanol. M/z (CI) 529 [M+H]+.

Preparation 17: 4-(5-(3,5-dichloro-4-fluorophenyl)-5-(trifluoromethyl)-4,5-dihydroisoxazol-3-yl)-N-(2-oxopropyl)-1-naphthamide

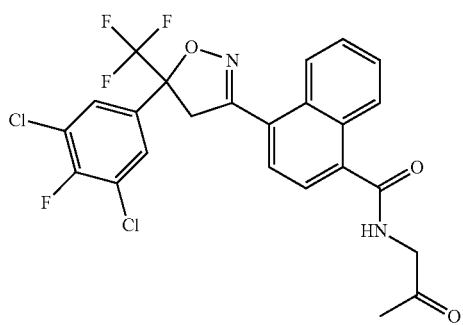 [SMILES: CC(=O)CNC(=O)c1ccc(C2=NOC(c3cc(Cl)c(F)c(Cl)c3)(C(F)(F)F)C2)c2ccccc12]

Preparation 17 was prepared from the compound of Preparation 16 according to the method of Preparation 9. $^1$HNMR (CDCl$_3$) δ ppm: 8.82 (1H), 8.35 (1H), 7.67-7.63 (5H), 7.51 (1H), 6.77 (1H), 4.46 (2H), 4.27 (1H), 3.90 (1H), 2.32 (3H).

Example 12

(Z)-4-(5-(3,5-dichloro-4-fluorophenyl)-5-(trifluoromethyl)-4,5-dihydroisoxazol-3-yl)-N-(2-(methoxyimino)propyl)-1-naphthamide

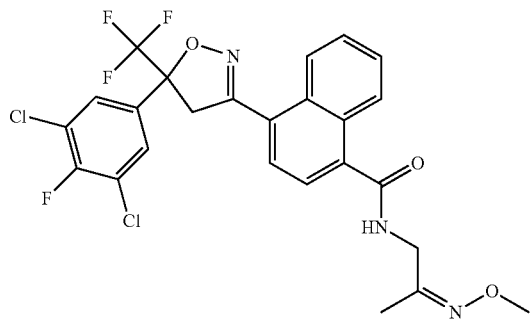 [SMILES: CO/N=C(/C)CNC(=O)c1ccc(C2=NOC(c3cc(Cl)c(F)c(Cl)c3)(C(F)(F)F)C2)c2ccccc12]

Example 12 was prepared from compound of Preparation 17 according to the method of Example 3. $^1$HNMR (CDCl$_3$) δ ppm: 8.83 (1H), 8.38 (1H), 7.70-7.63 (5H), 7.53 (1H), 6.73 (1H), 4.30-4.28 (3H), 3.88-3.85 (4H), 1.96 (3H); m/z (Cl) 556 [M+H]$^+$.

Preparation 18: methyl 4-(5-(3,4,5-trichlorophenyl)-5-(trifluoromethyl)-4,5-dihydroisoxazol-3-yl)-1-naphthoate

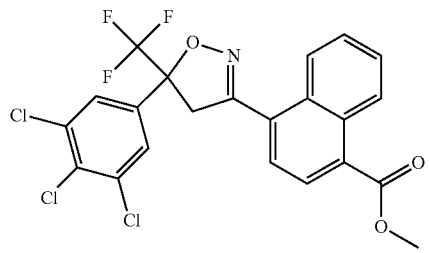 [SMILES: COC(=O)c1ccc(C2=NOC(c3cc(Cl)c(Cl)c(Cl)c3)(C(F)(F)F)C2)c2ccccc12]

Prepared according to Preparation 6 substituting 1,2,3-trichloro-5-(1,1,1-trifluoroprop-2-en-2-yl)benzene for 1,3-dichloro-2-fluoro-5-(1,1,1-trifluoroprop-2-en-2-yl)benzene. $^1$H NMR (CDCl$_3$) δ ppm: 8.91 (1H), 8.80 (1H), 8.12 (1H), 7.73-7.69 (4H), 7.55 (1H), 4.30 (1H), 4.05 (3H), 3.92 (1H).

Preparation 19: 4-(5-(3,4,5-trichlorophenyl)-5-(trifluoromethyl)-4,5-dihydroisoxazol-3-yl)-1-naphthoic acid

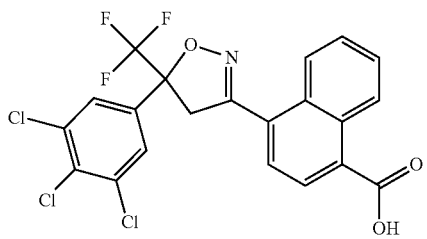 [SMILES: O=C(O)c1ccc(C2=NOC(c3cc(Cl)c(Cl)c(Cl)c3)(C(F)(F)F)C2)c2ccccc12]

Prepared from the compound of Preparation 18 according to the method of Preparation 7. $^1$H NMR (DMSO-d$_6$) δ ppm: 8.83 (1H), 8.77 (1H), 8.13 (1H), 7.93-7.91 (3H), 7.75-7.72 (2H), 4.57 (2H).

Preparation 20: 4 N-(2-hydroxyethyl)-4-(5-(3,4,5-trichlorophenyl)-5-(trifluoromethyl)-4,5-dihydroisoxazol-3-yl)-1-naphthamide

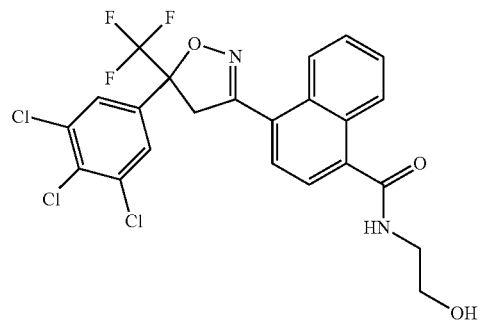 [SMILES: O=C(NCCO)c1ccc(C2=NOC(c3cc(Cl)c(Cl)c(Cl)c3)(C(F)(F)F)C2)c2ccccc12]

Preparation 20 was prepared from the compound of Preparation 19 according to the method of Preparation 8. m/z (Cl) 531 [M+H]$^+$.

Preparation 21: N-(2-oxoethyl)-4-(5-(3,4,5-trichlorophenyl)-5-(trifluoromethyl)-4,5-dihydroisoxazol-3-yl)-1-naphthamide

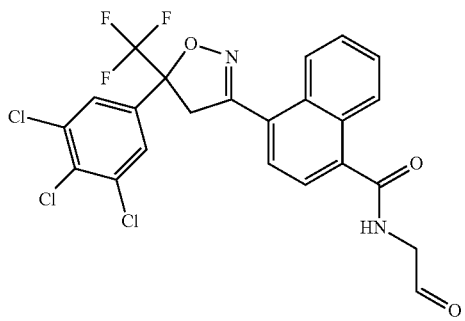 [SMILES: O=CCNC(=O)c1ccc(C2=NOC(c3cc(Cl)c(Cl)c(Cl)c3)(C(F)(F)F)C2)c2ccccc12]

Preparation 21 was prepared from the compound of Preparation 20 according to the method of Preparation 9. m/z (Cl) 529 [M+H]$^+$.

Example 13

(E/Z)—N-(2-(ethoxyimino)ethyl)-4-(5-(3,4,5-trichlorophenyl)-5-(trifluoromethyl)-4,5-dihydroisoxazol-3-yl)-1-naphthamide

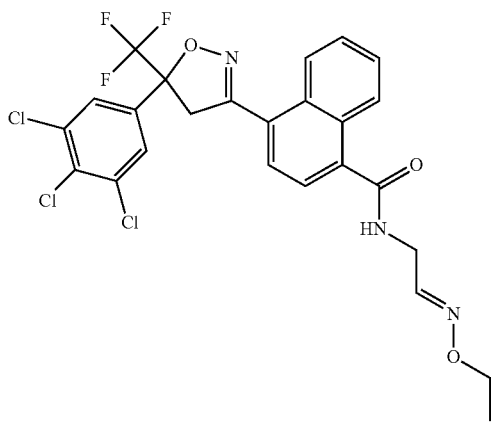 [SMILES: CCO/N=C/CNC(=O)c1ccc(C2=NOC(c3cc(Cl)c(Cl)c(Cl)c3)(C(F)(F)F)C2)c2ccccc12]

Example 13 was prepared from compound of Preparation 21 according to the method of Example 3 using ethoxyamine hydrochloride in place of methoxyamine hydrochloride. $^1$HNMR (CDCl$_3$) δ ppm: 8.81 (2H), 8.36-8.27 (2H), 7.70-7.48 (13H), 6.92 (1H), 6.56-6.48 (2H), 4.40-4.25 (6H), 4.21-4.08 (4H), 3.90 (2H) (1.30-1.24) (6H); m/z (Cl) 572 [M+H]$^+$.

Example 14

(E/Z)—N-(2-(2-fluoroethoxyimino)ethyl)-4-(5-(3,4,5-trichlorophenyl)-5-(trifluoromethyl)-4,5-dihydroisoxazol-3-yl)-1-naphthamide

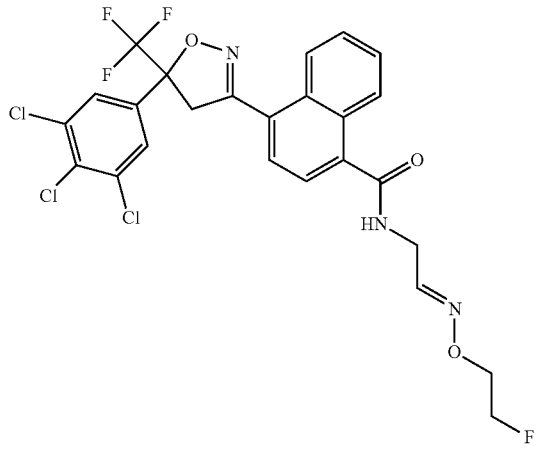 [SMILES: O=C(NC/C=N/OCCF)c1ccc(C2=NOC(c3cc(Cl)c(Cl)c(Cl)c3)(C(F)(F)F)C2)c2ccccc12]

Example 14 was prepared from compound of Preparation 21 according to the method of Example 3 substituting O-(2-fluoroethyl)hydroxylamine hydrochloride for methoxyamine hydrochloride. $^1$HNMR (CDCl$_3$) δ ppm: 8.81 (2H), 8.33-8.27 (2H), 7.71-7.47 (13H), 7.00 (1H), 6.58-6.49 (2H), 4.72-4.56 (4H), 4.43-4.25 (10H), 3.90 (2H); m/z (Cl) 590 [M+H]$^+$.

Example 15

(E/Z)—N-(2-(methoxyimino)ethyl)-4-(5-(3,4,5-trichlorophenyl)-5-(trifluoromethyl)-4,5-dihydroisoxazol-3-yl)-1-naphthamide

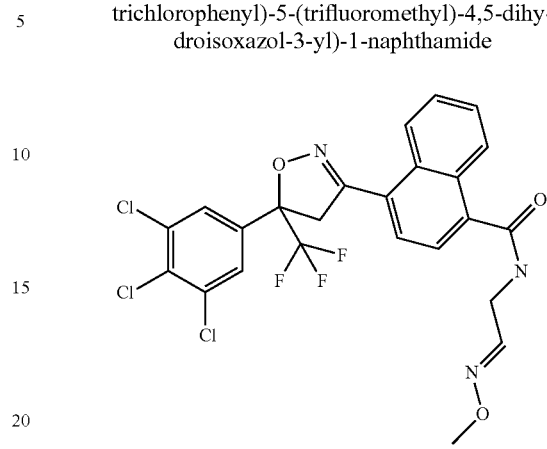

To a stirred suspension of 4-[5-(3,4,5-Trichloro-phenyl)-5-trifluoromethyl-4,5-dihydro-isoxazol-3-yl]-naphthalene-1-carboxylic acid(2-oxo-ethyl)-amide (0.09 g, 0.170 mmol, 1 eq) in mixture of MeOH (4 mL) and water (4 mL) was added methoxyamine hydrochloride (0.034 g, 0.409 mmol, 2.4 eq.) at room temperature. Resulting reaction mixture was heated at 80° C. for 2 hours. Progress of reaction was monitored by TLC using 5% MeOH in DCM. R$_f$ of new spot and starting material was 0.25 and 0.5 respectively. After consumption of starting material, MeOH from the reaction mixture was evaporated in vacuo. MeOH (5 mL) was added to the reaction mixture and evaporated off to eliminate water. A pale yellow semisolid (0.1 g, crude) was isolated. Crude compound was purified by column chromatography using 100-200 mesh silica gel. Desired product gets eluted in 0.5% MeOH in DCM and washed with pentane (2×5 mL) to afford off white thick mass (0.045 g, 48%) $^1$H NMR (400 MHz, CDCl$_3$) δ: (Mixture of E and Z isomer) 3.84 (s, 2H), 3.86-3.92 (m, 1H), 3.92 (s, 1H), 4.24-4.28 (m, 1H), 4.31-4.36 (m, 2H), 6.35-6.49 (m, 1H), 7.50-7.68 (m, 6H), 8.26-8.35 (m, 1H), 8.80-8.82 (m, 1H); m/z=555.90 (M−H).

Preparation 22: 4-[5-(3,4-Dichloro-5-trifluoromethyl-phenyl)-5-trifluoromethyl-4,5-dihydro-isoxazol-3-yl]-naphthalene-1-carboxylic acid methyl ester

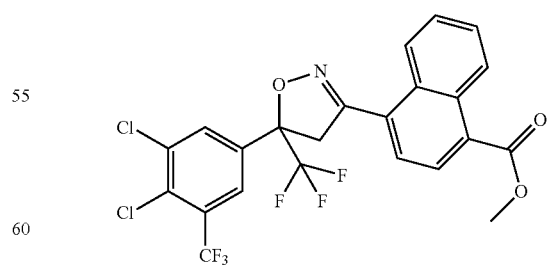

Prepared according to Preparation 6 substituting 1,2-dichloro-3-(trifluoromethyl)-5-(3,3,3-trifluoroprop-1-en-2-yl)benzene for 1,3-dichloro-2-fluoro-5-(3,3,3-trifluoroprop-1-en-2-yl)benzene. Yield=53.26%; $^1$H NMR (400 MHz, CDCl₃) δ: 3.90 (d, J=17.3 Hz, 1H), 4.02 (s, 3H), 4.32 (d, J=17.24 Hz, 1H), 7.54 (d, J=7.64 Hz, 1H), 7.64-7.70 (m, 2H), 7.87 (d, J=1.44 Hz, 1H), 7.99 (d, J=1.84 Hz, 1H), 8.09 (d, J=7.68 Hz, 1H), 8.77-8.79 (m, 1H), 8.86-8.88 (m, 1H); m/z=534.10 (M−H).

Preparation 23: 4-[5-(3,4-Dichloro-5-trifluoromethyl-phenyl)-5-trifluoromethyl-4,5-dihydro-isoxazol-3-yl]-naphthalene-1-carboxylic acid

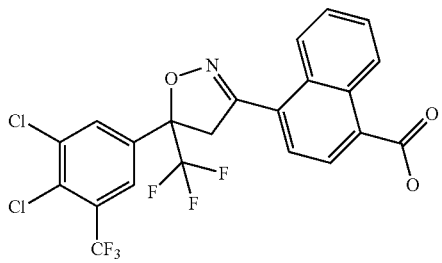 [SMILES: O=C(O)c1ccc(C2=NOC(c3cc(Cl)c(Cl)c(C(F)(F)F)c3)(C(F)(F)F)C2)c2ccccc12]

Prepared from the compound of Preparation 22 according to the method of Preparation 7. Yield=90.33%; ¹H NMR (400 MHz, CDCl3) δ: 3.90 (d, J=17.36 Hz, 1H), 4.31 (d, J=17.32 Hz, 1H), 7.54 (d, J=7.64 Hz, 1H), 7.66-7.68 (m, 2H), 7.87 (s, 1H), 7.98 (s, 1H), 8.24 (d, J=7.12 Hz, 1H), 8.76-8.78 (m, 1H), 8.99-9.01 (m, 1H); m/z=520.10 (M−H).

Preparation 24: 4-[5-(3,4-Dichloro-5-trifluoromethyl-phenyl)-5-trifluoromethyl-4,5-dihydro-isoxazol-3-yl]-naphthalene-1-carboxylic acid (2-hydroxy-ethyl)-amide

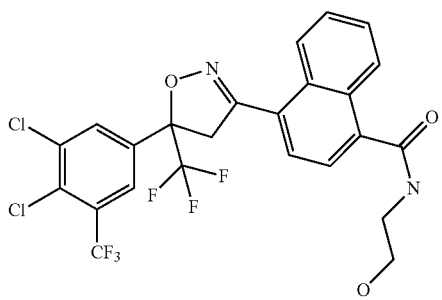 [SMILES: O=C(NCCO)c1ccc(C2=NOC(c3cc(Cl)c(Cl)c(C(F)(F)F)c3)(C(F)(F)F)C2)c2ccccc12]

Prepared from the compound of Preparation 23 according to the method of Preparation 8. Yield 93.61%. ¹H NMR (400 MHz, CDCl₃) δ: 2.21 (t, J=4.96 Hz, 1H), 3.71-3.75 (m, 2H), 3.87-3.93 (m, 3H), 4.31 (d, J=17.2 Hz, 1H), 6.44 (t, J=5.04 Hz, 1H), 7.50 (d, J=7.4 Hz, 1H), 7.59-7.69 (m, 3H), 7.87 (d, J=1.6 Hz, 1H), 7.98 (d, J=1.76 Hz, 1H), 8.31 (dd, J₁=2.2 Hz, J₂=7.76 Hz, 1H), 8.81 (dd, J₁=1.84 Hz, J₂=7.84 Hz, 1H); m/z=562.90 (M−H).

Preparation 25: 4-[5-(3,4-Dichloro-5-trifluoromethyl-phenyl)-5-trifluoromethyl-4,5-dihydro-isoxazol-3-yl]-naphthalene-1-carboxylic acid (2-oxoethyl)-amide

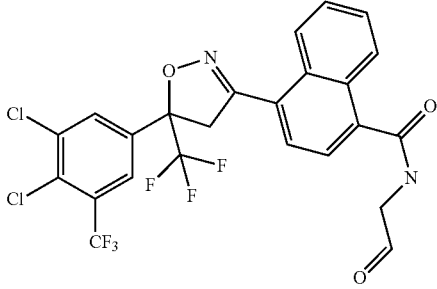 [SMILES: O=CCNC(=O)c1ccc(C2=NOC(c3cc(Cl)c(Cl)c(C(F)(F)F)c3)(C(F)(F)F)C2)c2ccccc12]

Prepared from the compound of Preparation 24 according to the method of Preparation 9. Yield 18.26%. ¹H NMR (400 MHz, DMSO-d6) δ: 4.18-4.21 (m, 3H), 4.61 (d, J=5.64 Hz, 1H), 7.61-7.74 (m, 2H), 7.76-7.80 (m, 1H), 7.90-7.92 (m, 1H), 7.98-8.05 (m, 3H), 8.27 (bs, 1H), 8.78 (t, J=5.44 Hz, 1H), 9.66 (s, 1H); m/z=560.60 (M−H).

Example 16

(E/Z)-4-(5-(3,4-dichloro-5-(trifluoromethyl)phenyl)-5-(trifluoromethyl)-4,5-dihydroisoxazol-3-yl)-N-(2-(methoxyimino)ethyl)-1-naphthamide Example 16 was prepared from the compound of Preparation 25 according to the method of Example 3. Yield 62.79%. ¹H NMR (400 MHz, CDCl3) δ: (Mixture of E and Z isomer) 3.84 (s, 2H), 3.88 (s, 1H), 3.92 (s, 1H), 4.29-4.36 (m, 3H), 6.37-6.48 (m, 1H), 7.52-7.69 (m, 5H), 7.87 (s, 1H), 7.98 (s, 1H), 8.26-8.35 (m, 1H), 8.81-8.83 (m, 1H); m/z=589.80 (M−H), Preparation 26: 4-[5-(3,5-Bis-trifluoromethyl-phenyl)-5-trifluoromethyl-4,5-dihydro-isoxazol-3-yl]-naphthalene-1-carboxylic acid methyl ester

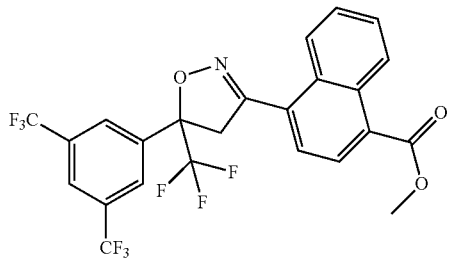 [SMILES: COC(=O)c1ccc(C2=NOC(c3cc(C(F)(F)F)cc(C(F)(F)F)c3)(C(F)(F)F)C2)c2ccccc12]

Prepared according to Preparation 6 substituting 1,3-bis(trifluoromethyl)-5-(3,3,3-trifluoroprop-1-en-2-yl)benzene for 1,3-dichloro-2-fluoro-5-(3,3,3-trifluoroprop-1-en-2-yl)benzene. Yield=51.28%. $^1$H NMR (400 MHz, CDCl3) δ: 3.95 (d, J=17.24 Hz, 1H), 4.02 (s, 3H), 4.38 (d, J=17.36 Hz, 1H), 7.55 (d, J=7.6 Hz, 1H), 7.66-7.69 (m, 2H), 7.98 (s, 1H), 8.09 (d, J=7.68 Hz, 1H), 8.12 (s, 2H), 8.78-8.81 (m, 1H), 8.86-8.88 (m, 1H); m/z=533.80 (M−H)

Preparation 27: 4-[5-(3,5-Bis-trifluoromethyl-phenyl)-5-trifluoromethyl-4,5-dihydro-isoxazol-3-yl]naphthalene-1-carboxylic acid

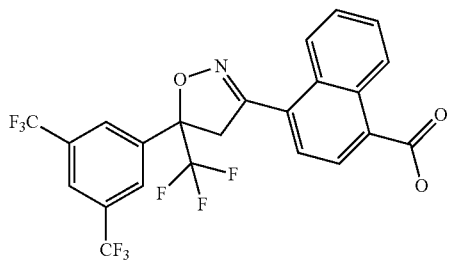 [SMILES: O=C(O)c1ccc(C2=NOC(c3cc(C(F)(F)F)cc(C(F)(F)F)c3)(C(F)(F)F)C2)c2ccccc12]

Prepared from the compound of Preparation 26 according to the method of Preparation 7. Yield=94.22%. $^1$H NMR (400 MHz, CDCl3) δ: 3.96 (d, J=17.36 Hz, 1H), 4.40 (d, J=17.32 Hz, 1H), 7.60 (d, J=7.6 Hz, 1H), 7.68-7.75 (m, 2H), 7.99 (s, 1H), 8.12 (s, 2H), 8.31 (d, J=7.68 Hz, 1H), 8.80-8.82 (m, 1H), 9.05-9.07 (m, 1H); m/z=519.80 (M−H).

Preparation 28: 4-[5-(3,5-Bis-trifluoromethyl-phenyl)-5-trifluoromethyl-4,5-dihydro-isoxazol-3-yl]-naphthalene-1-carboxylic acid (2-hydroxy-ethyl)-amide

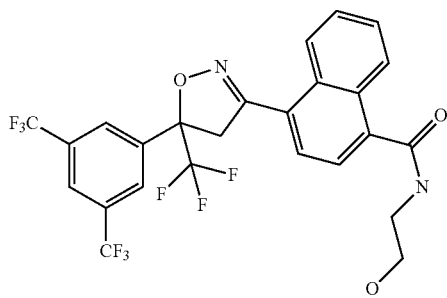 [SMILES: O=C(NCCO)c1ccc(C2=NOC(c3cc(C(F)(F)F)cc(C(F)(F)F)c3)(C(F)(F)F)C2)c2ccccc12]

Prepared from the compound of Preparation 27 according to the method of Preparation 8. Yield 86.13%. $^1$H NMR (400 MHz, CDCl$_3$) δ: 1.24 (t, J=7.14 Hz, 1H), 3.72-3.75 (m, 2H), 3.92-3.96 (m, 3H), 4.38 (d, J=17.28 Hz, 1H), 7.53 (d, J=7.44 Hz, 1H), 7.60-7.68 (m, 3H), 7.98 (s, 1H), 8.12 (s, 2H), 8.31 (dd, J$_1$=1.52 Hz, J$_2$=7.8 Hz, 1H), 8.80-8.82 (dd, J$_1$=1.52 Hz, J$_2$=9.28 Hz, 1H); m/z=565.10 (M+H).

Preparation 29: 4-[5-(3,5-Bis-trifluoromethyl-phenyl)-5-trifluoromethyl-4,5-dihydro-isoxazol-3-yl]-naphthalene-1-carboxylic acid (2-oxo-ethyl)-amide

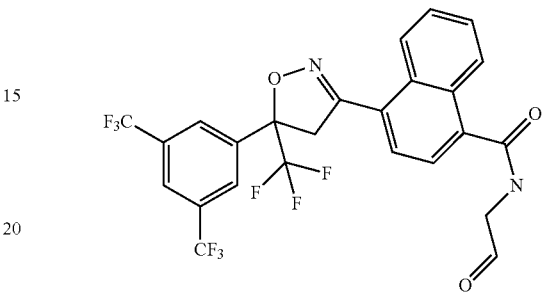

Prepared from the compound of Preparation 28 according to the method of Preparation 9. $^1$H NMR (400 MHz, CDCl$_3$) δ: 3.95 (d, J=17.2 Hz, 1H), 4.24 (s, 1H), 4.35-4.40 (m, 1H), 4.54 (d, J=4.92 Hz, 1H), 7.50-7.52 (m, 1H), 7.59-7.70 (m, 3H), 7.98 (s, 1H), 8.12 (bs, 2H), 8.33-8.35 (m, 1H), 8.83-8.85 (m, 1H), 9.81 (s, 1H); m/z=560.70 (M−H).

Example 17

(E/Z)-4-(5-(3,5-bis(trifluoromethyl)phenyl)-5-(trifluoromethyl)-4,5-dihydroisoxazol-3-yl)-N-(2-(methoxyimino)ethyl)-1-naphthamide

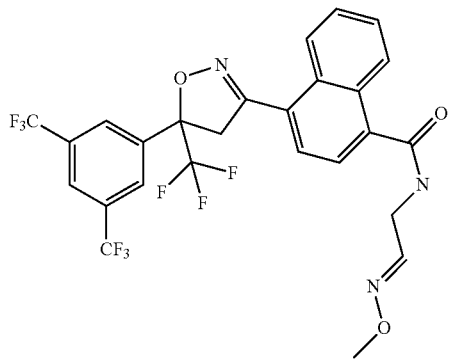 [SMILES: CO/N=C/CNC(=O)c1ccc(C2=NOC(c3cc(C(F)(F)F)cc(C(F)(F)F)c3)(C(F)(F)F)C2)c2ccccc12]

Example 17 was prepared from the compound of Preparation 29 according to the method of Example 3. Yield 31.85%. $^1$H NMR (400 MHz, CDCl$_3$) δ: (Mixture of E and Z isomer) 3.84 (s, 2H), 3.92-3.97 (m, 2H), 4.31-4.40 (m, 3H), 6.37-6.50 (m, 1H), 6.37-6.50 (m, 1H), 7.56-7.70 (m, 4H), 7.98 (s, 1H), 8.12 (s, 2H), 8.26-8.35 (m, 1H), 8.83-8.85 (m, 1H); m/z=589.80 (M−H), Preparation 30: 4-[5-(3,4-Difluoro-5-trifluoromethyl-phenyl)-5-trifluoromethyl-4,5-dihydro-isoxazol-3-yl]-naphthalene-1-carboxylic acid methyl ester

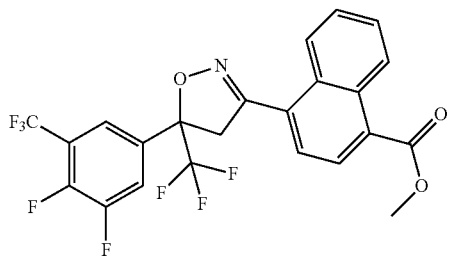 [SMILES: COC(=O)c1ccc(C2=NOC(c3cc(F)c(F)c(C(F)(F)F)c3)(C(F)(F)F)C2)c2ccccc12]

Prepared according to Preparation 6 substituting 1,2-difluoro-3-(trifluoromethyl)-5-(3,3,3-trifluoroprop-1-en-2-yl)benzene for 1,3-dichloro-2-fluoro-5-(3,3,3-trifluoroprop-1-en-2-yl)benzene. Yield=54.69%. $^1$H NMR (400 MHz, CDCl3) δ: 3.90 (d, J=17.28 Hz, 1H), 4.02 (s, 3H), 4.32 (d, J=17.32 Hz, 1H), 7.53 (d, J=7.56 Hz, 1H), 7.65-7.76 (m, 4H), 8.09 (d, J=7.68 Hz, 1H), 8.76-8.78 (m, 1H), 8.86-8.87 (m, 1H); m/z=502.10 (M−H).

Preparation 31: 4-[5-(3,4-Difluoro-5-trifluoromethyl-phenyl)-5-trifluoromethyl-4,5-dihydro-isoxazol-3-yl]naphthalene-1-carboxylic acid

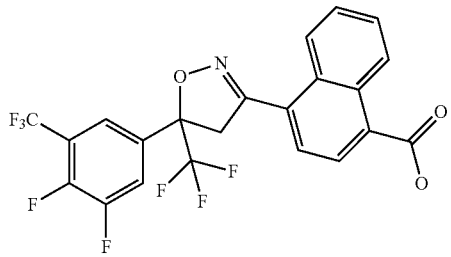 [SMILES: O=C(O)c1ccc(C2=NOC(c3cc(F)c(F)c(C(F)(F)F)c3)(C(F)(F)F)C2)c2ccccc12]

Prepared from the compound of Preparation 30 according to the method of Preparation 7. Yield=90.13%. $^1$H NMR (400 MHz, CDCl3) δ: 3.92 (d, J=17.04 Hz, 1H), 4.40 (d, J=17.2 Hz, 1H), 7.59-7.74 (m, 5H), 8.30 (d, J=7.72 Hz, 1H), 8.78-8.81 (m, 1H), 9.05-9.07 (m, 1H); m/z=488.10 (M−H).

Preparation 32: 4-[5-(3,4-Difluoro-5-trifluoromethyl-phenyl)-5-trifluoromethyl-4,5-dihydro-isoxazol-3-yl]-naphthalene-1-carboxylic acid (2-hydroxy-ethyl)-amide

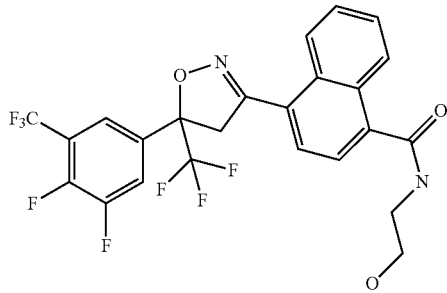 [SMILES: O=C(NCCO)c1ccc(C2=NOC(c3cc(F)c(F)c(C(F)(F)F)c3)(C(F)(F)F)C2)c2ccccc12]

Prepared from the compound of Preparation 31 according to the method of Preparation 8. Yield 73.56%. $^1$H NMR (400 MHz, CDCl$_3$) δ: 2.27 (t, J=4 Hz, 1H), 3.72 (q, J=5.1 Hz, 2H), 3.86-3.92 (m, 3H), 4.30 (d, J=17.16 Hz, 1H), 6.45-6.46 (m, 1H), 7.48 (d, J=7.44 Hz, 1H), 7.57 (d, J=7.36 Hz, 1H), 7.61-7.67 (m, 3H), 7.73-7.77 (m, 1H), 8.29 (dd, J$_1$=1.76 Hz, J$_2$=7.52 Hz, 1H), 8.81 (dd, J$_1$=1.6 Hz, J$_2$=7.72 Hz, 1H); m/z=530.90 (M−H).

Preparation 33: 4-[5-(3,4-Difluoro-5-trifluoromethyl-phenyl)-5-trifluoromethyl-4,5-dihydro-isoxazol-3-yl]naphthalene-1-carboxylic acid (2-oxo-ethyl)-amide

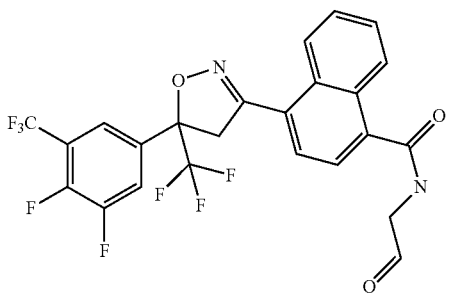 [SMILES: O=CCNC(=O)c1ccc(C2=NOC(c3cc(F)c(F)c(C(F)(F)F)c3)(C(F)(F)F)C2)c2ccccc12]

Prepared from the compound of Preparation 32 according to the method of Preparation 9. m/z=531.00 (M+H).

Example 18

(E/Z)-4-(5-(3,4-difluoro-5-(trifluoromethyl)phenyl)-5-(trifluoromethyl)-4,5-dihydroisoxazol-3-yl)-N-(2-(methoxyimino)ethyl)-1-naphthamide

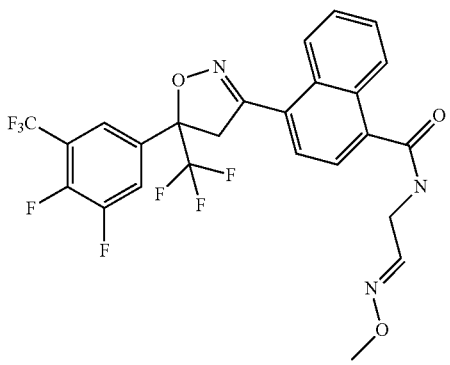 [SMILES: CO/N=C/CNC(=O)c1ccc(C2=NOC(c3cc(F)c(F)c(C(F)(F)F)c3)(C(F)(F)F)C2)c2ccccc12]

Example 18 was prepared from the compound of Preparation 33 by the method of Example 3. Yield 19.00%. $^1$H NMR (400 MHz, CDCl$_3$) δ: (Mixture of E and Z isomer) 3.84 (s, 2H), 3.86-3.87 (m, 1H), 3.92 (s, 1H), 4.28-4.38 (m, 3H), 6.36-6.48 (m, 1H), 7.50-7.60 (m, 2H), 7.64-7.77 (m, 4H), 7.74-7.77 (m, 1H), 8.26-8.35 (m, 1H), 8.81-8.83 (m, 1H); m/z=558.10 (M−H), HPLC purity-97.41%

Preparation 34: 4-[5-(3-Chloro-5-fluoro-phenyl)-5-trifluoromethyl-4,5-dihydro-isoxazol-3-yl]-naphthalene-1-carboxylic acid methyl ester

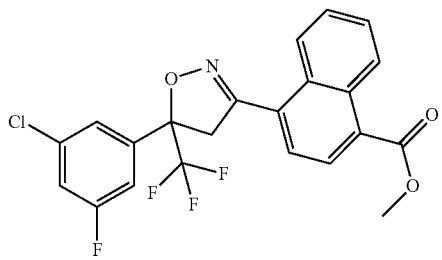 [SMILES: COC(=O)c1ccc(C2=NOC(c3cc(F)cc(Cl)c3)(C(F)(F)F)C2)c2ccccc12]

Prepared according to Preparation 6 substituting 1-chloro-3-fluoro-5-(3,3,3-trifluoroprop-1-en-2-yl)benzene for 1,3-dichloro-2-fluoro-5-(3,3,3-trifluoroprop-1-en-2-yl)benzene. Yield=58.97%. $^1$H NMR (400 MHz, CDCl3) δ: 3.89 (d, J=17.16 Hz, 1H), 4.02 (s, 3H), 4.26 (d, J=17.2 Hz, 1H), 7.17-7.19 (m, 1H), 7.31 (d, J=9.08 Hz, 1H), 7.44 (s, 1H), 8.52 (d, J=7.72 Hz, 1H), 7-63-7.69 (m, 2H), 8.08 (d, J=7.68 Hz, 1H), 8.76-8.79 (m, 1H), 8.85-8.87 (m, 1H); m/z=449.70 (M−H)

Preparation 35: 4-[5-(3-Chloro-5-fluoro-phenyl)-5-trifluoromethyl-4,5-dihydro-isoxazol-3-yl]-naphthalene-1-carboxylic acid

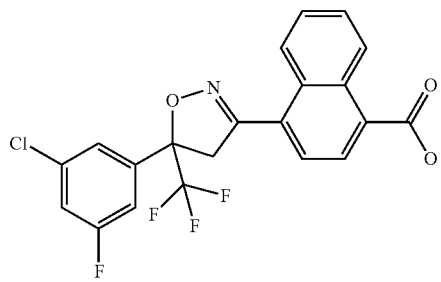 [SMILES: O=C(O)c1ccc(C2=NOC(c3cc(F)cc(Cl)c3)(C(F)(F)F)C2)c2ccccc12]

Prepared from the compound of Preparation 34 according to the method of Preparation 7. Yield=58.43%. $^1$H NMR (400 MHz, CDCl3) δ: 3.91 (d, J=17.32 Hz, 1H), 4.28 (d, J=17.32 Hz, 1H), 7.17-7.20 (m, 1H), 7.31 (d, J=9 Hz, 1H), 7.45 (s, 1H), 7.57 (d, J=7.68 Hz, 1H), 7.67-7.74 (m, 2H), 8.31 (d, J=7.68 Hz, 1H), 8.89 (dd, $J_1$=7.68 Hz, $J_2$=1.8 Hz, 1H), 9.06 (dd, $J_1$=7.72 Hz, $J_2$=1.8 Hz, 1H), m/z=435.70 (M−H).

Preparation 36: 4-[5-(3-Chloro-5-fluoro-phenyl)-5-trifluoromethyl-4,5-dihydro-isoxazol-3-yl]-naphthalene-1-carboxylic acid (2-hydroxy-ethyl)-amide

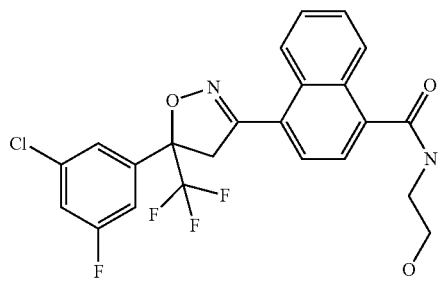 [SMILES: O=C(NCCO)c1ccc(C2=NOC(c3cc(F)cc(Cl)c3)(C(F)(F)F)C2)c2ccccc12]

Prepared from the compound of Preparation 35, according to the method of Preparation 8. Yield 84.21%. $^1$H NMR (400 MHz, CDCl$_3$) δ: 2.28 (s, 1H), 3.71 (q, J=5.16 Hz, 2H), 3.86-3.92 (m, 3H), 4.38 (d, J=17.2 Hz, 1H), 6.45 (t, J=5.26 Hz, 1H), 7.17-7.19 (m, 1H), 7.31 (d, J=9.08 Hz, 1H), 7.44 (s, 1H), 7.48 (d, J=7.4 Hz 1H), 7.58 (d, J=7.4 Hz 1H), 7.60-7.67 (m, 2H), 8.31 (dd, $J_1$=2.16 Hz, $J_2$=5.56 Hz, 1H), 8.81 (dd, $J_1$=1.68 Hz, $J_2$=5.88 Hz, 1H); m/z=478.70 (M−H).

Preparation 37: 4-[5-(3-Chloro-5-fluoro-phenyl)-5-trifluoromethyl-4,5-dihydro-isoxazol-3-yl]-naphthalene-1-carboxylic acid (2-oxo-ethyl)-amide

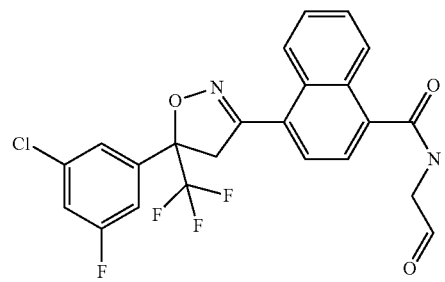 [SMILES: O=CCNC(=O)c1ccc(C2=NOC(c3cc(F)cc(Cl)c3)(C(F)(F)F)C2)c2ccccc12]

Prepared from the compound of Preparation 35 according to the method of Preparation 9. m/z=476.60 (M−H).

Example 19

(E/Z)-4-(5-(3-chloro-5-fluorophenyl)-5-(trifluoromethyl)-4,5-dihydroisoxazol-3-yl)-N-(2-(methoxyimino)ethyl)-1-naphthamide

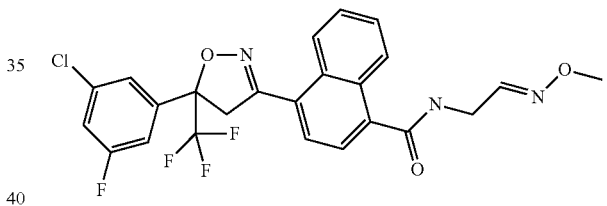

Prepared from the compound of Preparation 37, according to the method of Example 3. Yield 24.03%. $^1$H NMR (400 MHz, CDCl$_3$) δ: (Mixture of E and Z isomer) 3.84 (s, 2H), 3.86-3.87 (m, 1H), 3.91-3.92 (m, 1H), 4.23-4.35 (m, 3H), 6.39-6.50 (m, 1H), 7.17-7.24 (m, 1H), 7.31 (d, J=9.08 Hz, 1H), 7.49 (s, 1H), 7.50-7.68 (m, 5H), 8.25-8.34 (m, 1H), 8.83 (d, J=1.48 Hz, 1H); m/z): =506.10 (M−H), Preparation 38: 4-(5-(3,5-dichloro-4-fluorophenyl)-5-(trifluoromethyl)-4,5-dihydroisoxazol-3-yl)-N-(2-bis(methoxy)ethyl)-1-naphthamide

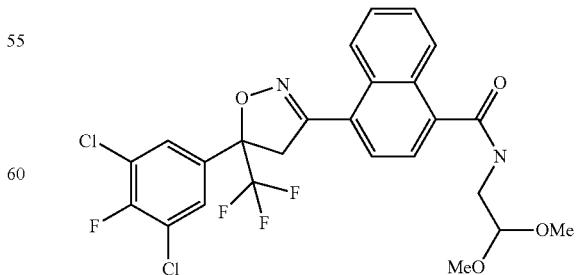

To a slurry of amino acetaldehyde dimethyl acetal (8.71 gm, 83 mmol) in methylene chloride (150 mL) at ambient temperature was added carbonyl diimidazole (9.67 gm, 58 mmol). The solution was stirred for 30 minutes. To this reaction was added 4-(5-(3,5-dichloro-4-fluorophenyl)-5-(trifluoromethyl)-4,5-dihydroisoxazol-3-yl)-1-naphthoic acid (23.0 gm, 49 mmol) as a solid. The solution was stirred for three hours and was then concentrated to remove solvent. The material was partitioned between ethyl acetate (100 mL) and water (200 mL). The organics were concentrated and the product was purified on a silica column (340 gm) by elution with methylene chloride and 0-15% ethyl acetate. $^1$HNMR (CDCl$_3$) δ ppm: 8.82 (1H), 8.33 (1H), 7.76-7.60 (5H), 7.50 (1H), 6.30 (1H) 4.60 (1H), 4.25 (1H), 3.90 (1H), 3.70 (2H), 3.50 (6H); m/z (Cl) 557 [M−H]$^+$. (Me represents methyl).

Example 20

(E/Z)-4-(5-(3,5-dichloro-4-fluorophenyl)-5-(trifluoromethyl)-4,5-dihydroisoxazol-3-yl)-N-(2-(ethoxyimino)ethyl)-1-naphthamide

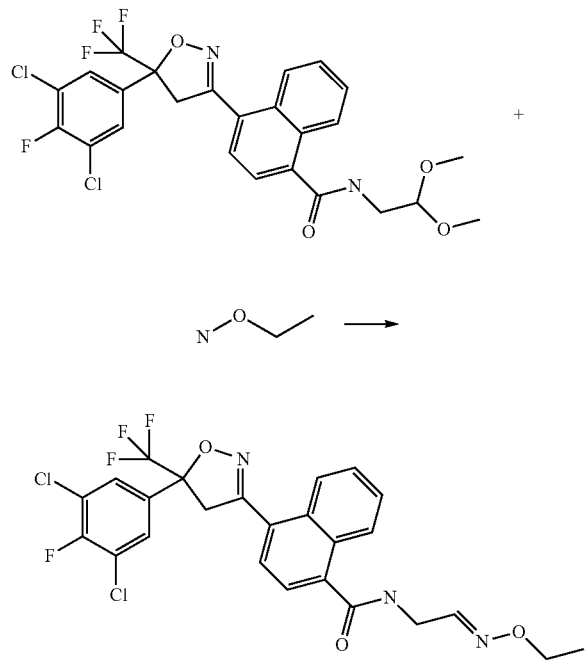

4-[5-(3,5-dichloro-4-fluorophenyl)-5-(trifluoromethyl)-4,5-dihydroisoxazol-3-yl]-N-(2,2-dimethoxyethyl)-1-naphthamide (0.05 mmol) was dissolved in a 3:1 mixture of methanol and tetrahydrofuran (1 mL). O-ethylhydroxylamine (0.1 mmol) was added, followed by 3N HCl(aq) (0.25 ml) and silica supported p-toluenesulfonic acid (100 mg). The reaction mixture was heated at 40° C. for 16 hours. The reaction mixture was filtered and concentrated to dryness under reduced pressure. The crude product was purified by preparative HPLC to give the title compound 12.6 mg (MH+ 556, Retention time 7.59 min)

Preparative HPLC conditions: Column: Gemin NX C18 4.6×100, 5μ Mobile phase A: 0.1% TFA in water (v/v); Mobile phase B: 0.1% TFA in acetonitrile (v/v). Gradient: 90.0% H$_2$O/10.0% Acetonitrile linear to 10% H$_2$O/90% Acetonitrile in 8 minutes, hold at 10% H$_2$O/90% Acetonitrile to 10 minutes, re-equilibrate back to 90.0% H$_2$O/10.0% Acetonitrile to 12.0 minutes. Flow: 1.0 mL/minute.

Example 21

(E/Z)-4-(5-(3,5-dichloro-4-fluorophenyl)-5-(trifluoromethyl)-4,5-dihydroisoxazol-3-yl)-N-(2-((2-fluoroethoxy)imino)ethyl)-1-naphthamide

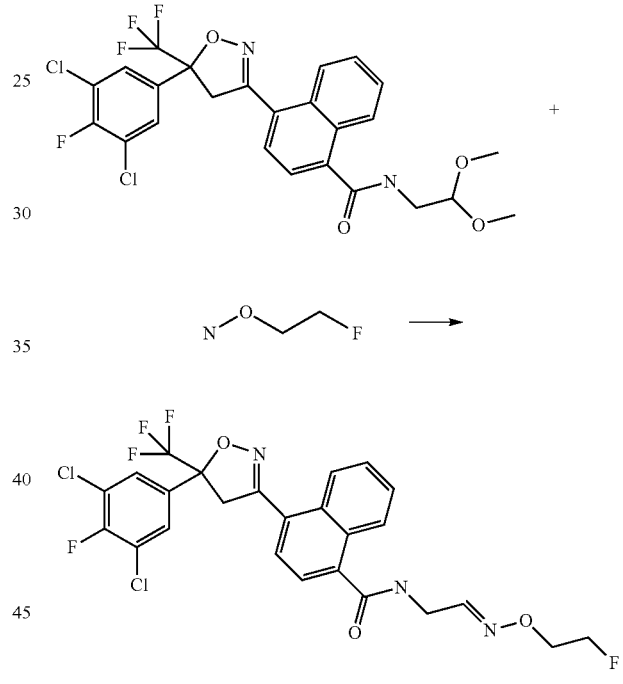

4-[5-(3,5-dichloro-4-fluorophenyl)-5-(trifluoromethyl)-4,5-dihydroisoxazol-3-yl]-N-(2,2-dimethoxyethyl)-1-naphthamide (0.05 mmol) was dissolved in a 3:1 mixture of methanol and tetrahydrofuran (1 mL). O-(2-fluoroethyl) hydroxylamine (0.1 mmol) was added, followed by 3N HCl (aq) (0.25 ml) and silica supported p-toluenesulfonic acid (100 mg). The reaction mixture was heated at 40° C. for 16 hours. The reaction mixture was filtered and concentrated to dryness under reduced pressure. The crude product was purified by preparative HPLC to give the title compound 7.7 mg (MH+ 574, Retention time 7.33 minutes).

Preparative HPLC conditions: Column: Gemin NX C18 4.6×100, 5μ. Mobile phase A: 0.1% TFA in water (v/v); Mobile phase B: 0.1% TFA in acetonitrile (v/v). Gradient: 90.0% H$_2$O/10.0% Acetonitrile linear to 10% H$_2$O/90% Acetonitrile in 8 minutes, hold at 10% H$_2$O/90% Acetonitrile to 10 minutes, re-equilibrate back to 90.0% H$_2$O/10.0% Acetonitrile to 12.0 minutes. Flow: 1.0 mL/minute.

Example 22

(E/Z)—N-(2-((cyclopropylmethoxy)imino)ethyl)-4-(5-(3,5-dichloro-4-fluorophenyl)-5-(trifluoromethyl)-4,5-dihydroisoxazol-3-yl)-1-naphthamide

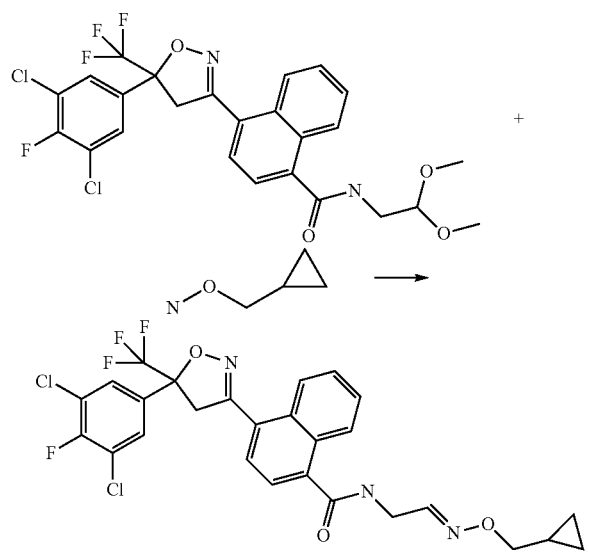

4-[5-(3,5-dichloro-4-fluorophenyl)-5-(trifluoromethyl)-4,5-dihydroisoxazol-3-yl]-N-(2,2-dimethoxyethyl)-1-naphthamide (0.05 mmol) was dissolved in a 3:1 mixture of methanol and tetrahydrofuran (1 mL). O-(cyclopropylmethyl) hydroxylamine (0.1 mmol) was added, followed by 3N HCl (aq) (0.25 ml) and silica supported p-toluenesulfonic acid (100 mg). The reaction mixture was heated at 40° C. for 16 hours. The reaction mixture was filtered and concentrated to dryness under reduced pressure. The crude product was purified by preparative HPLC to give the title compound 13.7 mg (MH+ 582, Retention time 6.31 minutes).

Preparative HPLC conditions: Column: Gemin NX C18 4.6×100, 5μ Mobile phase A: 0.1% FA in water (v/v); Mobile phase B: 0.1% FA in acetonitrile (v/v). Gradient: 90.0% H₂O/10.0% Acetonitrile linear to 10% H₂O/90% Acetonitrile in 8 minutes, hold at 10% H₂O/90% Acetonitrile to 10 minutes, re-equilibrate back to 90.0% H₂O/10.0% Acetonitrile to 12.0 minutes. Flow: 1.0 mL/minute.

Preparation 38: 4-[5-(3-Fluoro-5-trifluoromethyl-phenyl)-5-trifluoromethyl-4,5-dihydro-isoxazol-3-yl]-naphthalene-1-carboxylic acid methyl ester

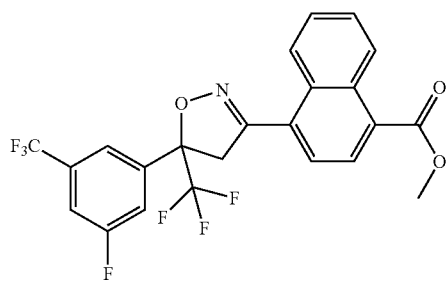 [SMILES: COC(=O)c1ccc(C2=NOC(c3cc(F)cc(C(F)(F)F)c3)(C(F)(F)F)C2)c2ccccc12]

Prepared according to Preparation 6 substituting 1-fluoro-3-(trifluoromethyl)-5-(3,3,3-trifluoroprop-1-en-2-yl)benzene for 1,3-dichloro-2-fluoro-5-(3,3,3-trifluoroprop-1-en-2-yl)benzene. Yield 56.74%) $^1$H NMR (400 MHz, CDCl3) δ: 3.92 (d, J=17.32 Hz, 1H), 4.02 (s, 3H), 4.32 (d, J=17.24 Hz, 1H), 7.43 (d, J=7.96 Hz, 1H), 7.54 (d, J=7.64 Hz, 1H), 7.60-7.70 (m, 4H), 8.08 (d, J=7.56 Hz, 1H), 8.78-8.80 (m, 1H), 8.86-8.88 (m, 1H); LC-MS (m/z): =484.10 (M−H).

Preparation 39: 4-[5-(3-Fluoro-5-trifluoromethyl-phenyl)-5-trifluoromethyl-4,5-dihydro-isoxazol-3-yl]-naphthalene-1-carboxylic acid

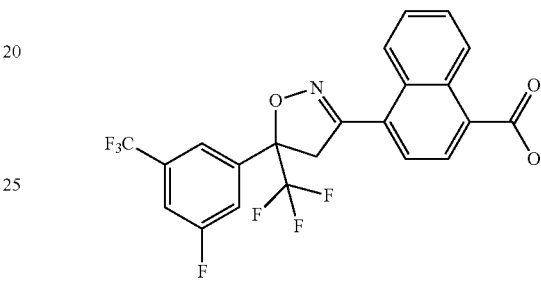

Prepared from the compound of Preparation 38 according to the method of Preparation 7. Yield 92.27%. $^1$H NMR (400 MHz, CDCl₃) δ: 3.92 (d, J=16.6 Hz, 1H), 4.28 (d, J=17.20 Hz, 1H), 7.43 (d, J=7.88 Hz, 1H), 7.54-7.69 (m, 5H), 8.24 (d, J=6.68 Hz, 1H), 8.77-8.79 (m, Hz, 1H), 9.01 (d, J=5.44 Hz, 1H); LC-MS (m/z): =470.0 (M−H).

Preparation 40: 4-[5-(3-Fluoro-5-trifluoromethyl-phenyl)-5-trifluoromethyl-4,5-dihydro-isoxazol-3-yl]-naphthalene-1-carboxylic acid (2-hydroxy-ethyl)-amide

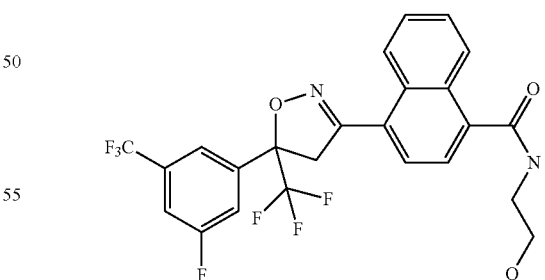

Prepared from the compound of Preparation 39 according to the method of Preparation 8. Yield 69.23%. $^1$H NMR (400 MHz, CDCl₃) δ: 3.70-3.74 (m, 2H), 3.89-3.93 (m, 3H), 4.30 (d, J=17.28 Hz, 1H), 6.45 (bs, 1H), 7.44 (d, J=7.36 Hz, 1H), 7.50 (d, J=7.44 Hz, 1H), 7.60 (d, J=7.36 Hz, 1H), 7.62-7.70 (m, 4H), 8.30 (dd, J₁=1.88 Hz, J₂=7.6 Hz, 1H), 8.82 (dd, J₁=2.2 Hz, J₂=8.0 Hz, 1H); LC-MS (m/z): =515.10 (M+H).

Preparation 41: 4-[5-(3-Fluoro-5-trifluoromethyl-phenyl)-5-trifluoromethyl-4,5-dihydro-isoxazol-3-yl]-naphthalene-1-carboxylic acid (2-oxo-ethyl)-amide

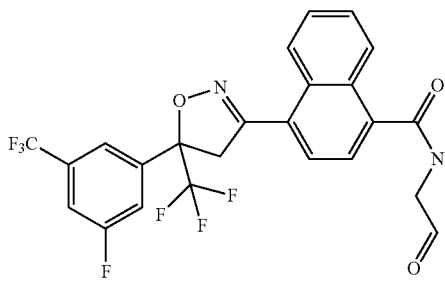 [SMILES: O=CCNC(=O)c1ccc(C2=NOC(c3cc(F)cc(C(F)(F)F)c3)(C(F)(F)F)C2)c2ccccc12]

Prepared from the compound of Preparation 40 according to the method of Preparation 9. Yield 69.6%. ¹H NMR (400 MHz, DMSO-d6) δ: 3.92 (d, J=17.16 Hz, 1H), 4.32 (dd, $J_1$=3.12 Hz, $J_2$=17.24 Hz, 1H), 4.55 (d, J=4.92 Hz, 2H), 7.42-7.44 (m, 2H), 7.53 (d, J=7.4 Hz, 2H), 7.61-7.70 (m, 7H), 8.33 (dd, $J_1$=1.88 Hz, $J_2$=9.44 Hz, 1H), 8.84 (dd, $J_1$=2.16 Hz, $J_2$=7.40 Hz, 1H), 9.82 (s, 1H); LC-MS (m/z): =510.80 (M−H).

Example 23

(E/Z)-4-(5-(3-fluoro-5-(trifluoromethyl)phenyl)-5-(trifluoromethyl)-4,5-dihydroisoxazol-3-yl)-N-(2-(methoxyimino)ethyl)-1-naphthamide

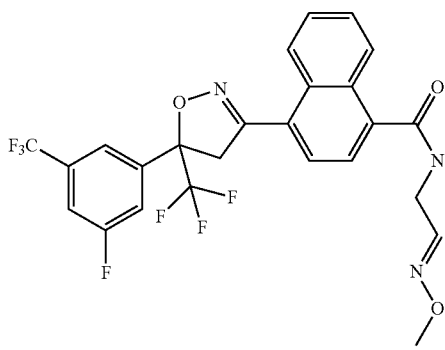 [SMILES: CO/N=C/CNC(=O)c1ccc(C2=NOC(c3cc(F)cc(C(F)(F)F)c3)(C(F)(F)F)C2)c2ccccc12]

Prepared from the compound of Preparation 41, according to the method of Example 3. Yield 37.88%. ¹H NMR (400 MHz, CDCl₃) δ: (Mixture of E and Z isomer) 3.84 (s, 2H), 3.90-3.94 (m, 1H), 3.92 (s, 1H), 4.29-4.36 (m, 3H), 7.43 (d, J=7.96 Hz, 1H), 7.50-7.55 (m, 2H), 7.56-7.69 (m, 6H), 8.26-8.35 (m, 1H), 8.86 (d, J=2.36 Hz, 1H); LC-MS (m/z): = 539.90 (M−H).

Preparation 42: 4-[5-(3-Chloro-4-fluoro-phenyl)-5-trifluoromethyl-4,5-dihydro-isoxazol-3-yl]naphthalene-1-carboxylic acid methyl ester

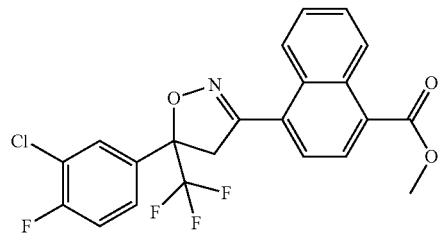 [SMILES: COC(=O)c1ccc(C2=NOC(c3ccc(F)c(Cl)c3)(C(F)(F)F)C2)c2ccccc12]

Prepared according to Preparation 6 substituting 2-chloro-1-fluoro-4-(3,3,3-trifluoroprop-1-en-2-yl)benzene for 1,3-dichloro-2-fluoro-5-(3,3,3-trifluoroprop-1-en-2-yl)benzene. Yield=65.38%. ¹H NMR (400 MHz, CDCl3) δ: 3.95 (d, J=16.4 Hz, 1H), 4.01 (s, 3H), 4.26 (d, J=16.4 Hz, 1H), 7.22-7.24 (m, 1H), 7.52-7.54 (m, 2H), 7.64-7.73 (m, 3H), 8.09 (d, J=7.52 Hz, 1H), 8.77-8.88 (m, 2H); LC-MS (m/z): =449.70 (M−H).

Preparation 43: 4-[5-(3-Chloro-4-fluoro-phenyl)-5-trifluoromethyl-4,5-dihydro-isoxazol-3-yl]-naphthalene-1-carboxylic acid

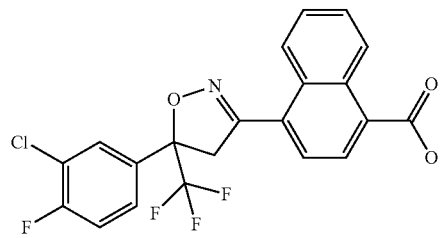 [SMILES: O=C(O)c1ccc(C2=NOC(c3ccc(F)c(Cl)c3)(C(F)(F)F)C2)c2ccccc12]

Prepared from the compound of Preparation 42 according to the method of Preparation 7. Yield=84.84%. LC-MS (m/z): = 438.00 (M+H).

Preparation 44: 4-[5-(3-Chloro-4-fluoro-phenyl)-5-trifluoromethyl-4,5-dihydro-isoxazol-3-yl]-naphthalene-1-carboxylic acid (2-hydroxy-ethyl)-amide

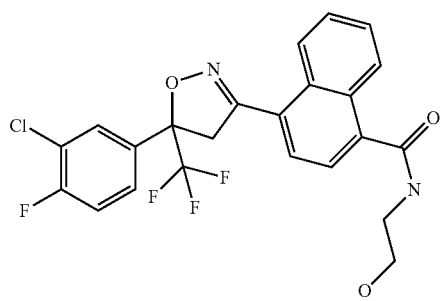 [SMILES: O=C(NCCO)c1ccc(C2=NOC(c3ccc(F)c(Cl)c3)(C(F)(F)F)C2)c2ccccc12]

Prepared from the compound of Preparation 43 according to the method of Preparation 8. Yield 86.7%. ¹H NMR (400 MHz, CDCl₃) δ: 1.24-1.26 (m, 1H), 3.69-3.73 (m, 2H), 3.86-

3.90 (m, 3H), 4.24 (d, J=17.2 Hz, 1H), 6.49-6.50 (m, 1H), 7.22-7.24 (m, 1H), 7.46 (d, J=7.4 Hz, 1H), 7.51-7.57 (m, 2H), 7.59-7.65 (m, 2H), 7.71-7.73 (m, 1H), 8.27-8.29 (m, 1H), 8.78-8.80 (m, 1H); LC-MS (m/z): =481.30 (M+H).

Preparation 45: 4-[5-(3-Chloro-4-fluoro-phenyl)-5-trifluoromethyl-4,5-dihydro-isoxazol-3-yl]-naphthalene-1-carboxylic acid (2-oxo-ethyl)-amide

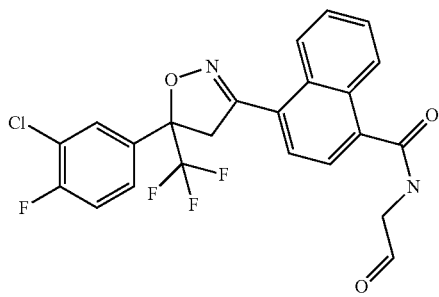 [SMILES: O=CCNC(=O)c1ccc(C2=NOC(c3ccc(F)c(Cl)c3)(C(F)(F)F)C2)c2ccccc12]

Prepared from the compound of Preparation 44 according to the method of Preparation 9. LC-MS (m/z): =477.00 (M−H).

Example 24

(E/Z)-4-(5-(3-chloro-4-fluorophenyl)-5-(trifluoromethyl)-4,5-dihydroisoxazol-3-yl)-N-(2-(methoxyimino)ethyl)-1-naphthamide

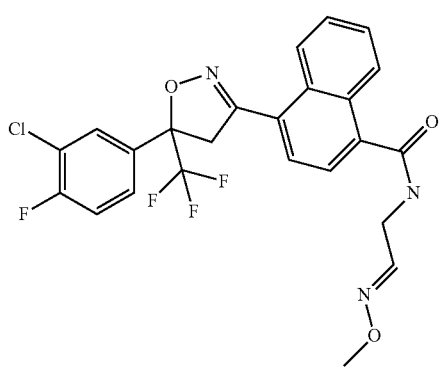 [SMILES: CO/N=C/CNC(=O)c1ccc(C2=NOC(c3ccc(F)c(Cl)c3)(C(F)(F)F)C2)c2ccccc12]

Prepared from the compound of Preparation 45, according to the method of Example 3. Yield 28.04%. $^1$H NMR (400 MHz, CDCl$_3$) δ: (Mixture of E and Z isomer) 3.84 (s, 2H), 3.87-3.92 (m, 2H), 4.23-4.37 (m, 2H), 6.41-6.51 (m, 1H), 7.48-7.55 (m, 3H), 7.63-7.66 (m, 3H), 7.71-7.73 (m, 1H), 8.26-8.24 (m, 1H), 8.26-8.35 (m, 1H), 8.80-8.82 (m, 1H); LC-MS (m/z): =506.20 (M−H), Preparation 46: 4-[5-(4-Ffluoro-3-trifluoromethyl-phenyl)-5-trifluoromethyl-4,5-dihydro-isoxazol-3-yl]-naphthalene-1-carboxylic acid methyl ester

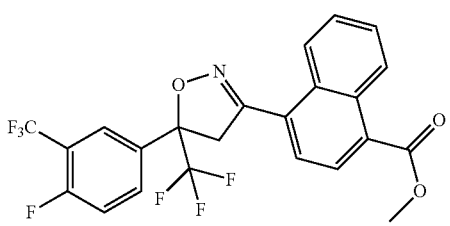 [SMILES: COC(=O)c1ccc(C2=NOC(c3ccc(F)c(C(F)(F)F)c3)(C(F)(F)F)C2)c2ccccc12]

Prepared according to Preparation 6 substituting 1-fluoro-2-(trifluoromethyl)-4-(3,3,3-trifluoroprop-1-en-2-yl)benzene for 1,3-dichloro-2-fluoro-5-(3,3,3-trifluoroprop-1-en-2-yl)benzene. Yield=65%. $^1$H NMR (400 MHz, CDCl3) δ: 3.92 (d, J=17.24 Hz, 1H), 4.02 (s, 3H), 4.31 (d, J=17.24 Hz, 1H), 7.33 (t, J=9.2 Hz, 1H), 7.54 (d, J=7.6 Hz, 1H), 7.64-7.69 (m, 2H), 7.85-7.90 (m, 2H), 8.09 (d, J=7.56 Hz, 1H), 8.77-8.79 (m, 1H), 8.86-8.88 (m, 1H); LC-MS (m/z): =486.0 (M+H).

Preparation 47: 4-[5-(4-Ffluoro-3-trifluoromethyl-phenyl)-5-trifluoromethyl-4,5-dihydro-isoxazol-3-yl]-naphthalene-1-carboxylic acid

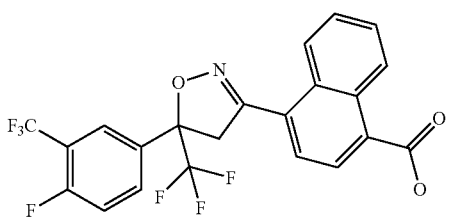 [SMILES: O=C(O)c1ccc(C2=NOC(c3ccc(F)c(C(F)(F)F)c3)(C(F)(F)F)C2)c2ccccc12]

Prepared from the compound of Preparation 46 according to the method of Preparation 7. Yield=98.96%. $^1$H NMR (400 MHz, CDCl3) δ: 3.96 (d, J=17.24 Hz, 1H), 4.32 (d, J=17.32 Hz, 1H), 7.33 (t, J=9.2 Hz, 1H), 7.58 (d, J=7.28 Hz, 1H), 7.68-7.75 (m, 2H), 7.86-7.90 (m, 2H), 8.29 (d, J=7.48 Hz, 1H), 8.79 (d, J=8.32 Hz, 1H), 9.04 (d, J=7.72 Hz, 1H); LC-MS (m/z): =472.4 (M+H).

Preparation 48: 4-[5-(4-Ffluoro-3-trifluoromethyl-phenyl)-5-trifluoromethyl-4,5-dihydro-isoxazol-3-yl]-naphthalene-1-carboxylic acid (2-hydroxy-ethyl)-amide

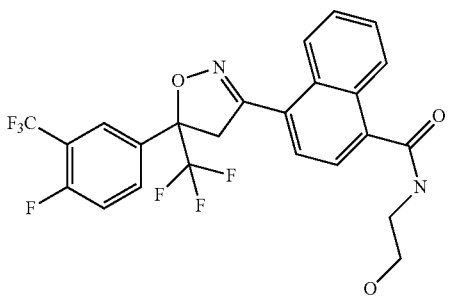 [SMILES: O=C(NCCO)c1ccc(C2=NOC(c3ccc(F)c(C(F)(F)F)c3)(C(F)(F)F)C2)c2ccccc12]

Prepared from the compound of Preparation 47 according to the method of Preparation 8. Yield 58.30%. $^1$H NMR (400 MHz, CDCl$_3$) δ: 3.67-3.74 (m, 2H), 3.88-3.94 (m, 3H), 4.30 (d, J=17.16 Hz, 1H), 7.32 (t, J=9.2 Hz, 1H), 7.49 (d, J=7.4 Hz, 1H), 7.59 (d, J=7.44 Hz, 1H), 7.62-7.67 (m, 1H), 7.85-7.90 (m, 2H), 8.19-8.31 (m, 1H), 8.79-8.82 (m, 1H); LC-MS (m/z): =514.90 (M+H).

Preparation 49: 4-[5-(4-fluoro-3-trifluoromethyl-phenyl)-5-trifluoromethyl-4,5-dihydro-isoxazol-3-yl]-naphthalene-1-carboxylic acid (2-oxo-ethyl)-amide

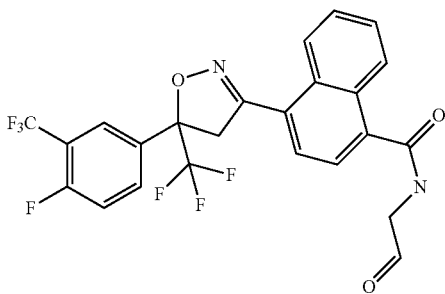 [SMILES: O=CCNC(=O)c1ccc(C2=NOC(c3ccc(F)c(C(F)(F)F)c3)(C(F)(F)F)C2)c2ccccc12]

Prepared from the compound of Preparation 48 according to the method of Preparation 9.

Example 25

(E/Z)-4-(5-(4-fluoro-3-(trifluoromethyl)phenyl)-5-(trifluoromethyl)-4,5-dihydroisoxazol-3-yl)-N-(2-(methoxyimino)ethyl)-1-naphthamide

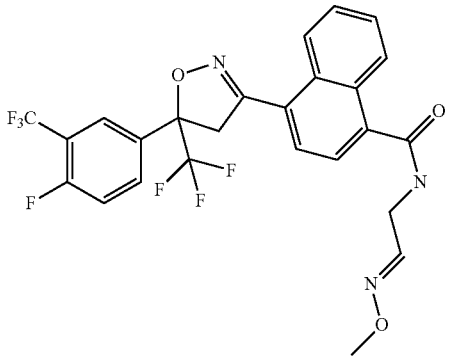 [SMILES: CO/N=C/CNC(=O)c1ccc(C2=NOC(c3ccc(F)c(C(F)(F)F)c3)(C(F)(F)F)C2)c2ccccc12]

Prepared from the compound of Preparation 49, according to the method of Example 3 Yield 14%. $^1$H NMR (400 MHz, CDCl$_3$) δ: (Mixture of E and Z isomer) 3.84 (s, 2H), 3.88-3.93 (m, 1H), 3.92 (s, 1H), 4.28-4.37 (m, 3H), 6.38-6.50 (m, 1H),), 7.32 (t, J=9.2 Hz, 1H), 7.50-7.58 (m, 2H), 7.61-7.67 (m, 3H), 7.85-7.90 (m, 2H), 8.27-8.34 (m, 1H), 8.81 (dd, J1=2.2 Hz, J2=8.04 Hz, 1H); LC-MS (m/z): =542.0 (M+H).

As previously described in Scheme 1a, Intermediate 3 can also be synthesized according to the following preparations.

Preparation 50: 4-Methyl-naphthalene-1-carboxylic acid methyl ester

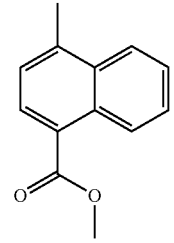

To a stirred solution of 4-methyl-naphthalene-1-carboxylic acid (10 g, 53.70 mmol) in dry DMF (50 mL) was added potassium carbonate (11.14 g, 80.55 mmol) at room temperature. Resulting reaction mixture was stirred for 30 minutes at room temperature. Then reaction mixture was cooled to 0° C. and methyl iodide (11.44 g, 3.04 mL, 80.55 mmol) was added dropwise. Resulting reaction mixture was stirred for 3 hours at room temperature. Progress of reaction was monitored by TLC using 10% EtOAc in hexane. Rf of new spot and stating material was 0.7 and 0.1, respectively. After consumption of starting material, reaction mixture was quenched with ice cold water (150 mL) and extracted with EtOAc (2×150 mL). Combined organic layer was washed with water (300 mL), brine (200 mL) and dried over sodium sulphate. Organic layer was evaporated in vacuo to afford orange colored thick oil. Crude compound was purified by column chromatography using 100-200 mesh silica gel. Desired compound was eluted in 9% in EtOAc in hexane to afford colorless liquid (10.85 g, 99%). $^1$H NMR (400 MHz, CDCl3) δ: 2.73 (s, 3H), 3.98 (S, 3H), 7.34 (d, J=7.4 Hz, 1H), 7.54-7.63 (m, 2H), 8.04 (d, J=7.92 Hz, 1H), 8.08 (d, J=7.44 Hz, 1H), 8.95 (d, J=8.12 Hz, 1H); LC-MS (m/z): =201.10 (M+H).

Preparation 51: 4-Bromomethyl-naphthalene-1-carboxylic acid methyl ester

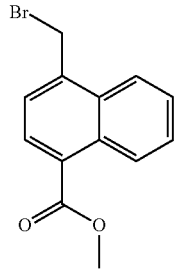 [SMILES: COC(=O)c1ccc(CBr)c2ccccc12]

To a stirred solution of 4-methyl-naphthalene-1-carboxylic acid methyl ester (Preparation 50, 10.85 g, 54.18 mmol) in CCl$_4$ (500 mL) was added N-bromosuccinamide (9.93 gm, 55.81 mmol) followed by AIBN (0.1 g, 0.612 mmol) at room temperature. Resulting reaction mixture was refluxed for 3 hours. Progress of reaction was monitored by TLC using 5% EtOAc in hexane. Rf of new spot and starting material was 0.8 and 0.7 respectively. After consumption of starting material, reaction mixture was concentrated in vacuo to residue. Residue was dissolved in EtOAc (300 mL) and washed with water (2×300 mL), brine (300 mL), dried over sodium sulphate and evaporated in vacuo to get pale yellow semisolid. Crude was purified by column chromatography using 100-200 mesh silica gel. Desired product was eluted in 4% EtOAc in hexane to afford white solid (10.5 g, 69.39%). $^1$H NMR (400 MHz, CDCl3) δ: 4.00 (s, 3H), 4.93 (s, 2H), 7.56 (d, J=7.48 Hz, 1H), 7.62-7.68 (m, 2H), 8.06 (d, J=7.4 Hz, 1H), 8.17-8.20 (m, 1H), 8.90-8.93 (m, 1H).

Preparation 52: 4-Formyl-naphthalene-1-carboxylic acid methyl ester

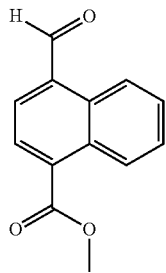

To a stirred solution of 4-bromomethyl-naphthalene-1-carboxylic acid methyl ester (Preparation 51, 10.5 g, 37.63 mmol) in DMSO (99.36 mL) was added sodium bicarbonate (6.32 g, 75.27 mmol) at room temperature. Resulting reaction mixture was heated at 95° C. for 3 hours. Progress of the reaction was monitored by TLC using 10% EtOAc in hexane. Rf of new spot and starting material was 0.7 and 0.8 respectively. After consumption of starting material, reaction mixture was quenched with water (400 mL) and extracted with EtOAc (2×300 mL). Combined organic layer was dried over sodium sulphate and evaporated off in vacuo to get brown colored thick mass. Crude compound was purified by column chromatography using 100-200 mesh silica gel. Desired product was eluted in 4.5% EtOAc in hexane to afford faint green solid (4.2 g, 52.17%). Compound the same as that from Preparation 3.

BIOLOGICAL ASSAYS

The biological activity of the compounds of the present invention was tested against fleas and horn flies using the test methods described below.

Horn Fly (*Haematobia irritans*) Feed Assay

Formula (1) compounds were dissolved in DMSO and aliquots were added to citrated bovine blood in a membrane covered Petri dish. Approximately ten horn flies were placed onto each Petri dish and covered. The flies were allowed to feed on the treated blood cell. Flies were held at approximately 80° F. with a minimum of approximately 50% relative humidity. Flies were examined for knockdown and mortality at approximately 2 and 24 hours. Endpoint data were recorded as a lethal dose 90% ($LD^{90}$) in μg/mL. In this assay, Examples 1, 2, 3, 5, 6, 12, 21, and 23-25 demonstrated an $LD^{90}$ of 1 μg/mL; Examples 11, 13-15, 17-20, and 22 demonstrated an $LD^{90}$ of 3 μg/mL; and Example 10 demonstrated an $LD^{90}$ of 10 μg/mL.

Flea (*Ctenocephalides felis*) Membrane Feed Assay-Adult

Formula (1) compounds were dissolved in DMSO and aliquots were added to citrated bovine blood in a membrane covered Petri dish pre-warmed to 37° C. Feeding tubes containing approximately 30-35 adult fleas were placed onto the Petri dishes. The fleas were allowed to feed for approximately 2 hours. Fleas were observed for knockdown and/or death at approximately 2 and 24 hours. Endpoint data were recorded as an efficacious dose 80% ($ED^{80}$) in μg/mL. In this assay, Examples 3 and 16-17 demonstrated an $ED^{80}$ of 1 μg/mL; Examples 5, 6, and 11 demonstrated an $ED^{80}$ of 3 μg/mL; Examples 1, 2, and 10 demonstrated an $ED^{80}$ of 10 μg/mL.

We claim:
1. A compound of Formula (1)

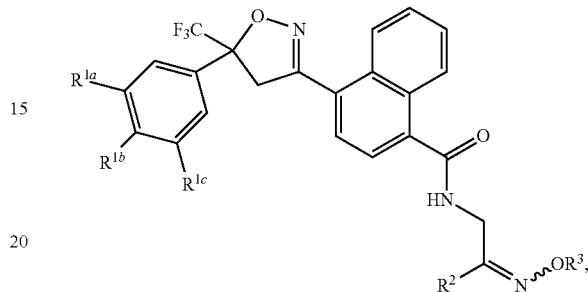

wherein
$R^{1a}$, $R^{1b}$, and $R^{1c}$ are each independently selected from hydrogen, halo, cyano, $C_1$-$C_6$alkyl, $C_1$-$C_6$haloalkyl, $C_1$-$C_6$alkoxy, $C_0$-$C_6$alkyl $C_3$-$C_6$cycloalkyl, and $C_1$-$C_6$haloalkoxy;

$R^2$ is H, $C_1$-$C_6$alkyl, $C_0$-$C_6$alkyl phenyl, $C_0$-$C_6$alkyl heteroaryl, $C_0$-$C_6$alkyl $C_3$-$C_6$cycloalkyl, or $C_0$-$C_6$alkyl heterocycle;

$R^3$ is H, $C_1$-$C_6$alkyl, $C_0$-$C_6$alkyl $C_3$-$C_6$cycloalkyl, $C_2$-$C_6$alkenyl, $C_0$-$C_6$alkyl phenyl, $C_1$-$C_4$alkyl-O-phenyl, $C_0$-$C_6$alkyl heterocycle, or $C_0$-$C_6$alkyl heteroaryl;

each of $R^2$ and $R^3$ $C_1$-$C_6$alkyl or $C_0$-$C_6$alkyl$C_3$-$C_6$cycloalkyl can be optionally and independently substituted by at least one substituent selected from cyano, halo, hydroxyl, oxo, $C_1$-$C_6$alkoxy, $C_1$-$C_6$haloalkoxy, $C_1$-$C_6$haloalkyl, —S(O)$_p$$R^c$, —SH, —S(O)$_p$$NR^aR^b$, —$NR^aR^b$, —$NR^aC(O)R^b$, —SC(O)$R^c$, —SCN, or —C(O)$NR^aR^b$; and wherein $R^2$ and $R^3$$C_0$-$C_6$alkyl phenyl, $C_0$-$C_6$alkyl heteroaryl, or $C_0$-$C_6$alkyl heterocycle moiety can be further optionally substituted with at least one substituent selected from cyano, halo, oxo, =S, =$NR^d$, hydroxyl, $C_1$-$C_6$alkoxy, $C_1$-$C_6$alkyl, $C_1$-$C_6$haloalkyl, —SH, —S(O)$_p$R, $C_1$-$C_6$haloalkoxy, Het, and phenyl;

R is $C_1$-$C_6$alkyl or $C_3$-$C_6$cycloalkyl each optionally substituted by at least one halo;

$R^a$ is hydrogen, $C_1$-$C_6$alkyl, or $C_0$-$C_3$alkyl$C_3$-$C_6$cycloalkyl; wherein the alkyl and alkylcycloalkyl is optionally substituted by cyano or at least one halo substituent;

$R^b$ is hydrogen, $C_1$-$C_6$alkyl, $C_3$-$C_6$cycloalkyl, $C_0$-$C_3$alkylphenyl, $C_0$-$C_3$alkylheteroaryl, or $C_0$-$C_3$alkylheterocycle, each optionally substituted, where chemically possible, with at least one substituent selected from hydroxyl, cyano, halo, or —S(O)$_p$R;

or wherein $R^a$ and $R^b$, with the N atom to which they are attached can form a 4-7 membered ring which may optionally include at least one additional heteroatom selected from N, O, and S;

$R^c$ is $C_1$-$C_6$alkyl, $C_1$-$C_6$haloalkyl, $C_1$-$C_6$haloalkyl$C_3$-$C_6$cycloalkyl, $C_0$-$C_3$alkyl$C_3$-$C_6$cycloalkyl, $C_0$-$C_3$alkylphenyl, $C_0$-$C_3$alkylheteroaryl, or $C_0$-$C_3$alkylheterocycle each optionally substituted with at least one substituent selected from cyano, halo, hydroxyl, oxo, $C_1$-$C_6$alkoxy, $C_1$-$C_6$haloalkoxy, $C_1$-$C_6$haloalkyl, —S(O)$_p$R, —SH, —S(O)$_p$NR$^a$R$^b$, —NR$^a$R$^b$, —NR$^a$C(O)R$^b$, —SC(O)R$^b$, —SCN, or —C(O)NR$^a$R$^b$;

R$^d$ is hydrogen, $C_1$-$C_6$alkyl, hydroxyl, cyano, nitro, —S(O)$_p$R$^c$, or $C_1$-$C_6$alkoxy;

p is the integer 0, 1, or 2; and

⁓ is a bond that represents E and Z geometric isomers; stereoisomers thereof, and pharmaceutically or veterinarily acceptable salts thereof.

2. The compound of claim 1 wherein

R$^{1a}$, R$^{1b}$, and R$^{1c}$ are each independently selected from hydrogen, halo, cyano, $C_1$-$C_6$alkyl, $C_1$-$C_6$haloalkyl, and $C_0$-$C_6$alkyl $C_3$-$C_6$cycloalkyl.

3. The compound of claim 2, wherein

R$^{1a}$, R$^{1b}$, and R$^{1c}$ are each independently selected from hydrogen, chloro, fluoro, bromo, cyano, $C_1$-$C_6$alkyl, and $C_1$-$C_6$haloalkyl; and R$^2$ is H, $C_1$-$C_6$alkyl, cyclopropyl, or $C_1$-$C_6$alkyl substituted with halo.

4. The compound of claim 3 wherein

R$^{1a}$, R$^{1b}$, and R$^{1c}$ are each independently selected from hydrogen, chloro, fluoro, and $C_1$-$C_6$haloalkyl; and R$^2$ is H, $C_1$-$C_6$alkyl, or —CF$_3$.

5. The compound of claim 4 wherein

R$^3$ is H, $C_1$-$C_6$alkyl, $C_0$-$C_6$alkyl $C_3$-$C_6$cycloalkyl, or $C_1$-$C_6$alkyl substituted with halo.

6. The compound of claim 5 wherein

R$^{1a}$, R$^{1b}$, and R$^{1c}$ are each independently selected from hydrogen, chloro, fluoro, and —CF$_3$;

R$^2$ is H, methyl, or —CF$_3$, and

R$^3$ is H, methyl, ethyl, propyl, isopropyl, butyl, t-butyl, —CH$_2$CH$_2$F, —CH$_2$CF$_3$, —CH$_2$cyclopropyl, or —CH$_2$CH$_2$cyclopropyl.

7. A compound of claim 1 selected from (E/Z)-4-(5-(3,5-dichloro-4-fluorophenyl)-5-(trifluoromethyl)-4,5-dihydroisoxazol-3-yl)-N-(2-(isopropoxyimino)ethyl)-1-naphthamide;

(E/Z)-4-(5-(3,5-dichloro-4-fluorophenyl)-5-(trifluoromethyl)-4,5-dihydroisoxazol-3-yl)-N-(2-(methoxyimino)ethyl)-1-naphthamide;

(E/Z)—N-(2-(tert-butoxyimino)ethyl)-4-(5-(3,5-dichloro-4-fluorophenyl)-5-(trifluoromethyl)-4,5-dihydroisoxazol-3-yl)-1-naphthamide;

(E/Z)-4-(5-(3,5-dichloro-4-fluorophenyl)-5-(trifluoromethyl)-4,5-dihydroisoxazol-3-yl)-N-(2-(hydroxyimino)ethyl)-1-naphthamide;

(E)-4-(5-(3,5-dichloro-4-fluorophenyl)-5-(trifluoromethyl)-4,5-dihydroisoxazol-3-yl)-N-(3,3,3-trifluoro-2-(hydroxyimino)propyl)-1-naphthamide;

(E)-4-(5-(3,5-dichloro-4-fluorophenyl)-5-(trifluoromethyl)-4,5-dihydroisoxazol-3-yl)-N-(3,3,3-trifluoro-2-(methoxyimino)propyl)-1-naphthamide;

(E)-4-(5-(3,5-dichloro-4-fluorophenyl)-5-(trifluoromethyl)-4,5-dihydroisoxazol-3-yl)-N-(2-(ethoxyimino)-3,3,3-trifluoropropyl)-1-naphthamide;

(E)-4-(5-(3,5-dichloro-4-fluorophenyl)-5-(trifluoromethyl)-4,5-dihydroisoxazol-3-yl)-N-(3,3,3-trifluoro-2-(isopropoxyimino)propyl)-1-naphthamide;

(E/Z)-4-(5-(3,5-dichlorophenyl)-5-(trifluoromethyl)-4,5-dihydroisoxazol-3-yl)-N-(2-(methoxyimino)ethyl)-1-naphthamide;

(E/Z)-4-(5-(3,5-dichlorophenyl)-5-(trifluoromethyl)-4,5-dihydroisoxazol-3-yl)-N-(2-(hydroxyimino)ethyl)-1-naphthamide;

(Z)-4-(5-(3,5-dichloro-4-fluorophenyl)-5-(trifluoromethyl)-4,5-dihydroisoxazol-3-yl)-N-(2-(methoxyimino)propyl)-1-naphthamide;

(E/Z)—N-(2-(ethoxyimino)ethyl)-4-(5-(3,4,5-trichlorophenyl)-5-(trifluoromethyl)-4,5-dihydroisoxazol-3-yl)-1-naphthamide;

(E/Z)—N-(2-(2-fluoroethoxyimino)ethyl)-4-(5-(3,4,5-trichlorophenyl)-5-(trifluoromethyl)-4,5-dihydroisoxazol-3-yl)-1-naphthamide;

(E/Z)—N-(2-(methoxyimino)ethyl)-4-(5-(3,4,5-trichlorophenyl)-5-(trifluoromethyl)-4,5-dihydroisoxazol-3-yl)-1-naphthamide;

(E/Z)-4-(5-(3,4-dichloro-5-(trifluoromethyl)phenyl)-5-(trifluoromethyl)-4,5-dihydroisoxazol-3-yl)-N-(2-(methoxyimino)ethyl)-1-naphthamide;

(E/Z)-4-(5-(3,5-bis(trifluoromethyl)phenyl)-5-(trifluoromethyl)-4,5-dihydroisoxazol-3-yl)-N-(2-(methoxyimino)ethyl)-1-naphthamide;

(E/Z)-4-(5-(3,4-difluoro-5-(trifluoromethyl)phenyl)-5-(trifluoromethyl)-4,5-dihydroisoxazol-3-yl)-N-(2-(methoxyimino)ethyl)-1-naphthamide;

(E/Z)-4-(5-(3-chloro-5-fluorophenyl)-5-(trifluoromethyl)-4,5-dihydroisoxazol-3-yl)-N-(2-(methoxyimino)ethyl)-1-naphthamide;

(E/Z)-4-(5-(3,5-dichloro-4-fluorophenyl)-5-(trifluoromethyl)-4,5-dihydroisoxazol-3-yl)-N-(2-(ethoxyimino)ethyl)-1-naphthamide;

(E/Z)-4-(5-(3,5-dichloro-4-fluorophenyl)-5-(trifluoromethyl)-4,5-dihydroisoxazol-3-yl)-N-(2-((2-fluoroethoxy)imino)ethyl)-1-naphthamide;

(E/Z)—N-(2-((cyclopropylmethoxy)imino)ethyl)-4-(5-(3,5-dichloro-4-fluorophenyl)-5-(trifluoromethyl)-4,5-dihydroisoxazol-3-yl)-1-naphthamide;

(E/Z)-4-(5-(3-fluoro-5-(trifluoromethyl)phenyl)-5-(trifluoromethyl)-4,5-dihydroisoxazol-3-yl)-N-(2-(methoxyimino)ethyl)-1-naphthamide;

(E/Z)-4-(5-(3-chloro-4-fluorophenyl)-5-(trifluoromethyl)-4,5-dihydroisoxazol-3-yl)-N-(2-(methoxyimino)ethyl)-1-naphthamide; and (E/Z)-4-(5-(4-fluoro-3-(trifluoromethyl)phenyl)-5-(trifluoromethyl)-4,5-dihydroisoxazol-3-yl)-N-(2-(methoxyimino)ethyl)-1-naphthamide; stereoisomers thereof, and pharmaceutically or veterinarily acceptable salts thereof.

8. A composition comprising a therapeutic amount of a compound of Formula (1)

(1)

wherein

R$^{1a}$, R$^{1b}$, and R$^{1c}$ are each independently selected from hydrogen, halo, cyano, $C_1$-$C_6$alkyl, $C_1$-$C_6$haloalkyl, $C_1$-$C_6$alkoxy, $C_0$-$C_6$alkyl $C_3$-$C_6$cycloalkyl, and $C_1$-$C_6$haloalkoxy;

R² is H, $C_1$-$C_6$alkyl, $C_0$-$C_6$alkyl phenyl, $C_0$-$C_6$alkyl heteroaryl, $C_0$-$C_6$alkyl $C_3$-$C_6$cycloalkyl, or $C_0$-$C_6$alkyl heterocycle;

R³ is H, $C_1$-$C_6$alkyl, $C_0$-$C_6$alkyl $C_3$-$C_6$cycloalkyl, $C_2$-$C_6$alkenyl, $C_0$-$C_6$alkyl phenyl, $C_1$-$C_4$alkyl-O-phenyl, $C_0$-$C_6$alkyl heterocycle, or $C_0$-$C_6$alkyl heteroaryl;

each of R² and R³$C_1$-$C_6$alkyl or $C_0$-$C_6$alkyl$C_3$-$C_6$cycloalkyl can be optionally and independently substituted by at least one substituent selected from cyano, halo, hydroxyl, oxo, $C_1$-$C_6$alkoxy, $C_1$-$C_6$haloalkoxy, $C_1$-$C_6$haloalkyl, —S(O)$_p$R$^c$, —SH, —S(O)$_p$NR$^a$R$^b$, —NR$^a$R$^b$, —NR$^a$C(O)R$^b$, —SC(O)R$^c$, —SCN, or —C(O)NR$^a$R$^b$; and wherein R² and R³$C_0$-$C_6$alkyl phenyl, $C_0$-$C_6$alkyl heteroaryl, or $C_0$-$C_6$alkyl heterocycle moiety can be further optionally substituted with at least one substituent selected from cyano, halo, oxo, =S, =NR$^d$, hydroxyl, $C_1$-$C_6$alkoxy, $C_1$-$C_6$alkyl, $C_1$-$C_6$haloalkyl, —SH, —S(O)$_p$R, $C_1$-$C_6$haloalkoxy, Het, and phenyl;

R is $C_1$-$C_6$alkyl or $C_3$-$C_6$cycloalkyl each optionally substituted by at least one halo;

R$^a$ is hydrogen, $C_1$-$C_6$alkyl, or $C_0$-$C_3$alkyl$C_3$-$C_6$cycloalkyl; wherein the alkyl and alkylcycloalkyl is optionally substituted by cyano or at least one halo substituent;

R$^b$ is hydrogen, $C_1$-$C_6$alkyl, $C_3$-$C_6$cycloalkyl, $C_0$-$C_3$alkylphenyl, $C_0$-$C_3$alkylheteroaryl, or $C_0$-$C_3$alkylheterocycle, each optionally substituted, where chemically possible, with at least one substituent selected from hydroxyl, cyano, halo, or —S(O)$_p$R;

or wherein R$^a$ and R$^b$, with the N atom to which they are attached can form a 4-7 membered ring which may optionally include at least one additional heteroatom selected from N, O, and S;

R$^c$ is $C_1$-$C_6$alkyl, $C_1$-$C_6$haloalkyl, $C_1$-$C_6$haloalkyl$C_3$-$C_6$cycloalkyl, $C_0$-$C_3$alkyl$C_3$-$C_6$cycloalkyl, $C_0$-$C_3$alkylphenyl, $C_0$-$C_3$alkylheteroaryl, or $C_0$-$C_3$alkylheterocycle each optionally substituted with at least one substituent selected from cyano, halo, hydroxyl, oxo, $C_1$-$C_6$alkoxy, $C_1$-$C_6$haloalkoxy, $C_1$-$C_6$haloalkyl, —S(O)$_p$R, —SH, —S(O)$_p$NR$^a$R$^b$, —NR$^a$R$^b$, —NR$^a$C(O)R$^b$, —SC(O)R$^b$, —SCN, or —C(O)NR$^a$R$^b$;

R$^d$ is hydrogen, $C_1$-$C_6$alkyl, hydroxyl, cyano, nitro, —S(O)$_p$R$^c$, or $C_1$-$C_6$alkoxy;

p is the integer 0, 1, or 2; and

∼∼∼ is a bond that represents E and Z geometric isomers, stereoisomers thereof, and pharmaceutically or veterinarily acceptable salts thereof.

9. The composition of claim 8 further comprising a pharmaceutically or veterinarily acceptable excipient, diluent, or carrier.

10. The composition of claim 9 further comprising at least one additional veterinary agent.

11. The composition of claim 10 wherein said additional veterinary agent is selected from the group consisting of eprinomectin, ivermectin, avermectin, abamectin, selamectin, doramectin, moxidectin, milbemycin oxime, an anthelmintic, DEET, derquantel, demiditraz, amitraz, fipronil, S-methoprene, pyriproxyfen, imidacloprid, indoxacarb, indoxacarb metabolites, metaflumizone, permethrin, amidoacetonitrile, pyrethrin, and spinosad, or mixtures thereof.

12. The composition of claim 11 wherein said additional veterinary agent is selected from ivermectin, avermectin, abamectin, selamectin, doramectin, moxidectin, or milbemycin oxime, and mixtures thereof.

13. The composition of claim 12 wherein said additional veterinary agent is selected from doramectin, moxidectin, milbemycin oxime, and mixtures thereof.

14. A method for the treatment of parasites in an animal comprising administering to said animal an effective amount of a compound of Formula (1)

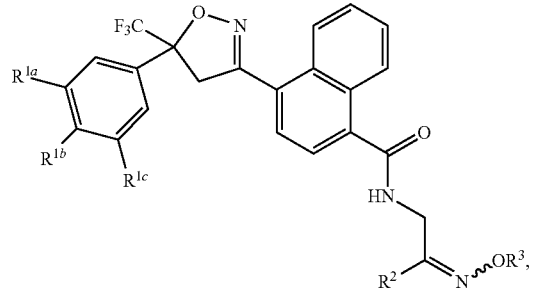

(1)

wherein

R$^{1a}$, R$^{1b}$, and R$^{1c}$ are each independently selected from hydrogen, halo, cyano, $C_1$-$C_6$alkyl, $C_1$-$C_6$haloalkyl, $C_1$-$C_6$alkoxy, $C_0$-$C_6$alkyl $C_3$-$C_6$cycloalkyl, and $C_1$-$C_6$haloalkoxy;

R² is H, $C_1$-$C_6$alkyl, $C_0$-$C_6$alkyl phenyl, $C_0$-$C_6$alkyl heteroaryl, $C_0$-$C_6$alkyl $C_3$-$C_6$cycloalkyl, or $C_0$-$C_6$alkyl heterocycle;

R³ is H, $C_1$-$C_6$alkyl, $C_0$-$C_6$alkyl $C_3$-$C_6$cycloalkyl, $C_2$-$C_6$alkenyl, $C_0$-$C_6$alkyl phenyl, $C_1$-$C_4$alkyl-O-phenyl, $C_0$-$C_6$alkyl heterocycle, or $C_0$-$C_6$alkyl heteroaryl;

each of R² and R³$C_1$-$C_6$alkyl or $C_0$-$C_6$alkyl$C_3$-$C_6$cycloalkyl can be optionally and independently substituted by at least one substituent selected from cyano, halo, hydroxyl, oxo, $C_1$-$C_6$alkoxy, $C_1$-$C_6$haloalkoxy, $C_1$-$C_6$haloalkyl, —S(O)$_p$R$^c$, —SH, —S(O)$_p$NR$^a$R$^b$, —NR$^a$R$^b$, —NR$^a$C(O)R$^b$, —SC(O)R$^c$, —SCN, or —C(O)NR$^a$R$^b$; and wherein R² and R³$C_0$-$C_6$alkyl phenyl, $C_0$-$C_6$alkyl heteroaryl, or $C_0$-$C_6$alkyl heterocycle moiety can be further optionally substituted with at least one substituent selected from cyano, halo, oxo, =S, =NR$^d$, hydroxyl, $C_1$-$C_6$alkoxy, $C_1$-$C_6$alkyl, $C_1$-$C_6$haloalkyl, —SH, —S(O)$_p$R, $C_1$-$C_6$haloalkoxy, Het, and phenyl;

R is $C_1$-$C_6$alkyl or $C_3$-$C_6$cycloalkyl each optionally substituted by at least one halo;

R$^a$ is hydrogen, $C_1$-$C_6$alkyl, or $C_0$-$C_3$alkyl$C_3$-$C_6$cycloalkyl; wherein the alkyl and alkylcycloalkyl is optionally substituted by cyano or at least one halo substituent;

R$^b$ is hydrogen, $C_1$-$C_6$alkyl, $C_3$-$C_6$cycloalkyl, $C_0$-$C_3$alkylphenyl, $C_0$-$C_3$alkylheteroaryl, or $C_0$-$C_3$alkylheterocycle, each optionally substituted, where chemically possible, with at least one substituent selected from hydroxyl, cyano, halo, or —S(O)$_p$R;

or wherein R$^a$ and R$^b$, with the N atom to which they are attached can form a 4-7 membered ring which may optionally include at least one additional heteroatom selected from N, O, and S;

R$^c$ is $C_1$-$C_6$alkyl, $C_1$-$C_6$haloalkyl, $C_1$-$C_6$haloalkyl$C_3$-$C_6$cycloalkyl, $C_0$-$C_3$alkyl$C_3$-$C_6$cycloalkyl, $C_0$-$C_3$alkylphenyl, $C_0$-$C_3$alkylheteroaryl, or $C_0$-$C_3$alkylheterocycle each optionally substituted with at least one substituent selected from cyano, halo, hydroxyl, oxo, $C_1$-$C_6$alkoxy, $C_1$-$C_6$haloalkoxy, $C_1$-$C_6$haloalkyl, —S(O)$_p$R, —SH, —S(O)$_p$NR$^a$R$^b$, —NR$^a$R$^b$, —NR$^a$C(O)R$^b$, —SC(O)R$^b$, —SCN, or —C(O)NR$^a$R$^b$;

R$^d$ is hydrogen, $C_1$-$C_6$alkyl, hydroxyl, cyano, nitro, —S(O)$_p$R$^c$, or $C_1$-$C_6$alkoxy;

p is the integer 0, 1, or 2; and

⌇ is a bond that represents E and Z geometric isomers, stereoisomers thereof, and pharmaceutically or veterinarily acceptable salts thereof.

15. The method of claim 14 wherein the compound is administered topically, orally, or by injection.

16. The method of claim 14 wherein said animal is a companion animal or livestock.

17. The method of claim 16 wherein the companion animal is a dog.

18. The method of claim 16 wherein livestock is bovine.

19. The method of claim 14 wherein the animal is a bird or fish.

* * * * *